United States Patent
Hahn et al.

(10) Patent No.: US 8,835,632 B2
(45) Date of Patent: Sep. 16, 2014

(54) METHODS TO INCREASE THE PHOTOSTABILITY OF DYES

(75) Inventors: Klaus Hahn, Chapel Hill, NC (US);
Alexei Toutchkine, Arlington, MA (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1033 days.

(21) Appl. No.: 12/743,128

(22) PCT Filed: Jun. 20, 2008

(86) PCT No.: PCT/US2008/067678
§ 371 (c)(1),
(2), (4) Date: Sep. 21, 2010

(87) PCT Pub. No.: WO2008/157762
PCT Pub. Date: Dec. 24, 2008

(65) Prior Publication Data
US 2011/0046000 A1    Feb. 24, 2011

Related U.S. Application Data

(60) Provisional application No. 60/936,527, filed on Jun. 21, 2007.

(51) Int. Cl.
C07D 417/06    (2006.01)
C07D 403/06    (2006.01)
C07D 409/06    (2006.01)
C09B 23/10     (2006.01)
C09B 23/01     (2006.01)
G01N 33/58     (2006.01)

(52) U.S. Cl.
CPC ............ G01N 33/582 (2013.01); C09B 23/107 (2013.01); C09B 23/0058 (2013.01)
USPC ........... 544/300; 548/159; 548/428; 548/455; 548/465

(58) Field of Classification Search
USPC .................. 544/300; 548/159, 428, 455, 465
See application file for complete search history.

(56) References Cited

U.S. PATENT DOCUMENTS 7,592,188 B2 * 9/2009 Hahn et al. .................. 435/4

FOREIGN PATENT DOCUMENTS

WO    WO 2005/088308 A2 *   9/2005   ............ G01N 33/53
WO    WO 2008/027075 A2     3/2008

OTHER PUBLICATIONS

Grahn et al. "13C-NMR-Spektren von γ-substituierten pentamethincyanin-farbstoffen mit indolenin-endgruppen", Tetrahedron, 1976, vol. 32, pp. 125-134.*
Toutchkine et al. "Simple One-Pot Preparation of Water-Soluble, Cysteine-Reactive Cyanine and Merocyanine Dyes for Biological Imaging" Bioconjugate Chemistry, 2007, vol. 18, No. 4, pp. 1344-1348.*
Toutchkine et al. "Solvent-Sensitive Dyes to Report Protein Conformational Changes in Living Cells" Journal of the American Chemical Society, 2003, vol. 125, pp. 4132-4145.*
Ernst, L.A., et al., "Cyanine Dye Labeling Reagents for Sulfhydryl Groups," Cytometry, 1989, pp. 3-10.
Grahn, W., and Ch. Reichardt, "C-NMR-Spektren Von γ-Substituierten Pentamethincyanin-Farbstoffen Mit Indolenin-Endgruppen," Tetrahedron, 1976, pp. 125-134, vol. 32.
Toutchkine, A. et al., "Solvent-Sensitive Dyes to Report Protein Conformational Changes in Living Cells," Journal of the American Chemical Society, 2003, pp. 4132-4134, vol. 125(14).
Ushomirsky, M.N., and L.M. Yagupolskii, "Colour Theory of Polyfluoromethine Systems: 1. Single Fluorine Atom in the Polymethine Chain," Dyes and Pigments, 1991, pp. 93-109, vol. 16(2).

* cited by examiner

Primary Examiner — Joseph Kosack
(74) Attorney, Agent, or Firm — Myers Bigel Sibley & Sajovec, P.A.

(57) ABSTRACT

The presently disclosed subject matter provides dyes having an improved photostability, biosensors comprising such dyes, and methods of use thereof, including methods for detecting target molecules in a sample under test and for live-cell imaging. The dyes can include a binding member, including a biomolecule or fragments thereof, which can interact with target molecules of interest and can be specific to a given conformational state or covalent modification, e.g., phosphorylation, of the target molecule. The presently disclosed dyes can be used for detecting changes in the binding, conformational change, or posttranslational modification of the target molecule.

3 Claims, 17 Drawing Sheets

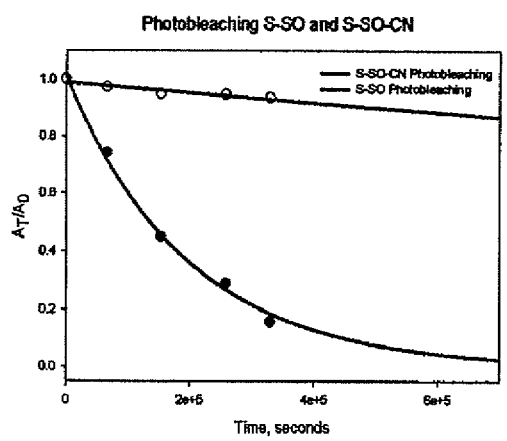
*Fig. 2A*
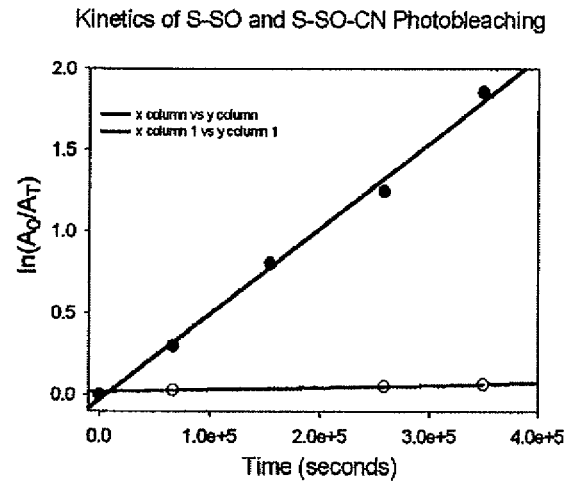
*Fig. 2B*
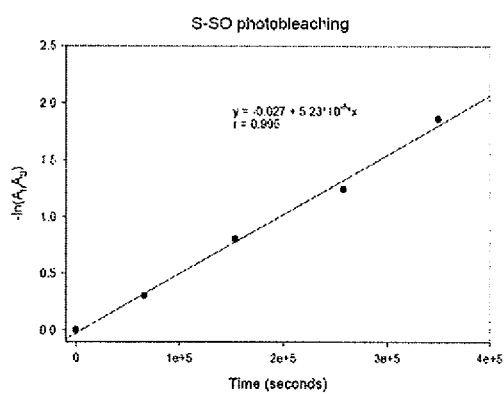
*Fig. 2C*
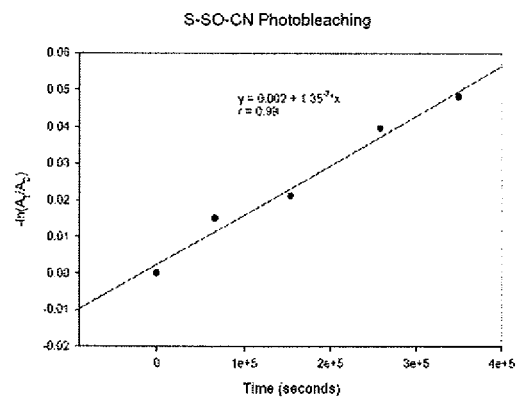
*Fig. 2D*
*Fig. 2*

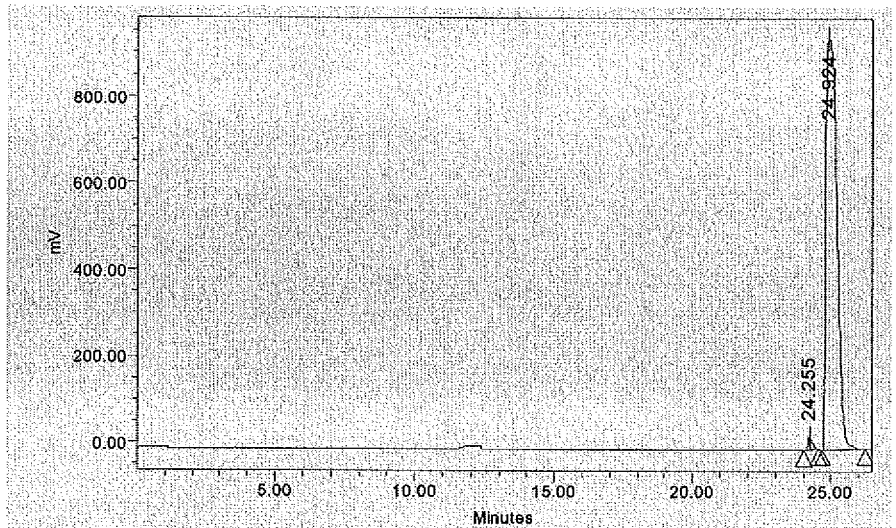
*Fig. 7A*
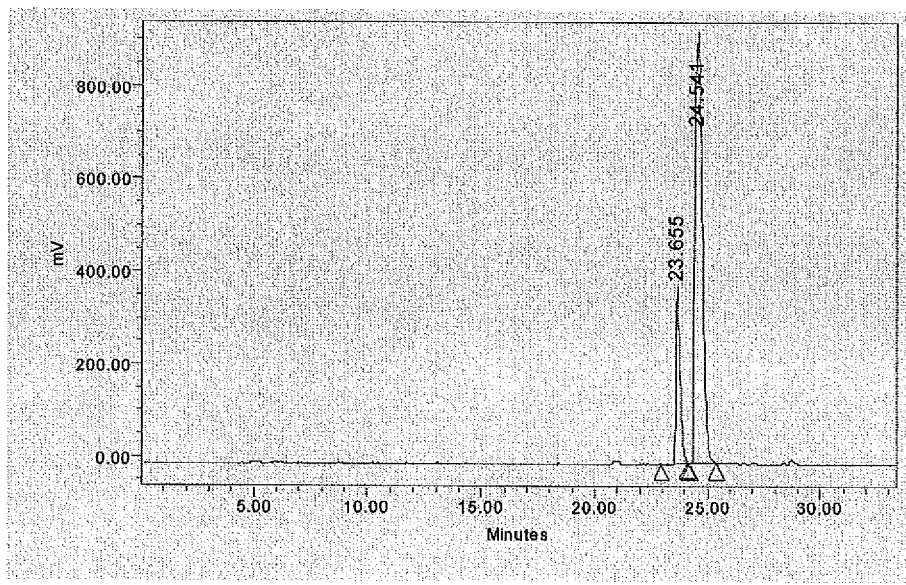
*Fig. 7B*
*Fig. 7*

METHODS TO INCREASE THE PHOTOSTABILITY OF DYES

FEDERALLY SPONSORED RESEARCH OR DEVELOPMENT

This invention was made with United States Government support under Grant Nos. GM 57464, GM 64346, and AG 15430 awarded by the National Institutes of Health, United States Department of Health and Human Services. The United States Government has certain rights in the invention.

FIELD OF THE INVENTION

The presently disclosed subject matter relates to fluorescent dyes and biosensors comprising said fluorescent dyes and methods of their use for detecting a target molecule and an activity or location of a target molecule within a living cell.

BACKGROUND

Merocyanine dyes are heterocyclic chromophores that can be used in a number of applications, for example, as photographic sensitizers, for non-linear optics, and in chemotherapy, to name a few. See, e.g., Chen et al., *J. Environ. Pathol. Toxicol. Oncol.* 25:217-222 (2006); Yow et al., *Toxicol. Lett.* 115:53-61 (2000); Zareba et al., *Biochim. Biophys. Acta.* 1722:51-59 (2005); Marder, *Chem. Commun.* 131-134 (2006); Marder et al., *J. Am. Chem. Soc.* 115:3006-3007 (1993); and Brooker et al., *J. Am. Chem. Soc.* 73:5332-5350 (1951). Merocyanine dyes also have been used as sensors of protein conformation and protein interactions in live-cell fluorescence imaging. See, e.g., Nalbant et al., *Science* 305: 1615-1619 (2004); Toutchkine et al., *J. Am. Chem. Soc.* 125: 4132-4145 (2003).

The efficacy of merocyanine dyes as components of biosensors depends not only on their fluorescence emission properties, but also on their photostability. In many cases, however, merocyanine fluorescent dyes degrade rapidly in light. Thus, the use of many merocyanine fluorescent dyes for live-cell imaging has been limited by rapid photobleaching of the dyes. Thus, there is a need in the art for merocyanine fluorescent dyes having improved photostability.

Further, ratiometric dyes having an excitation/emission wavelength that is dependent on solvent or protein environment are needed for live-cell imaging. A disadvantage of merocyanine dyes known in the art is that their excitation/emission wavelengths are not sufficiently solvent-dependent for use in live cell biosensors. This characteristic is thought to arise because the dyes are at the "cyanine limit." That is, they have an equal contribution of non-polar and polar resonance forms in the ground and excited states, which results in such dyes having similar dipole moments in the ground and excited states. As a consequence, the dyes' excitation and emission wavelengths are not solvent sensitive. Thus, there is a need in the art for merocyanine dyes having excitation and emission wavelengths that are solvent sensitive, and have sufficient photostability. The presently disclosed subject matter addresses, in whole or in part, these and other needs in the art.

SUMMARY

The presently disclosed subject matter demonstrates that the photostability of cyanine and merocyanine dyes can be enhanced compared to unsubstituted analogs by substituting an electron-accepting group at selected positions on the central polymethine chain. Without wishing to being bound to any one particular theory, the presently disclosed subject matter suggests that the observed enhancement is due to a reduction in reactivity of singlet oxygen with specific positions on the central polymethine chain. Accordingly, the presently disclosed subject matter demonstrates that such substitutions can be a general strategy for improving dye performance, for example, for detecting the presence or amount of one or more target molecules in a sample and in live-cell imaging applications.

In some embodiments, the presently disclosed subject matter provides a dye of Formula (I) or Formula (II):

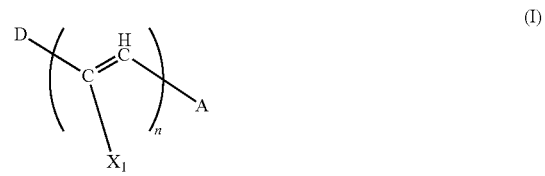

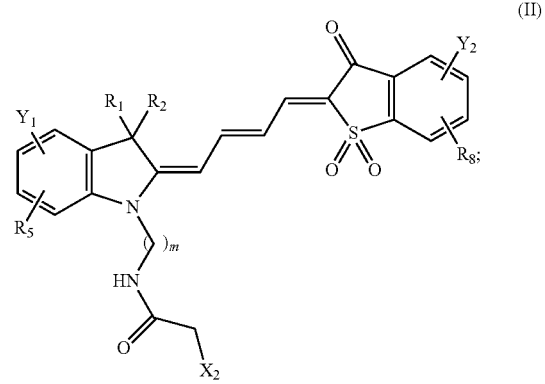

wherein:
n is an integer from 1 to 4;
m is an integer from 1 to 4;
each $X_1$ is independently an electron-accepting group selected from the group consisting of cyano, halogen, $CF_3$, $NO_2$, sulfonyl, —COOH, and combinations thereof;
$X_2$ is halogen;
D is selected from the group consisting of:

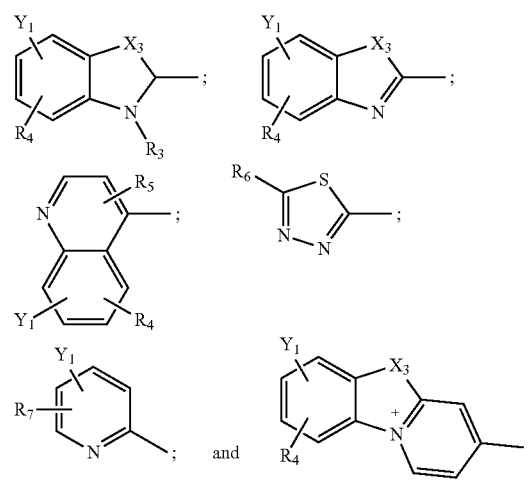

wherein:
each $X_3$ is independently selected from the group consisting of O, S, and $CR_1R_2$;

$R_1$, $R_2$, $R_3$, $R_5$, $R_6$, and $R_7$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, alkoxycarbonyl, alkyleneaminoalkyl, alkylenesulfate, —$(CH_2)_p$—$SO_3$, —$(CH_2)_p$—$N^+(CH_3)_2$—$(CH_2)_p$—NCS, and —$(CH_2)_p$—NH—CO—$CH_2$—$X_2$; wherein $X_2$ is halogen;

$R_4$ is selected from the group consisting of H, alkyl, substituted alkyl, hydroxyl, amino, nitro, alkoxyl, and hydroxyalkyl;

A is selected from the group consisting of:

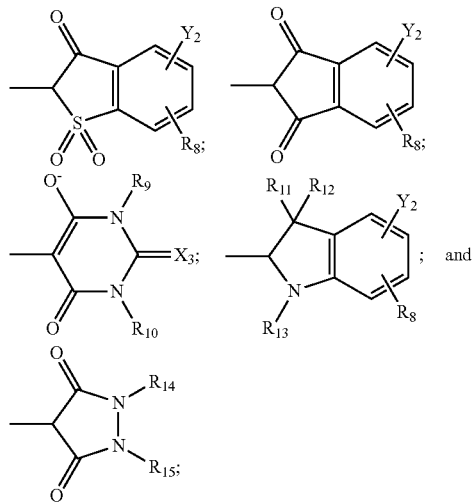

wherein:

$X_3$ is O, S, or $CR_1R_2$;

$R_8$ is selected from the group consisting of H, alkyl, substituted alkyl, hydroxyl, amino, nitro, alkoxyl, and hydroxyalkyl;

$R_9$, $R_{10}$, $R_{11}$, $R_{12}$, $R_{13}$, $R_{14}$, and $R_{15}$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, alkoxycarbonyl; and tolyl-acetonitrile;

$Y_1$ and $Y_2$ are each independently selected from the group consisting of H, —$NH_2$, —$SO_3^-$, —$(CH_2)_tOH$, —$(CH_2)_tNH_3^+X_2^-$; $CH_3CONH-$, $X_2CH_2CONH-$, $HO(CH_2)_2$—S—$CH_2CONH-$, $SuOCOCH_2OCH_2CON(CH_3)-$, —$CH_2$—NH—C(=O)—O—$(CH_3)_3$, —$(CH_2)_r$—$NH_2^+$—$(CH_2)_s$—$SO_3^-$, —$(CH_2)_r$—NH—C(=O)—$(CH_2)_s$—$X_2$, a succinimidyl ester, a hydroxysuccinimide, a maleimide, a haloacetyl, a pyridyl disulfide, a hydrazine, an ethyldiethylamino propylcarbodiimide,

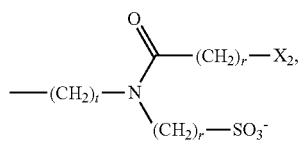

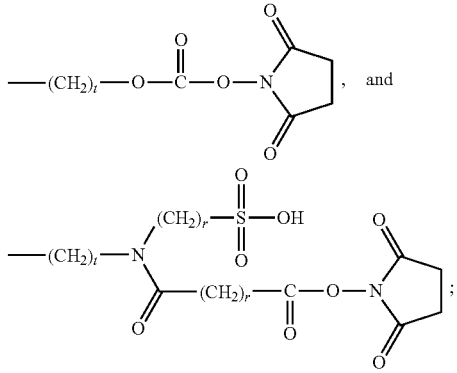

or a protecting group, including t-butoxycarbonyl and carbobenzoxy; wherein $X_2$ is halogen, and wherein each p, r, s and t is independently an integer from 1 to 8; and Su is succinimidyl ester; and salts thereof.

In some embodiments, the presently disclosed subject matter provides a biosensor comprising a dye of Formula (I) or Formula (II) and a binding member having a specific affinity for the target molecule, wherein the biosensor exhibits a detectable change in a fluorescence property during or after binding to the target molecule.

In some embodiments, the presently disclosed subject matter provides a method for determining the presence or amount of one or more target molecules in a sample, the method comprising: (a) providing a biosensor comprising a dye of Formula (I) or Formula (II); (b) contacting the biosensor with a sample suspected of containing one or more target molecules to bind the one or more target molecules, if present, to the binding member; (c) irradiating the sample suspected of containing one or more target molecules with electromagnetic radiation to induce the dye of Formula (I) or Formula (II) to fluoresce; and (d) detecting a fluorescence property of the dye of Formula (I) or Formula (II) to determine the presence or amount of one or more target molecules in the sample.

In some embodiments, the presently disclosed subject matter provides a method of detecting an activity or a location of one or more target molecule within a cell, the method comprising: (a) providing a biosensor comprising a dye of Formula (I) or Formula (II); (b) contacting the biosensor with a cell suspected of containing one or more target molecules to bind the one or more target molecules, if present, to the binding member; (c) irradiating the cell suspected of containing one or more target molecules with electromagnetic radiation to induce the dye of Formula (I) or Formula (II) to fluoresce; and (d) detecting one or more of: (i) a fluorescence property of the dye of Formula (I) or Formula (II); (ii) a change in a fluorescence property of the dye of Formula (I) or Formula (II); (iii) a location of a fluorescence of the dye of Formula (I) or Formula (II); and (iv) combinations thereof, to determine the an activity or location of one or more target molecules in the cell.

In some embodiments, the presently disclosed subject matter provides a method of detecting an interaction between an endogenous target molecule and a cellular entity, the method comprising: (a) providing a cell comprising an endogenous target molecule; (b) providing a probe comprising a binding member having a specific binding affinity for a binding site on the target molecule and a dye of Formula (I) or Formula (II); (c) observing a background fluorescence signal from the probe of step (b); (d) contacting the probe with the cell; and (e) detecting a change in fluorescence from the probe to indicate an interaction between the target molecule and the cellular entity.

In some embodiments, the presently disclosed subject matter provides a kit comprising a biosensor for detecting, monitoring or observing a target molecule, wherein the biosensor comprises a dye of Formula (I) or Formula (II) and a binding member having a specific affinity for the target molecule.

Certain embodiments of the presently disclosed subject matter having been stated hereinabove, which are addressed in whole or in part by the presently disclosed subject matter, other embodiments will become evident as the description proceeds when taken in connection with the accompanying Examples and Figures as best described herein below.

BRIEF DESCRIPTION OF THE DRAWINGS

Figure 1:
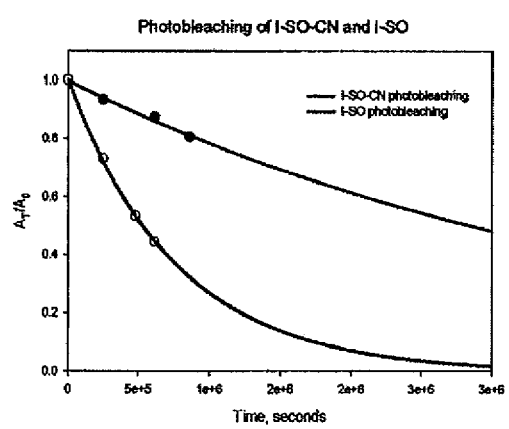
Figure 1:
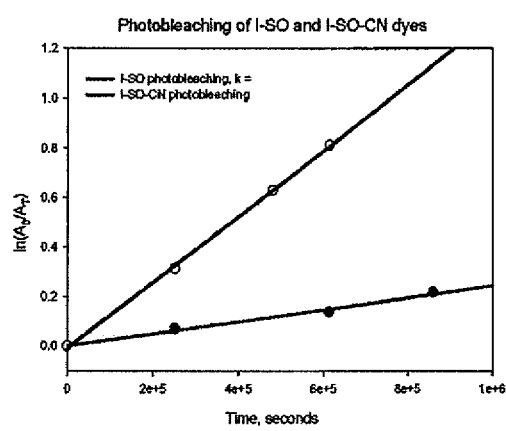
Figure 3:
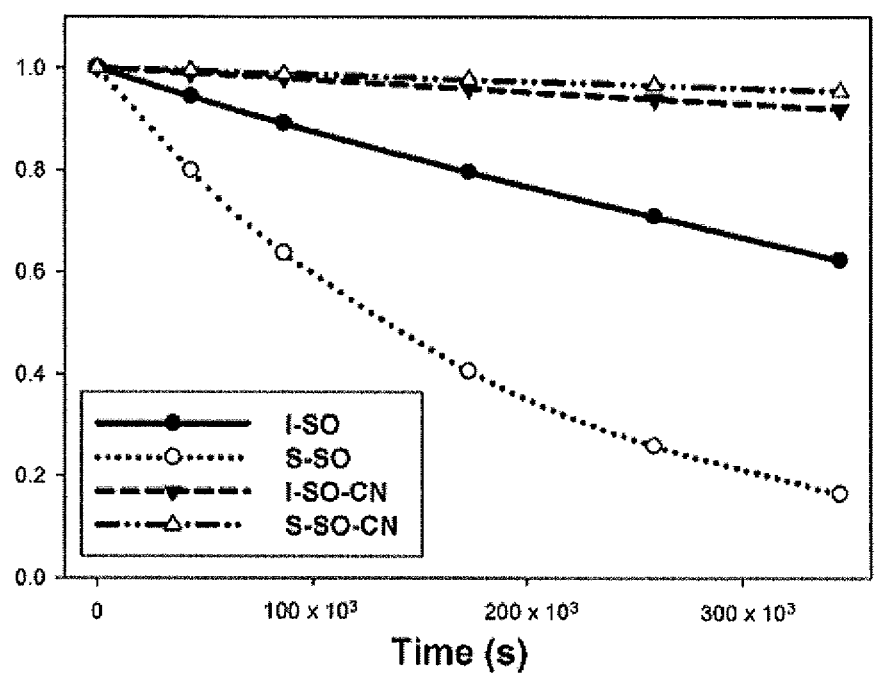
Figure 4:
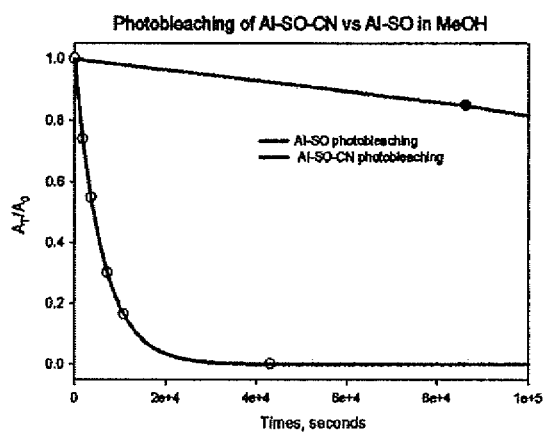
Figure 4:
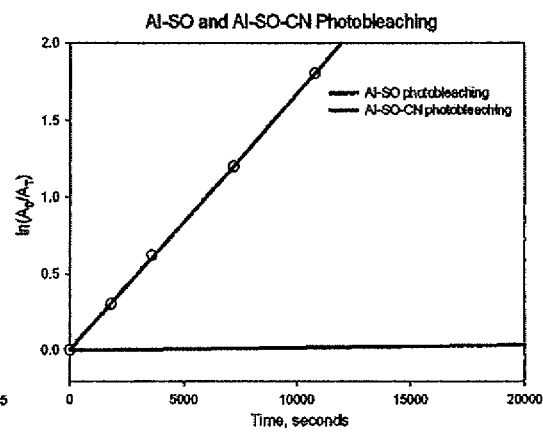
Figure 5:
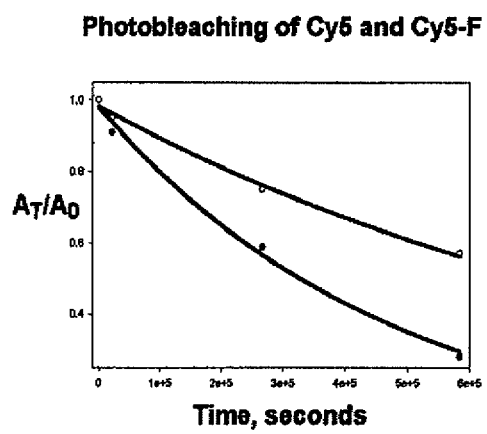
Figure 5:
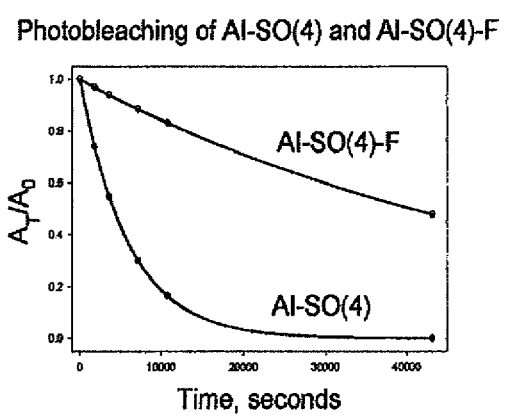
Figure 8:
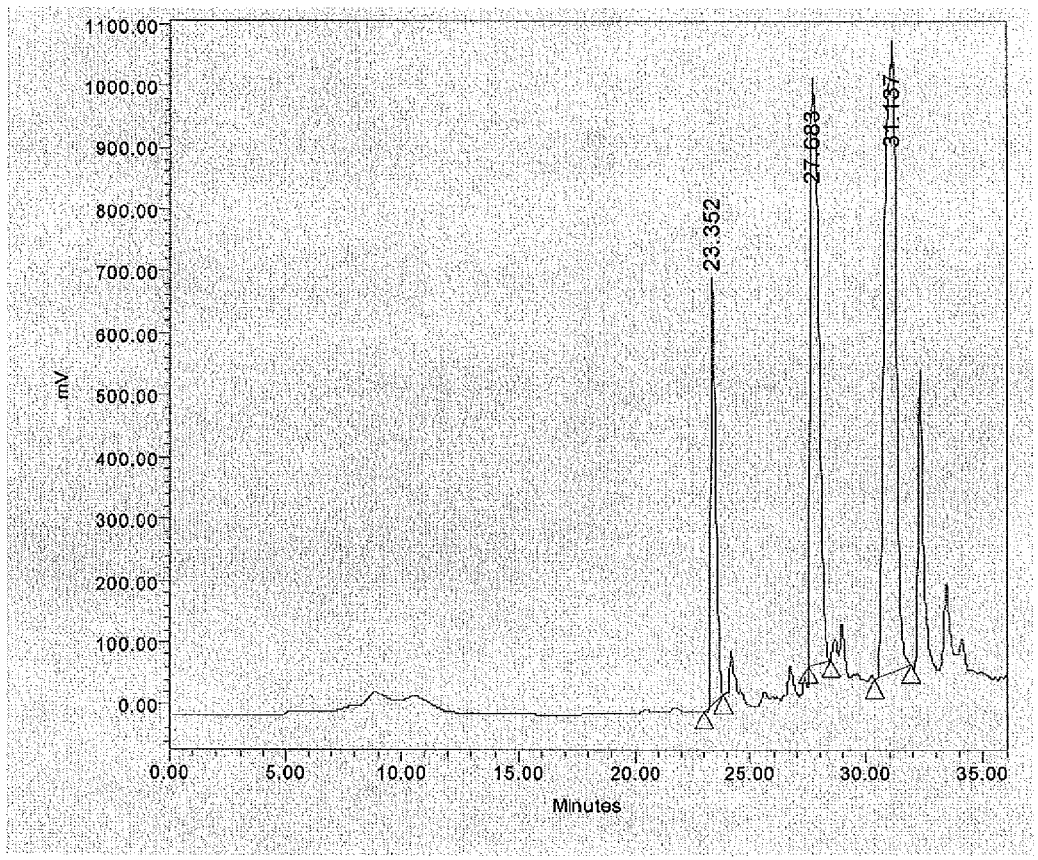
Figure 9:
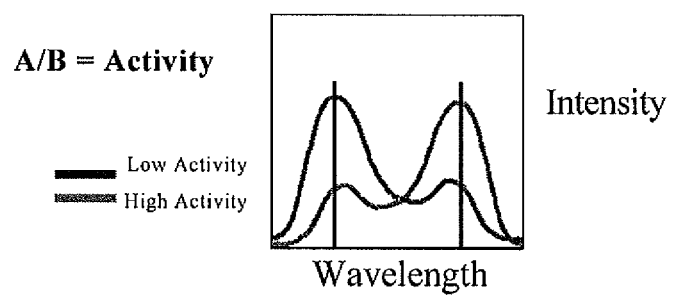
Figure 10:
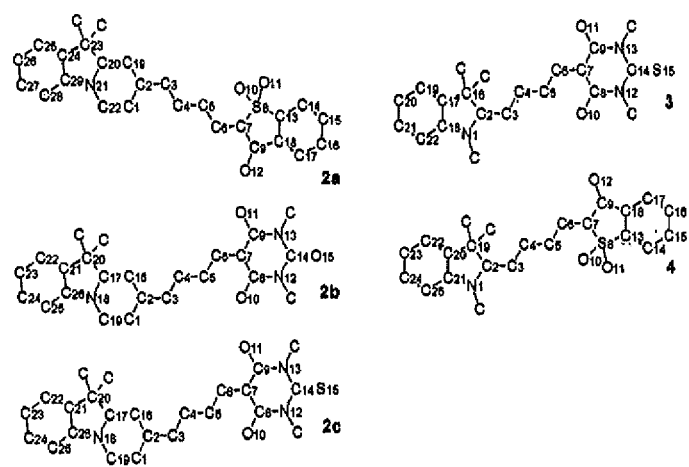
Figure 11:
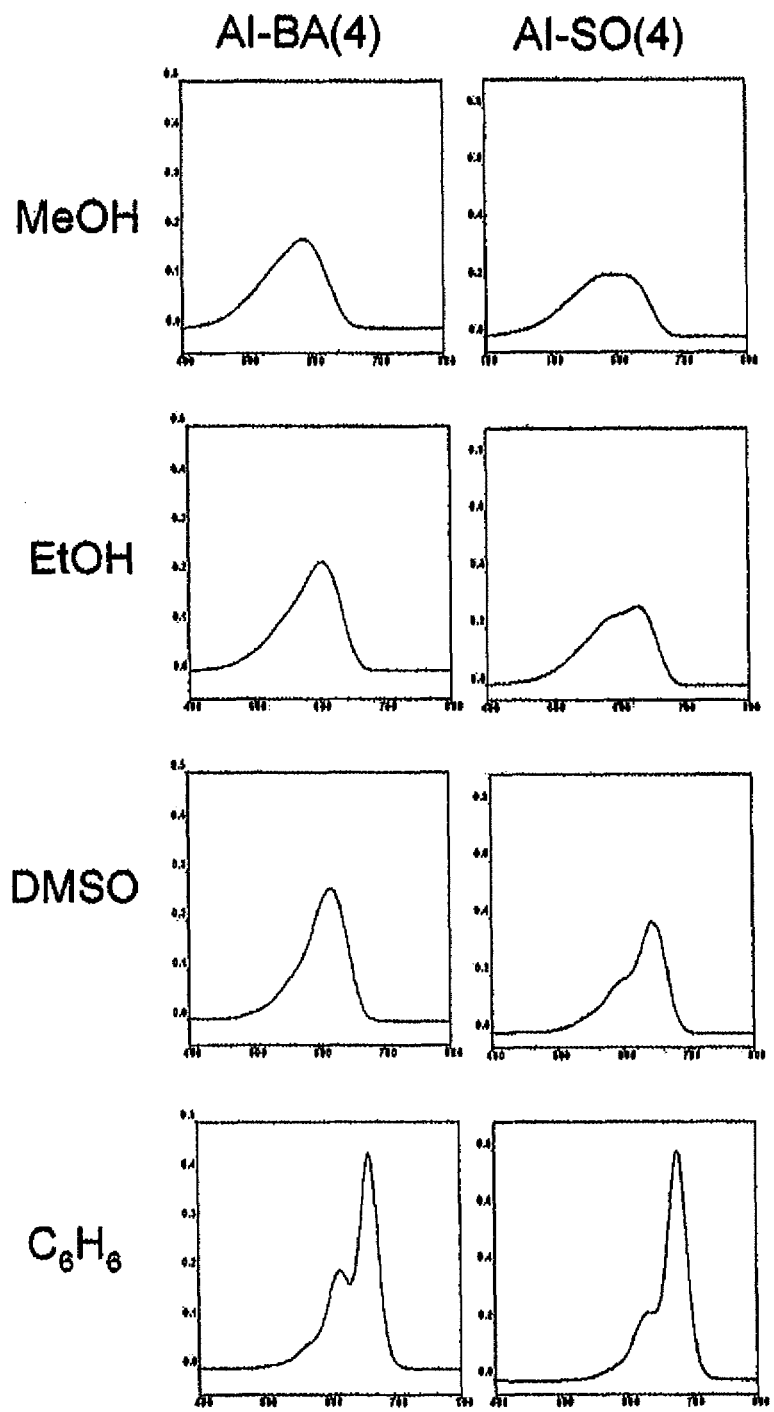
Figure 12:
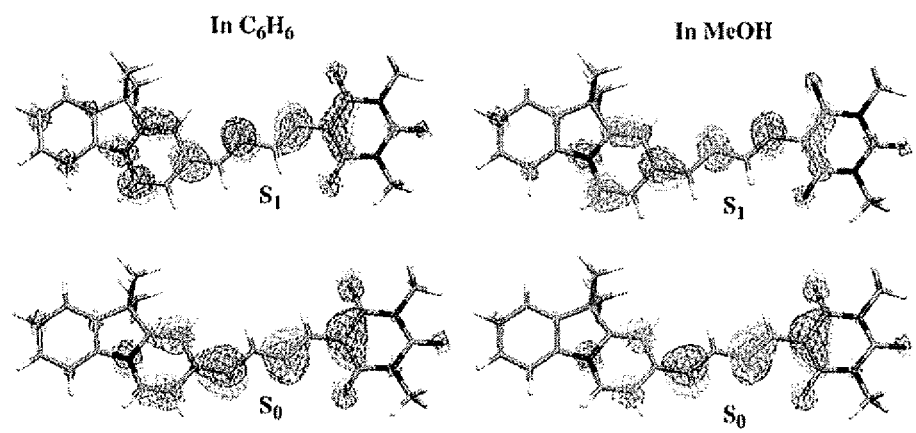
Figure 13:
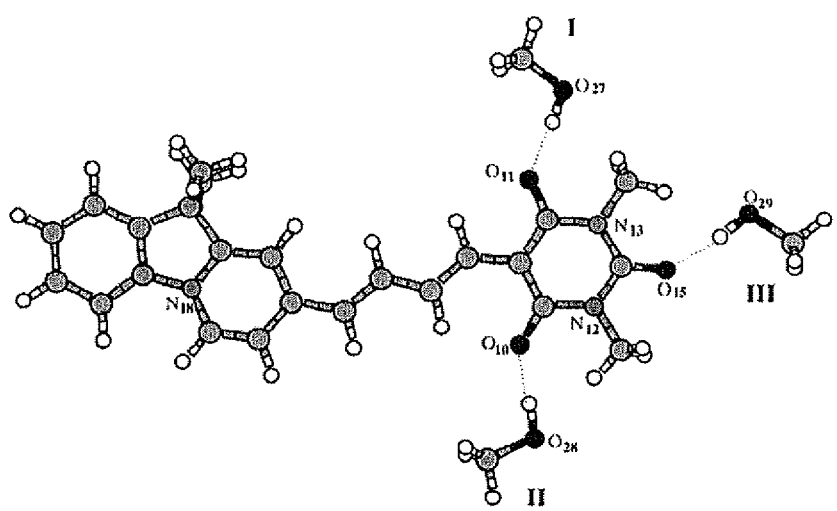
Figure 14:
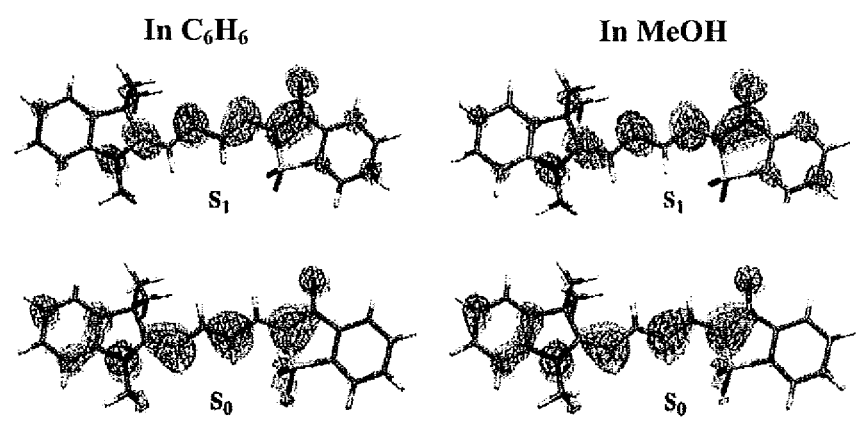
Figure 15:
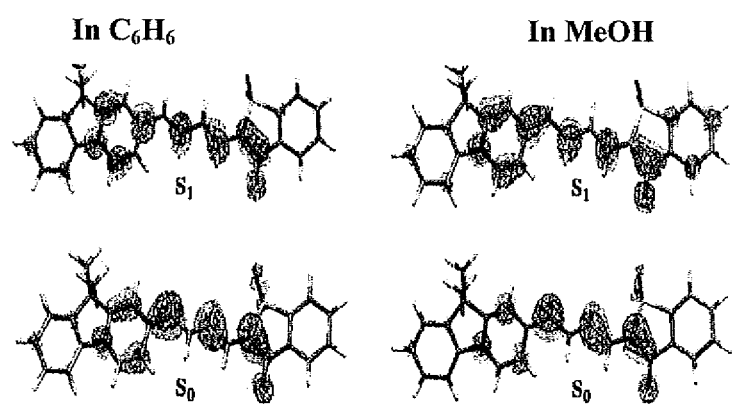
Figure 16:
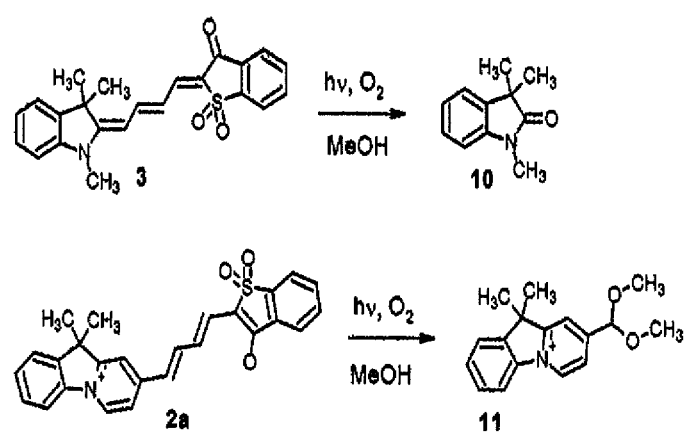
Figure 17:
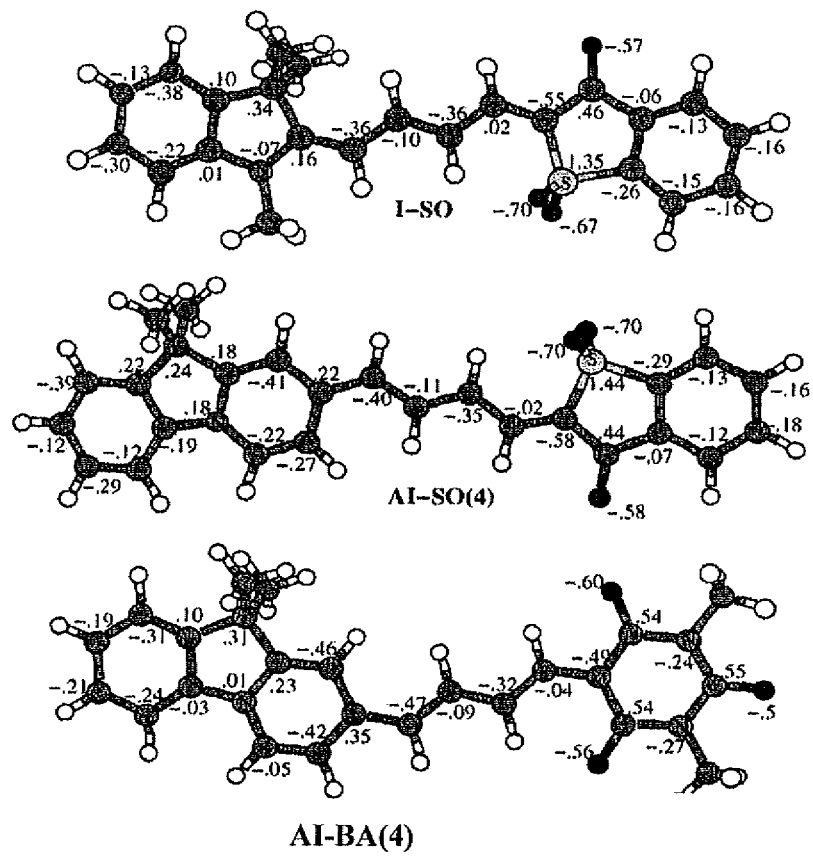

Having thus described the presently disclosed subject matter in general terms, reference will now be made to the accompanying Drawings, which are not necessarily drawn to scale, and wherein:

FIGS. 1A and 1B show photobleaching of I-SO and I-SO-CN. FIG. 1A shows the normalized absorbance decay vs. illumination time. FIG. 1B shows first-order kinetics of dye photobleaching;

FIGS. 2A-2D show photobleaching of S-SO and S-SO-CN. FIG. 2A shows the normalized absorbance decay vs. illumination time. FIG. 2B shows first-order kinetics of dye photobleaching; FIG. 2C shows first-order kinetics of S-SO photobleaching; FIG. 2D shows first-order kinetics of S-SO-CN photobleaching;

FIG. 3 is a graphical representation of the absorbance decay of I-SO, S-SO, I-SO-CN, and S-SO-CN dyes in MeOH upon illumination with light;

FIGS. 4A and 4B show the photobleaching of AI-SO and AI-SO-CN. FIG. 4A shows the normalized absorbance decay vs. illumination time. FIG. 4B shows the first-order kinetics of dye photobleaching;

FIGS. 5A and 5B show the photobleaching of fluorinated vs. unsubstituted dyes. FIG. 5A shows Cy5 and Cy5-F normalized absorbance decay vs. illumination time. FIG. 5B shows AI-SO and AI-SO-F normalized absorbance decay vs. illumination time;

FIGS. 6A and 6B are absorbance spectra illustrating the Methylene Blue-sensitized photobleaching of S-SO (FIG. 6A) and S-SO-CN (FIG. 6B), wherein each sample was irradiated with filtered tungsten lamp light ($\lambda$>630 nm) for 40 min[dye]=[Methylene Blue]=3.33 µM;

FIGS. 7A and 7B are HPLC traces of reaction intermediates (7) and (8) of the presently disclosed AI-BA-CN dyes;

FIG. 8 is an HPLC trace of reaction products including unreacted intermediate (8) and a final AI-BA-CN reaction product;

FIG. 9 shows an example of ratio imaging between two spectra A and B;

FIG. 10 shows geometry-optimized structures and numbering convention for representative merocyanine dyes;

FIG. 11 shows representative absorbance spectra of AI-BA (4) and AI-SO(4) in methanol (MeOH), ethanol (EtOH), DMSO, and benzene ($C_6H_6$);

FIG. 12 shows molecular orbital plots for the electron in the HOMO of the ground state ($S_0$) and the $\pi \rightarrow \pi^*$ promoted electron in the first excited singlet state of AI-BA(4) in $C_6H_6$ and in MeOH;

FIG. 13 shows three possible positions of the explicit $CH_3OH$ molecules H-bonding to AI-BA(4) in MeOH solution;

FIG. 14 shows molecular orbital plots for the electron in HOMO of the $S_0$ state and the $\pi \rightarrow \pi^*$ promoted electron in the $S_1$ state of I-SO in $C_6H_6$ and in MeOH;

FIG. 15 shows molecular orbital plots for the electron in HOMO of the $S_0$ state and the $\pi \rightarrow \pi^*$ promoted electron in the $S_1$ state of AI-SO(4) in $C_6H_6$ and in MeOH;

FIG. 16 shows products of photobleaching reactions of representative merocyanine dyes; and FIG. 17 shows atomic ESP charges of the ground state I-SO, AI-SO(4) and AI-BA(4) dyes in MeOH.

DETAILED DESCRIPTION

The presently disclosed subject matter now will be described more fully hereinafter with reference to the accompanying Figures, in which some, but not all embodiments of the presently disclosed subject matter are shown. Many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

I. Cyanine and Merocyanine Dyes Having Improved Photostability

Cyanine and merocyanine dyes can be used as fluorescent labels for biomolecules, such as proteins or antibodies, for histochemical studies or immunobased assays. Such dyes can be attractive for use as fluorophores due, in part, to their wide range of available wavelengths, large molar extinction coefficients, and high quantum yields. One drawback, however, to cyanine and merocyanine fluorescent dyes, and other organic fluorescent dyes known in the art, is their tendency to undergo photobleaching.

The presently disclosed subject matter provides a method for improving the photostability of cyanine and merocyanine dyes. More particularly, the presently disclosed subject matter demonstrates that placing electron-withdrawing groups (also referred to herein as "electron-accepting groups") at selected positions on the polymethine chain reduces photobleaching of cyanine and merocyanine dyes. Accordingly, in some embodiments, the presently disclosed approach includes attaching an electron-withdrawing substituent, such as a cyano group, a halogen atom, or other suitable electron-withdrawing group, at positions on the polymethine chain that are susceptible to attack by oxygen. Such groups decrease the electron density on the substituted carbon atom and subsequently reduce the rate of singlet oxygen attack.

Further, because of the sensitivity of the fluorescence intensity and wavelength of merocyanine dyes to solvent polarity and other characteristics of the dye environment, the presently disclosed merocyanine dyes can be used as sensors, e.g., a biosensor, of protein activation, protein-protein binding, and protein conformational changes.

A. Photodegradation Pathway of Merocyanine Dyes

The major photodegradation path of merocyanine dyes is thought to be oxidation of the dyes by photogenerated singlet oxygen. See Toutchkine et al., *J. Am. Chem. Soc.* 125:4132-4145 (2003). A general schematic representation of the photochemical production of singlet oxygen ($^1O_2$) from fluorescent dyes in situ is provided in Scheme 1.

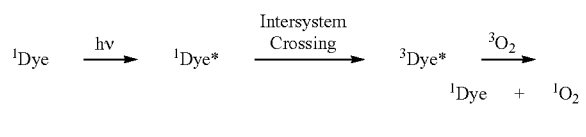

Scheme 1. Photochemical Production of Singlet Oxygen ($^1O_2$) from Fluorescent Dyes The ground (triplet) state of oxygen ($^3O_2$) is an effective quencher of the triplet excited state of the merocyanine dyes (3Dye*), with a rate of about $10^9$ L/mol*s. See Wilkinson and Abdel-Shaft, *J. Phys. Chem. A* 101:5509-5516 (1997). Triplet-triplet energy transfer results in the production of highly reactive electrophilic singlet oxygen ($^1O_2$) that reacts with the ground state of the dye, thereby degrading the fluorophore.

To elucidate the mechanism of the photooxidation of representative merocyanine dyes, methanolic solutions of the dyes I-SO and S-SO were photobleached and product formation was measured by liquid chromatograph/mass spectrometry (LC-MS). As shown in Scheme 2, analysis of the reaction mixtures revealed that the major product formed was either an oxindole (1) (e.g., 1,3,3-trimethyl-1,3-dihydro-2H-indol-2-one) or a benzothiazolone (2) (e.g., 3-ethyl-1,3-benzothiazol-2(3H)-one).

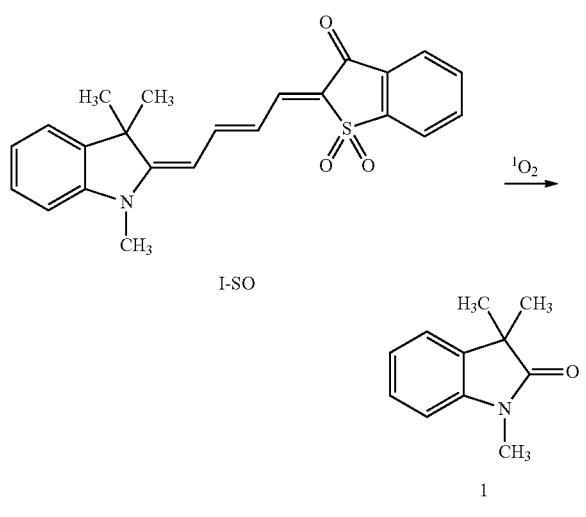

I-SO

1

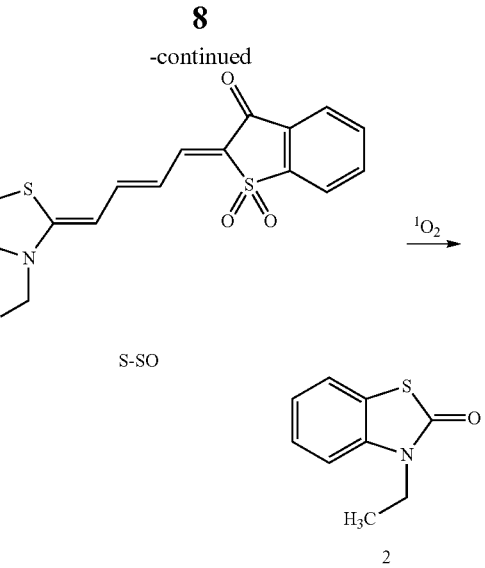

S-SO

2

Scheme 2. Reaction Products from the Photooxidation of I-SO and S-SO Dyes

The presence of these products is indicative of the attack of singlet oxygen on the α-carbon atom of the polymethine chain. For example, mechanisms for the photooxidation of I-SO and S-SO are provided in Scheme 3 and Scheme 4, respectively. Without wishing to be bound to any one particular theory, the formation of these products can be attributed to the initial attack of singlet oxygen on the most nucleophilic α-carbon of the central polymethine chain with formation of a dioxetane (4). As a strong electrophilic reagent, singlet oxygen attacks the carbon atoms with the highest atomic charge, i.e., the α-carbon of the polymethine chain. The zwitterionic intermediate (3) is thought to be the first addition product, as was reported in singlet oxygen reactions with enamines See Saito et al., *J. Am. Chem. Soc.* 101:7332-7338 (1979). The cleavage of the dioxetane (4) results in the formation of two carbonyl fragments. Stable products, e.g., a benzothiazolone (2) or an oxindole (1), can then be detected in the reaction mixture. The proposed mechanism suggests that the rate determining step of the dye oxidation reaction includes charge transfer from the α-carbon atom to a singlet oxygen molecule. See Dewar and Thiel, *J. Am. Chem. Soc.* 97:3978-3986 (1975).

Scheme 3. Schematic Representation of the Mechanism of the Photooxidation of I-SO.

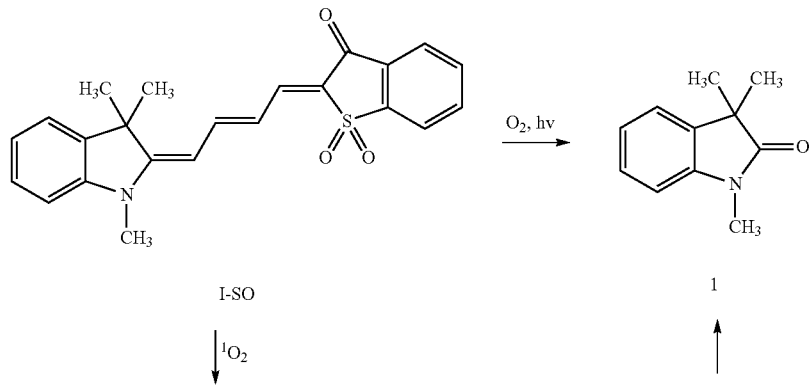

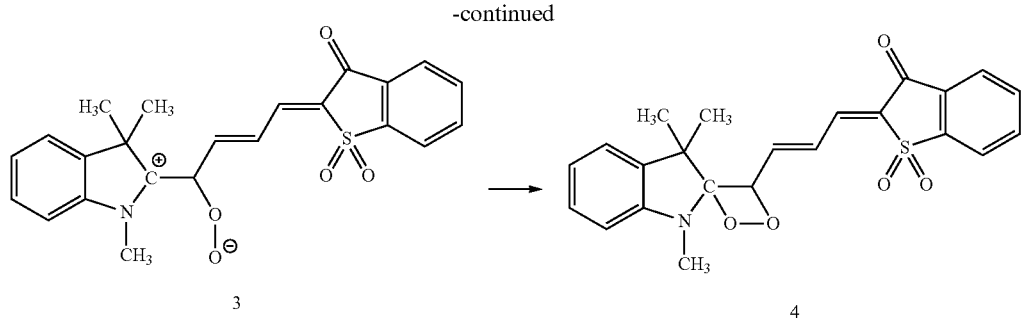

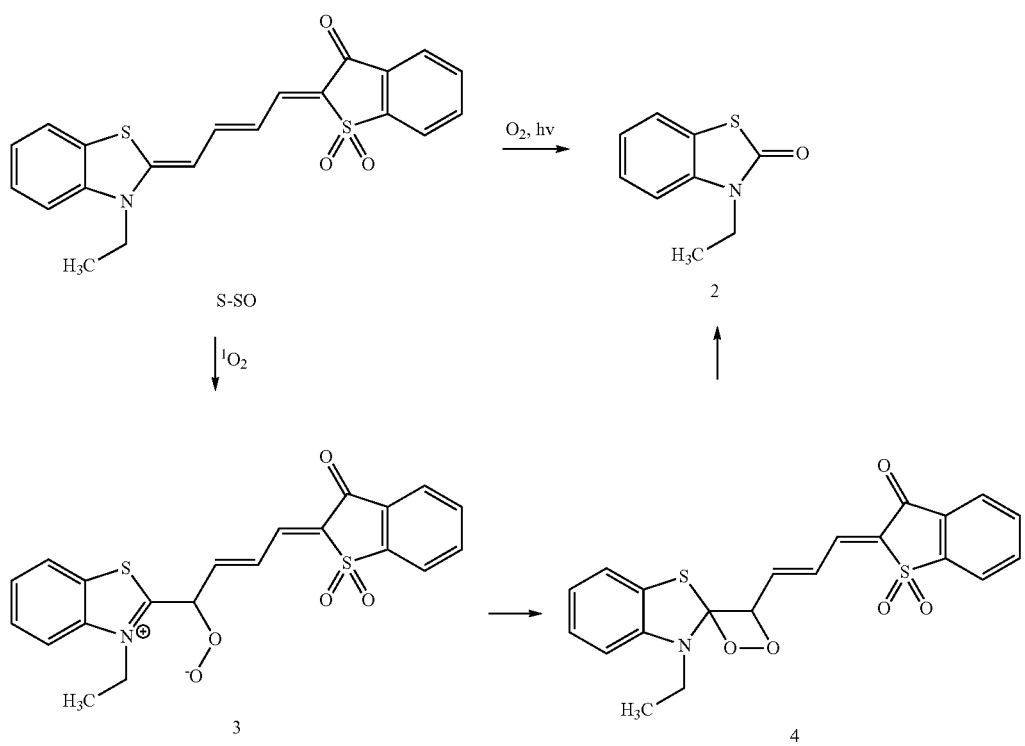

Scheme 4. Schematic Representation of the Mechanism of the Photooxidation of S-SO.

The presently disclosed subject matter demonstrates that this reaction can be inhibited by the substitution of an electron-accepting group on the α-carbon of the central polymethine chain to partially remove electron density therefrom.

B. Dyes Having Improved Photostability

In some embodiments, the presently disclosed subject matter provides a cyanine or merocyanine dye having the general Formula (I) or Formula (II):

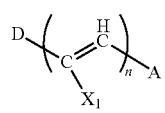

(I)

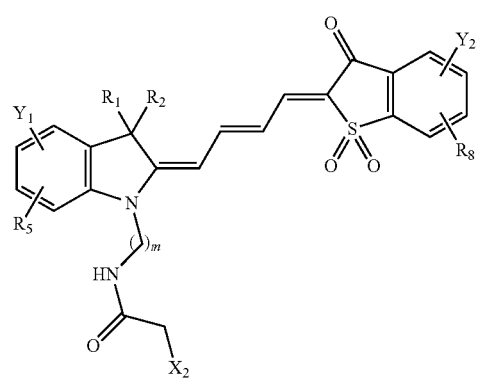

Dyes of Formula (I) or Formula (II) have a central polymethine chain, wherein, in dyes of Formula (I), the polymethine chain is substituted with one or more electron-accepting groups, e.g., $(X)_m$, at selected positions, i.e., on selected carbon atoms, of the chain. Substitution in the polymethine chain of merocyanine or cyanine dyes with an electron-accepting group, for example, a cyano group or a halogen atom, such as fluorine, results in an increase in photostability. Other electron-accepting groups include, but are not limited to $CF_3$, $NO_2$, sulfonyl, carboxyl (—COOH), which also are suitable for use with the presently disclosed subject matter. The increase in photostability is the result of a lower reactivity of the substituted dyes toward singlet oxygen. Electron-accepting groups reduce electron density on the double bond system of the polymethine chain and reduce the reaction rate of the dyes with singlet oxygen.

The dyes of Formula (I) or Formula (II) also comprise a "donor" (D) and an "acceptor" (A). The donor (D) and acceptor (A) each comprise a hydrocarbon ring system, wherein the ring systems comprise radicals having, for example, 6 to 20 carbon atoms, and wherein the radical is derived by removing one hydrogen atom from a single carbon atom of the parent ring system. In some embodiments, the parent ring system comprises at least one aromatic ring system. Aromatic ring systems suitable for use with the presently disclosed subject matter include, but are not limited to, radicals derived from: benzene, i.e., a phenyl radical; biphenyls; heteroaromatic rings including heteroatoms, such as nitrogen, sulfur, and/or oxygen; fused ring systems, such as fluorene, naphthalene, anthracene, and the like; heteroaromatic fused ring systems, including fused ring systems having heteroatoms such as nitrogen, sulfur, and/or oxygen. Non-limiting examples of aromatic ring systems suitable for use with the presently disclosed subject matter include indole, dihydroindole, e.g., indoline, benzothiophene, dihydrobenzothiophene, benzothiazole, pyrimidine, fluorene, 10H-pyrido[1,2-a]indolium, and analogs or derivatives thereof.

Without wishing to be bound to any one particular theory, it is believed that the inclusion of an additional aromatic ring structure to the pyridine ring of a merocyanine dye, e.g., to form a 10H-pyrido[1,2-a]indolium fused-ring structure, stabilizes the polar, zwitterionic form of the dye in the ground state because of a restored aromaticity of the pyridine ring. Dyes having such a fused-ring structure exhibit a shift in $\lambda_{max}$ relative dyes merocyanine dyes known in the art and exhibit strongly solvent sensitive absorption and emission wavelengths. Such dyes also exhibit high fluorescence quantum yields, even in polar solvents.

More particularly, in some embodiments, the presently disclosed subject matter provides a dye of Formula (I) or Formula (II):

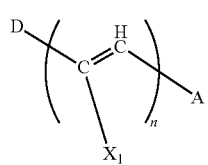
(I)

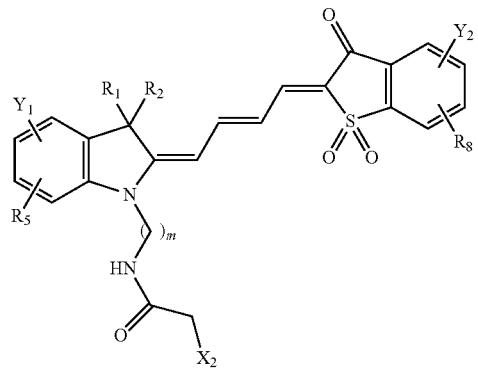
(II)

wherein:

n is an integer from 1 to 4;

m is an integer from 1 to 4;

each $X_1$ is independently an electron-accepting group selected from the group consisting of cyano, halogen, $CF_3$, $NO_2$, sulfonyl, —COOH, and combinations thereof;

$X_2$ is halogen;

D is selected from the group consisting of:

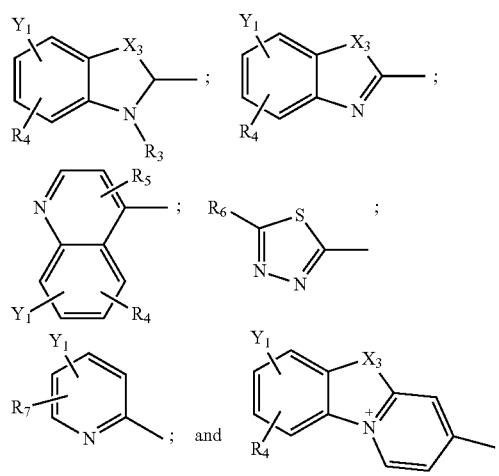

wherein:

each $X_3$ is independently selected from the group consisting of O, S, and $CR_1R_2$;

$R_1$, $R_2$, $R_3$, $R_5$, $R_6$, and $R_7$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, alkoxycarbonyl, alkyleneaminoalkyl, alkylenesulfate, $-(CH_2)_p-SO_3$, $-(CH_2)_p-N^+(CH_3)_2-(CH_2)_p-NCS$, and $-(CH_2)_p-NH-CO-CH_2-X_2$; wherein $X_2$ is halogen;

$R_4$ is selected from the group consisting of H, alkyl, substituted alkyl, hydroxyl, amino, nitro, alkoxyl, and hydroxyalkyl;

A is selected from the group consisting of:

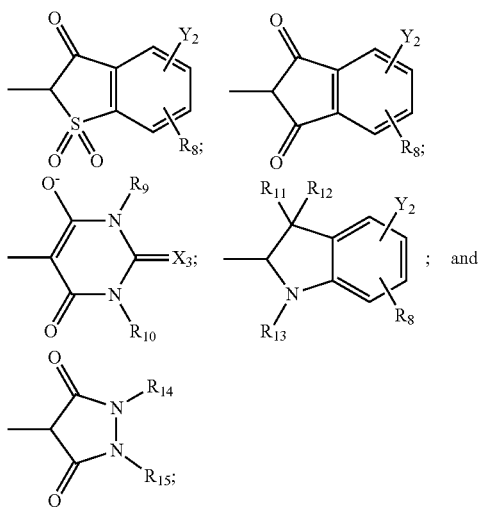

wherein:
$X_3$ is O, S, or $CR_1R_2$;
$R_8$ is selected from the group consisting of H, alkyl, substituted alkyl, hydroxyl, amino, nitro, alkoxyl, and hydroxyalkyl;
$R_9$, $R_{10}$, $R_{11}$, $R_{12}$, $R_{13}$, $R_{14}$, and $R_{15}$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, alkoxycarbonyl; and tolyl-acetonitrile;
$Y_1$ and $Y_2$ are each independently selected from the group consisting of H, $-NH_2$, $-SO_3^-$, $-(CH_2)_rOH$, $-(CH_2)_rNH_3^+X_2^-$; $CH_3CONH-$, $X_2CH_2CONH-$, $HO(CH_2)_2-S-CH_2CONH-$, $SuOCOCH_2OCH_2CON(CH_3)-$, $-CH_2-NH-C(=O)-O-(CH_3)_3$, $-(C_2)_t-NH_2^+-(CH_2)_s-SO_3^-$, $-(CH_2)_t-NH-C(=O)-(CH_2)_s-X_2$, a succinimidyl ester, a hydroxysuccinimide, a maleimide, a haloacetyl, a pyridyl disulfide, a hydrazine, an ethyldiethylamino propylcarbodiimide,

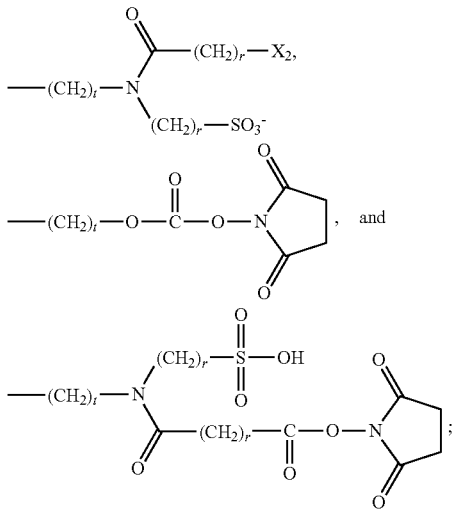

or a protecting group, including t-butoxycarbonyl and carbobenzoxy; $X_2$ is halogen; and wherein each p, r, s and t is independently an integer from 1 to 8; and Su is succinimidyl ester; and salts thereof.

In some embodiments of the dye of Formula (I), D is selected from the group consisting of:

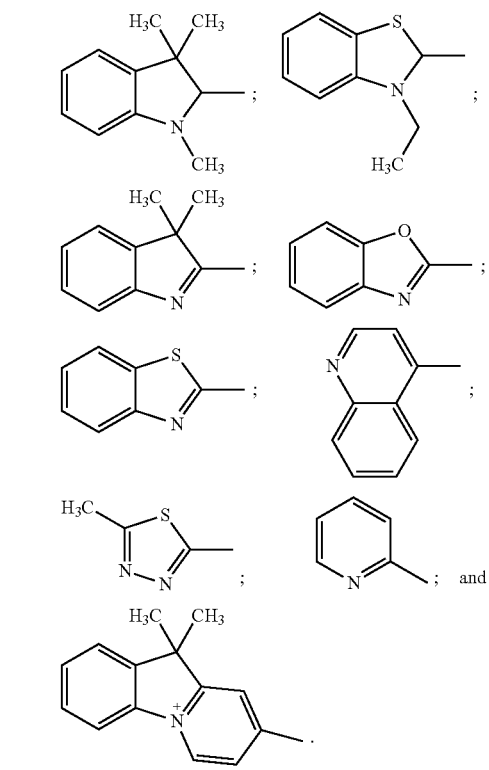

In some embodiments of the dye of Formula (I), A is selected from the group consisting of:

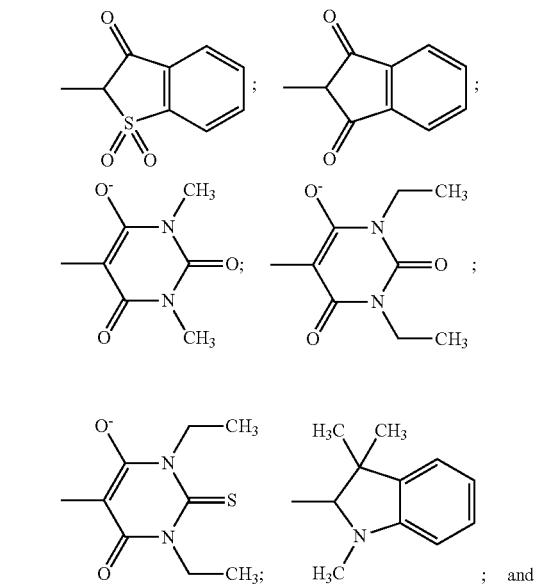

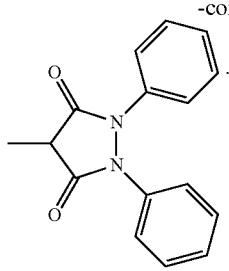

In some embodiments of the dye of Formula (I), $X_1$ is selected from the group consisting of cyano and fluorine.

Representative structures and nomenclature of the presently disclosed dyes of Formula (I) are provided in Table 1. Such dyes are named for the combination of donor and acceptor heterocyclic ring structures comprising their structure (donors: I=indolenine, S=benzothiazole, O=benzoxazole, AI=a 10H-pyrido[1,2-a]indolium radical; acceptors: SO=benzothiophen-3-one-1,1-dioxide, TBA=thiobarbituric acid). The number in parentheses indicates the number of methines in the central polymethine chain. For example, the dye designated herein as AI-SO(4) has 4 carbon atoms in the central polymethine chain, i.e., two methine groups.

TABLE 1

Representative Structures and Nomenclature of Dyes of Formula (I).

I-SO

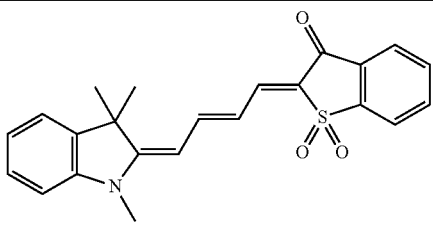

I-SO-CN

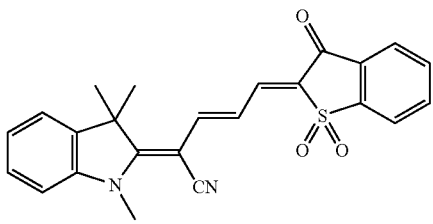 [SMILES: CN1/C(=C(C#N)/C=C/C=C2/C(=O)c3ccccc3S2(=O)=O)C(C)(C)c2ccccc21]

I-BA

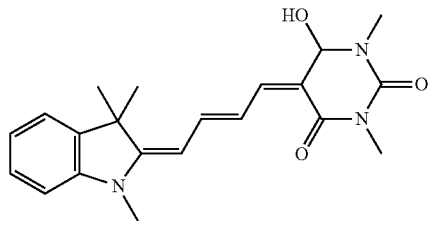 [SMILES: CN1C(=O)\C(=C/C=C/C=C2/N(C)c3ccccc3C2(C)C)C(O)N(C)C1=O]

I-BA-CN

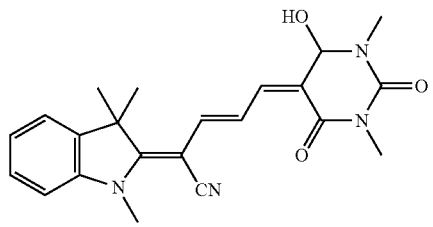 [SMILES: CN1C(=O)\C(=C/C=C/C(C#N)=C2/N(C)c3ccccc3C2(C)C)C(O)N(C)C1=O]

TABLE 1-continued

Representative Structures and Nomenclature of Dyes of Formula (I).

I-TBA

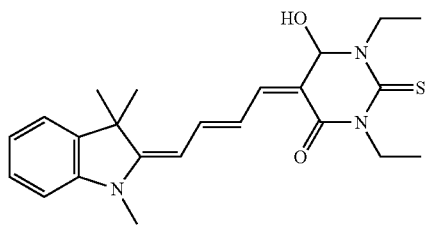 [SMILES: CCN1C(=O)\C(=C/C=C/C=C2/N(C)c3ccccc3C2(C)C)C(O)N(CC)C1=S]

I-TBA-CN

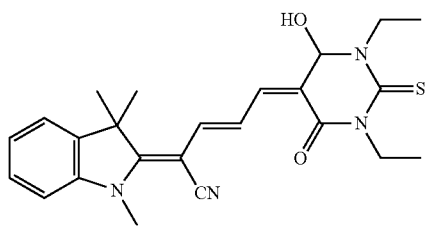 [SMILES: CCN1C(=O)\C(=C/C=C/C(C#N)=C2/N(C)c3ccccc3C2(C)C)C(O)N(CC)C1=S]

S-SO

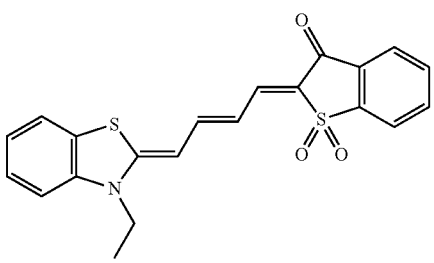 [SMILES: CCN1/C(=C/C=C/C=C2/C(=O)c3ccccc3S2(=O)=O)Sc2ccccc21]

S-SO-CN

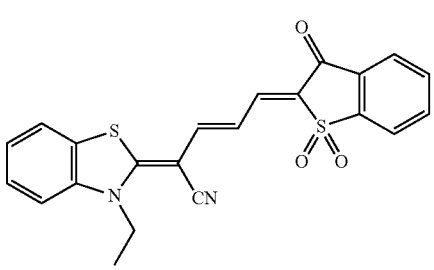 [SMILES: CCN1/C(=C(C#N)/C=C/C=C2/C(=O)c3ccccc3S2(=O)=O)Sc2ccccc21]

S-BA

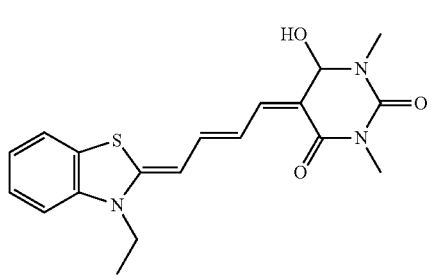 [SMILES: CCN1/C(=C/C=C/C=C2\C(=O)N(C)C(=O)N(C)C2O)Sc2ccccc21]

S-BA-CN

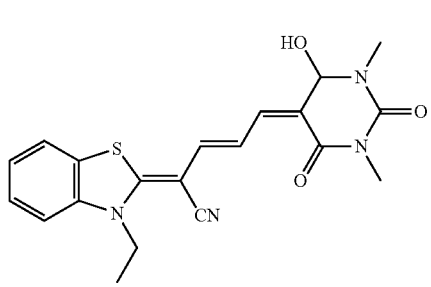 [SMILES: CCN1/C(=C(C#N)/C=C/C=C2\C(=O)N(C)C(=O)N(C)C2O)Sc2ccccc21]

US 8,835,632 B2
TABLE 1-continued
Representative Structures and Nomenclature of Dyes of Formula (I).
S-TBA
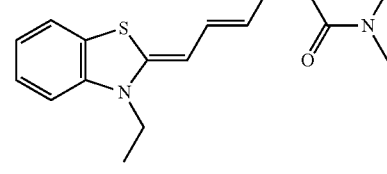
S-TBA-CN
S-SO-CN-F
AI-SO
AI-SO-CN
AI-BA
AI-BA-CN
TABLE 1-continued
Representative Structures and Nomenclature of Dyes of Formula (I).
AI-TBA
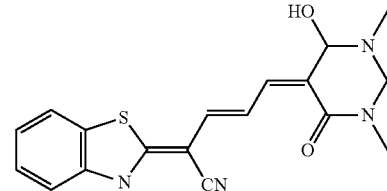
AI-TBA-CN
AI-SO
AI-SO-F
AI-SO-CN-F
Cy5
Cy5-F In some embodiments, the dye of Formula (II) has the following structure:

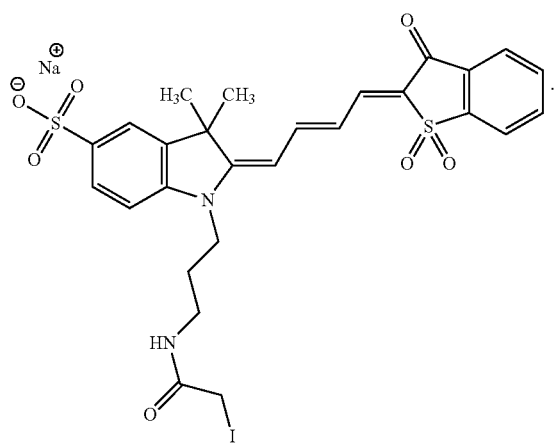 [SMILES: CC1(C)\C(=C/C=C/C=C2/C(=O)c3ccccc3S2(=O)=O)N(CCCNC(=O)CI)c2ccc(S(=O)(=O)[O-])cc21 ; [Na+]]

The presently disclosed dyes can be many times brighter than other dyes used previously to study antibody-antigen and other protein-protein interactions in vitro. See, for example, Renard et al., *J. Mol. Biol.* 326:167-175 (2003); Sloan and Hellinga, *Protein Eng.*, 11:819-823 (1998); Iwatani et al., *Biochemistry* 38:10318-10323 (1999). The quantum yield of the presently disclosed dyes can be high, for example, in hydrophobic environments. For example, for many of the presently disclosed dyes in a hydrophobic environment or solvent, the quantum yield, in some embodiments, is greater than about 0.4, in some embodiments, greater than about 0.5, in some embodiments, greater than about 0.6, in some embodiments, greater than about 0.7, in some embodiments, greater than about 0.8, and, in some embodiments, greater than about 0.9. Further, the combination of a high extinction coefficient and a high quantum yield, as exhibited by some embodiments of the presently disclosed dyes, can provide a strong direct signal from biosensors comprising such dyes. Such high quantum yields and extinction coefficients can allow detections from very small amounts of biosensor, minimally perturbing the biological activity of the endogenous proteins being studied, and enabling high resolution kinetic studies by obtaining many images before photo-bleaching occurs.

In some embodiments, the "donor" and/or "acceptor" ring structures, e.g., "D" and/or "A," of a dye of Formula (I) or Formula (II) can include one or more substituent groups. Such ring systems comprising one or more substituent groups can be referred to as "derivatives" of the parent compound, i.e., a derivative of a dye of Formula (I). As used herein, a "derivative" refers to a chemical compound that is derived from or obtained from a parent compound and contains essential elements of the parent compound, but typically has one or more different functional groups. Such functional groups can be added to a parent compound, for example, to improve the molecule's solubility, absorption, biological half life, fluorescent properties, and the like, or to decrease the toxicity of the molecule, eliminate or attenuate any undesirable side effect of the molecule, and the like.

In some embodiments, the substitution of one or more functional groups on the donor and/or acceptor ring structure can improve the solubility of the dye in particular solvents, such as water. For example, as described in U.S. Patent Application Publication No. 2006/0029946 to Hahn, the presently disclosed dyes can be designed to have enhanced water solubility by attaching substituent groups on the ring structure that sterically block aggregation without unduly increasing hydrophobicity. Under some circumstances, this approach can be more desirable than enhancing water solubility using highly charged groups that can affect protein interaction.

Planar merocyanine dyes known in the art are thought to form non-fluorescent hydrogen conjugates in water, thereby reducing the exposure of their hydrophobic surfaces to water. Such aggregation can be decreased by incorporating bulky, non-planar substituents with tetragonal geometry in the aromatic rings to make stacking unfavorable. This approach can provide dyes with good water solubility while retaining substantial hydrophobic character. For example, in the presently disclosed I-SO and AI-SO dyes, the out-of-plane substituent groups can be two alkyl, e.g., methyl, groups bound to a carbon atom of an aromatic ring, or two oxygen atoms bound to a sulfur atom of a heterocyclic ring structure. To this end, the presently disclosed dyes can have one or more groups arranged in, for example, a tetragonal geometry from rings of the dye. In many cases, the substituent groups include groups with one or more carbons providing steric hindrance to ring stacking, and/or polar to weak ionic character to enhance water solubility.

Accordingly, the substituents on one or more ring structures of the dyes of Formula (I) or Formula (II) can be any functional group that inhibits stacking of the aromatic rings and/or enhances water solubility. Such substituent groups can provide steric hinderance to ring stacking, thereby inhibiting aggregation, without reducing water solubility of the dye. In some embodiments, the substituent group can have an aliphatic nature, e.g., a straight-chain or branched alkyl group. In some embodiments, the substituent group can have a polar or weakly charged character. Generally, the presently disclosed dyes can be derivatized with side chains to prevent aggregation, improve solubility, affect interactions with proteins, and enable covalent attachment to proteins.

In some embodiments, the presently disclosed dyes of Formula (I) or Formula (II) are environmentally sensitive. As used herein, the term "environmentally sensitive" in relation to a dye of Formula (I) or Formula (II) refers to a dye in which a fluorescence signal from the dye changes when the dye is exposed to a change in environment, for example, a hydrophobicity, hydrogen bonding, polarity, or conformational change. Thus, a fluorescence signal from a dye of Formula (I) or Formula (II) detectably changes upon exposure to a change in solvent, change in hydrogen bonding, change in the hydrophobicity of the environment, changed polarity or polarization, or change affecting the conformation of the dye. In one embodiment, the fluorescence signal from the dye of Formula (I) or Formula (II) increases when the dye is exposed to an environment that is more hydrophobic. In another embodiment, the fluorescence signal provided by the dye of Formula (I) or Formula (II) increases when the dye is exposed to an environment where there is increased hydrogen binding between the dye and a component of the environment. Such an increase in hydrophobicity or an increase in hydrogen bonding can occur when a presently disclosed biosensor comprising a dye of Formula (I) or Formula (II) binds to a target protein or subcellular component. In other embodiments, the fluorescence signal provided by the dye of Formula (I) or Formula (II) decreases when the dye is exposed to an environment that is more hydrophilic. In further embodiments, the fluorescence signal provided by the dye of Formula (I) or Formula (II) decreases when the dye is exposed to an environment that has less hydrogen binding. Such an increase in hydrophilicity or a decrease in hydrogen binding can occur when a biosensor comprising a dye of Formula (I) or Formula (II) is exposed to an aqueous environment or when such a biosensor becomes unbound from a target protein or subcellular component.

In some embodiments, the presently disclosed dyes can have an extended zwitterion structure having a polarized ground state (see, e.g., Schemes 5, 6, and 17), which allows the presently disclosed dyes to respond to changes in solvent polarity. Such dyes can exhibit a strong solvent-dependent excitation wavelength shift, while retaining a bright fluorescence. Other solvent-sensitive dyes currently used in vitro are poorly suited for use in living cells. They are not sufficiently bright to quantify spectral changes from small amounts of labeled protein, and their short excitation and emission wavelengths damage cells and overlap cellular autofluorescence. To be bright and fluoresce at longer wavelengths, dyes must have extended conjugation, which can reduce water solubility and lead to self-aggregation. The dyes designed for use in living cells were specifically selected to be insensitive to their environment, because they are used to quantify protein distribution (i.e., Fluorescein, Rhodamine, Alexa, Cy3/5). In such dyes, solubility problems could be overcome by incorporating charged groups around the dyes' edges. This approach might not be desirable in dyes that are intended to be used for detecting proteins, because those dyes must interact with hydrophobic protein regions to be useful for reporting protein conformational changes. Dyes must interact with the protein surface so that protein conformational changes affect their interactions with water, hydrogen bonding, or hydrophobic interactions. For domain- or antibody-based sensors, dyes must be able to move from water to hydrophobic pockets during protein binding events. Prior to the development of the presently disclosed dyes, use of solvatochromic dyes to monitor protein activity in vivo was restricted to proteins that could be labeled with hydrophobic dyes in organic cosolvents. Hahn et al., *J. Biol. Chem.* 265:20335-20345 (1990).

Such environmentally-sensitive dyes can be used as biosensors. Use of biosensors with the presently disclosed dyes of Formula (I) or Formula (II) can provide advantages over currently available affinity probe schemes, such as those that involve imaging antibodies labeled with non-environmentally sensitive dyes. See, e.g., Nizak et al., *Science* 300:984-987 (2003). For example, the presently disclosed methods allow a change in fluorescence intensity or emission wavelength to be measured in near real time, as compared to the visualization of a target retrospectively by radioactive or ELISA formats. In many cases, the fleeting presence of target cannot be observed by methods with delayed detection.

The presently disclosed dyes can be compatible with aqueous chemistries or aqueous/organic solvent combinations used to prepare biosensors. The dyes can have reactive groups and/or protected groups to facilitate processes for binding dyes to binding members, e.g., binding members having one or more binding domains. Biosensors comprising a dye of Formula (I) or Formula (II), e.g., dyes linked to a binding member, can be compatible with and move freely in intracellular and/or extracellular environments of living cells. Dyes on the biosensors can exist in or near binding regions between a sensor and target to provide a detectable signal without significantly interfering with binding.

The presently disclosed dyes of Formula (I) or Formula (II) generally have an emission wavelength in the visible spectral region and can, in some embodiments, exhibit a ratiometric response to one or more target molecules. Embodiments that exhibit a shift in excitation or emission wavelength upon ligand binding enable a biosensor comprising a presently disclosed dye of Formula (I) or Formula (II) to be self-referencing. In such embodiments, the fluorophore exhibits an increase in a first excitation or emission wavelength in the presence of a target molecule and a decrease in a second wavelength. A ratio between the first wavelength and the second wavelength can be calculated to determine the amount of target molecule in the sample under test. Such self referencing can correct for variations in excitation source intensity and other sources of noise and instability in the biosensor without requiring a reference dye. Thus, a single fluorophore can be used to observe a ratiometric response in the biosensor. As used herein, the term "ratiometric response" means that the intensities of the first wavelength and the second wavelength vary such that the ratio of the two emission wavelengths can be used to indicate interaction with the target molecule in a sample.

C. Biosensors Comprising Dyes of Formula (I) or Formula (II)

In some embodiments, the presently disclosed subject matter provides a biosensor comprising a dye of Formula (I) or Formula (II) and a binding member having a specific affinity for a target molecule that can be used to detect and quantify the presence and/or activities of one or more target molecules. The biosensor can bind to one or more target molecules and the detection of such binding events can be used in homogeneous assays, i.e., assays in which the fluorescent properties of the dye can undergo a change as a result of the binding event, and for live-cell imaging. The presently disclosed biosensors can be used to detect and/or quantify diverse protein activities, including changing subcellular locations, conformational changes, activation states, posttranslational modifications, and/or small ligand binding of proteins in vivo.

As used herein, the terms "biosensor" and "biosensor compound" generally refer to a compound that undergoes a detectable change in specific response to a target molecule. The presently disclosed biosensors combine the molecular recognition properties of biological macromolecules, such as a binding member of a specific binding pair, with a fluorophore capable of producing a detectable signal, e.g., a detectable change in one or more fluorescent properties, upon binding with a target molecule. The term "producing a detectable signal" refers to the ability to recognize a change in a property of a reporter group, e.g., a fluorophore, in a manner that enables the detection of ligand-protein binding.

The presently disclosed subject matter provides methods which can use specific binding partners for a particular target molecule of interest. A specific binding partner or member, as used herein, is a member of a specific binding pair. A "specific binding pair" refers to two different molecules where one of the molecules through chemical or physical means specifically binds the second molecule. In this sense, a target molecule is a reciprocal member of a specific binding pair. Further, specific binding pairs can include members that are analogs of the original specific binding partners, for example, an analog of a target molecule can have a similar structure to the target molecule. By "similar" it is intended that, for example, an analog has an amino acid sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater amino acid sequence identity compared to a target molecule amino acid sequence using alignment programs and standard parameters well known in the art. An analog of a target molecule also can have the same function as the target molecule.

A biosensor can translate a binding event into a directly measurable fluorescent property. Such changes in one or more fluorescence properties include, but are not limited to, an increase or decrease in fluorescence intensity, a shift in excitation or emission maxima, shape of the excitation or emission band profiles, a change in fluorescence lifetime, a change in anisotropy, a change in polarization, and combinations thereof. Further, the producing of a detectable signal can be reversible or non-reversible. The signal-producing event includes continuous, programmed, and episodic means, including one-time or reusable applications. The reversible signal-producing event can be instantaneous or can be time-dependent, so long as a correlation with the presence or concentration of target molecule is established.

As used herein, the term "fluorophore" includes a moiety of a larger molecule or conjugate that can be induced to emit fluorescence when irradiated, i.e., excited, by electromagnetic radiation of an appropriate wavelength. More particularly, a fluorophore can be a functional group of a molecule or conjugate that absorbs light of a certain wavelength and emits light at different wavelength. The intensity and the wavelength of the light emitted, as well as other fluorescence properties including, but not limited to, fluorescence lifetime, anisotropy, polarization, and combinations thereof, depend on the identity of the fluorophore and its chemical environment. A fluorophore can include a fluorescent molecule, such as the presently disclosed dyes of Formula (I) or Formula (II).

Accordingly, in some embodiments, the presently disclosed subject matter provides a biosensor comprising a dye of Formula (I) or Formula (II):

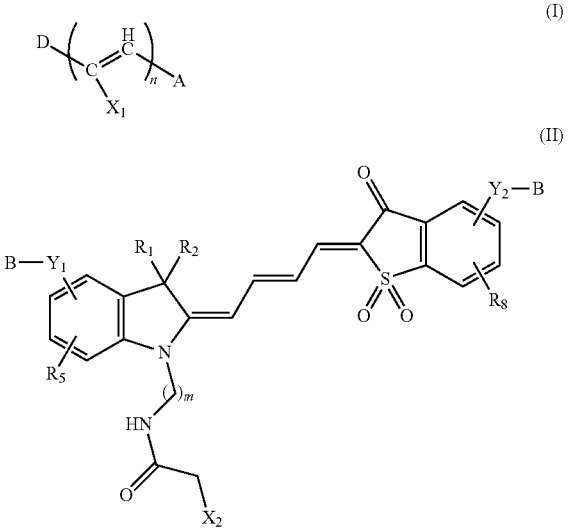

wherein:
n is an integer from 1 to 4;
m is an integer from 1 to 4;
each $X_1$ is independently an electron-accepting group selected from the group consisting of cyano, halogen, $CF_3$, $NO_2$, sulfonyl, —COOH and combinations thereof;
$X_2$ is halogen or a binding member, B;
D is selected from the group consisting of:

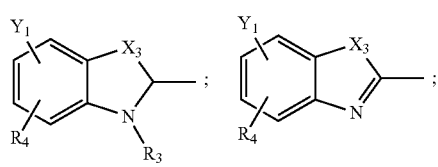

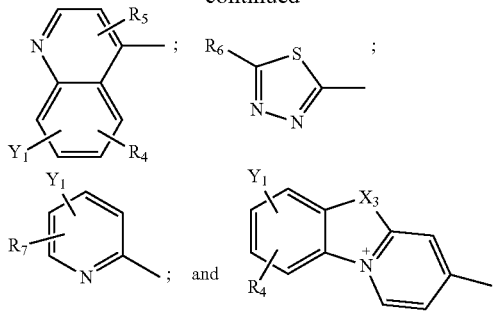

wherein:
each $X_3$ is independently selected from the group consisting of O, S, and $CR_1R_2$;
$R_1$, $R_2$, $R_3$, $R_5$, $R_6$, and $R_7$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, alkoxycarbonyl, alkyleneaminoalkyl, alkylenesulfate, —$(CH_2)_p$—$SO_3$, —$(CH_2)_p$—$N^+(CH_3)_2$—$(CH_2)_p$—NCS, and —$(CH_2)_p$—NH—CO—$CH_2$—$X_2$; wherein $X_2$ is halogen;
$R_4$ is selected from the group consisting of H, alkyl, substituted alkyl, hydroxyl, amino, nitro, alkoxyl, and hydroxyalkyl;
A is selected from the group consisting of:

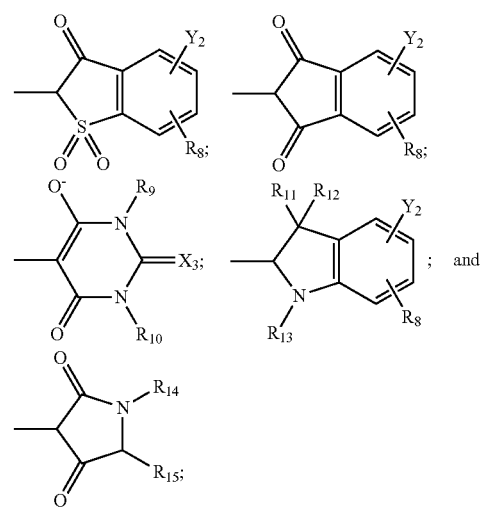

wherein:
$X_3$ is O, S, or $CR_1R_2$;
$R_8$ is selected from the group consisting of H, alkyl, substituted alkyl, hydroxyl, amino, nitro, alkoxyl, and hydroxyalkyl;
$R_9$, $R_{10}$, $R_{11}$, $R_{12}$, $R_{13}$, $R_{14}$, and $R_{15}$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, alkoxycarbonyl; and tolyl-acetonitrile;

$Y_1$—B and $Y_2$—B are each independently selected from the group consisting of B—$CH_2CONH$—, B-SuOCOCH$_2$OCH$_2$CON(CH$_3$)—, —(CH$_2$)$_r$—NH—(=O)—(CH$_2$)$_s$—B, a succinimidyl ester, a hydroxysuccinimide, a maleimide, a haloacetyl, a pyridyl disulfide, a hydrazine, an ethyldiethylamino propylcarbodiimide,

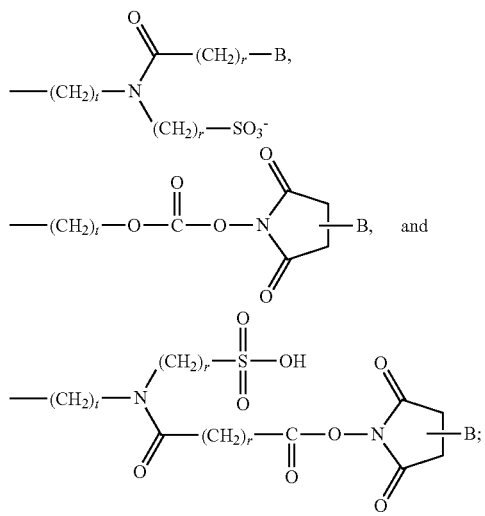

wherein each p, r, s and t is independently an integer from 1 to 8; and

Su is succinimidyl ester;

and wherein at least one of $Y_1$ and $Y_2$ is present, under the proviso that if $X_2$ in Formula (II) is B, then one or both of $Y_1$ and $Y_2$ can be absent, and when present are conjugated with B, wherein B is a binding member having an affinity for a target molecule, and wherein if two or more Bs are present in the biosensor, the two or more Bs can be the same or different; and wherein the biosensor exhibits a detectable change in a fluorescence property during or after binding to the target molecule.

In some embodiments, the presently disclosed dyes of Formula (I) or Formula (II) include a reactive group, e.g., substituents $Y_1$ and $Y_2$, which can be conjugated with another molecule, such as a binding member, i.e., B, of a specific binding pair, which has an affinity for a target molecule of interest, e.g., the other member of a binding pair. Such conjugates can be used as a biosensor compound to detect the presence, location, conformation, activation state, modification, binding, and the like, of a target molecule.

As used herein, the term "conjugate," and variations thereof, refers to a molecule comprising two or more subunits bound together, optionally through a linking group, to form a single molecular structure. The binding of the two or more subunits can be through a direct chemical bond between the subunits or through a linking group. Such binding in a conjugate typically is irreversible. As used herein, the term "affinity" refers to the strength of the attraction between one binding member of a specific binding pair to another binding member of a specific binding pair at a particular binding site. The term "specificity" and derivations thereof, refer to the likelihood that a binding member will bind to another member of a specific binding pair. Such binding between one binding member, e.g., a binding protein, to another binding member of a specific binding pair, e.g., a ligand or analyte, can be reversible.

In some embodiments, substituents $Y_1$ and $Y_2$ can be a linker group and the presently disclosed dyes can be linked to a binding member of a specific binding pair, such as a binding protein, or a portion thereof, such as a binding domain, to prepare a biosensor. In some embodiments, the binding member includes one or more linker reactive groups, i.e., functional groups that can attach to, e.g., form a covalent bond with, a linker group, and the dye includes a linker group. Alternatively, in some embodiments, the dye includes the linker reactive group and the binding member includes the linker group. In another embodiment, both the binding member and dye include linker reactive groups. In such embodiments, the linkage is through a bivalent linker group. Generally, a linkage can be formed by contacting the binding member and dye in solution. The linker can be a flexible chain-like structure, such as an aliphatic chain or a polymer. In some embodiments, the linker is a peptide or nucleic acid having hydrophilic character.

In some embodiments, linker reactive groups can be provided on dye molecules of Formula (I) or Formula (II). In such embodiments, the presently disclosed dyes of Formula (I) or Formula (II) can be derivatized to make reactive forms which could be site-specifically attached to proteins. As used herein, the term "derivatized," and variations thereof, is meant to include any chemical modification, addition, deletion, or substitution to a parent compound. Further, a derivative can include any reaction product of the derivative, for example, the reaction product of the derivative with an amino acid residue. Accordingly, in some embodiments, the presently disclosed dyes can include an aromatic ring structure having a linker reactive group that can be conjugated, e.g., covalently attached, to an amino acid, for example, an amino acid residue of a protein. A non-limiting example of a derivative is an ester or amide of a parent compound having a carboxylic acid functional group.

For example, derivatives of the presently disclosed dyes of Formula (I) or Formula (II) can be made with succinimidyl ester linker for attachment to lysine or with an iodoacetyl linker for selective reaction with cysteine. Use of these groups for site-specific protein labeling is known in the art. See, e.g., Dent and Aslarn, *Bioconjugation*, 364-482 (1998). For example, the reactive dyes of Formula (I) or Formula (II) can be synthesized from starting materials having an amino group, which can be used for attachment of a side chain comprising a reactive linker group at the end of the synthesis. Accordingly, in some embodiments, cysteine-selective iodoacetyl groups can be attached to the dye ring structure for covalent binding to a binding member or binding domain thereof.

In some embodiments, the presently disclosed dyes can include a thiol-reactive group that can be conjugated to the thiol moiety of a cysteine amino acid residue in a natural or unnatural protein. As used herein, the term "thiol-reactive group" refers to a substituent group that can react with a thiol moiety to form a carbon-sulfur bond. Examples of suitable thiol-reactive groups that can be introduced into the presently disclosed dyes include a halo-acetyl group, i.e., a halo-acetamido group. In some embodiments, the halo-acetyl group includes an iodoacetyl group. One of ordinary skill in the art upon review of the presently disclosed subject matter would recognize that other thiol-reactive groups known in the art, such as maleimide groups, are suitable for use with the presently disclosed subject matter.

In some embodiments, the residue to which the dye is attached is a cysteine. In some embodiments, one or more such residues can include linker reactive groups other than cysteine. Linker reactive groups can include any chemical functional groups on the dye, the binding member, or both, that can react with selected linkers to form one or more chemical bonds. For example, natural amino acids, modified or derivatized amino acids, and/or other residues in a binding member or binding domain can provide linker reactive groups, such as amines, sulfhydryls, carboxylic acids, alcohols, aldehydes, and thiols, that can covalently bond to linker molecules.

Linkers can be any type suitable to react with linker reactive groups to form a linkage between selected binding members to dyes of Formula (I) or Formula (II). Representative linkers suitable for use with the presently disclosed subject matter include, but are not limited to, hydroxysuccinimide linkers (reactive with primary amines), maleimides, haloacetyls, pyridyl disulfides (reactive with sulfhydryl groups), hydrazines (reactive with aldehydes), and ethyldiethylamino propylcarbodiimide (EDC, reactive with carboxyl groups). Linkers can include a flexible aliphatic or polymer chain of suitable length and hydrophilicity to bridge between linked molecules. Bivalent linker groups having the same or different linker chemistries at each end also can be used. Linkers can include one or more protective group to protect the linker group during storage, handling or other chemistries. The protective group can be removed under defined conditions to allow completion of the linker reaction.

Further, based on sequence data and the crystal structure of binding domains of the binding members, one or more dyes of Formula (I) or Formula (II) can be attached to provide the presently disclosed biosensors. For example, based on the sequence data and the crystal structure of a free Fab fragment, several merocyanine dyes can be attached to a series of one or more different residue positions to create a small but intelligently designed library of biosensor candidates. The resultant library can be screened, as can be appreciated by those in the art, to identify candidates with desired properties, e.g., of signal strength and binding affinity.

Intelligent design of linkage reactions can be accomplished with the selection of a target reactive group in a binding member or binding domain, or engineering of a desired reactive group into the binding member or binding domain. For example, a binding member or binding domain can naturally have a cysteine residue (reactive, for example, with a haloacetyl linker) at an appropriate location, or can be mutated to include such a cysteine residue. Alternatively, a binding member or a binding domain can have a small number of cysteine residues. Binding members or binding domains can be modified or mutated to contain a single or a small number of cysteine residues by procedures known in the art.

1. Representative Binding Members

Binding members suitable for use with the presently disclosed subject matter can include any molecules that bind to a target molecule with suitable specificity. Binding members typically include binding regions of affinity molecules known in the art including, but not limited to, antibodies, antibody fragments, leucine zippers, histones, enhancers, complementary determining regions (CDRs), to single chain variable fragments (scFv's), receptors, ligands, aptamers, lectins and one of several proteins in a protein complex or a protein pair. Binding members can comprise either member of a binding pair, e.g., a pair of proteins in a protein-protein interaction, with the binding member being identified as the member introduced into an assay system to probe for a target molecule. Binding members or binding domains thereof can be binding regions of, for example, full sized versions of the affinity molecule, fragments of the affinity molecule, or the smallest portion of the affinity molecule providing binding useful in the detection of a target molecule. In some embodiments, the binding member can have specific affinity to endogenous (e.g., constitutive or inducible, but not recombinant) peptides of a cell.

In some embodiments, the binding member B is a binding protein. As used herein, the term "binding protein" refers to a protein, that when conjugated with a fluorophore, interacts with a specific target molecule in a manner capable of producing a detectable florescence signal differentiable from when a target molecule is present or absent, or when a target molecule is present in varying concentrations over time.

The binding member can comprise a binding domain. Binding domains suitable for use with the presently disclosed biosensors can comprise polypeptide, peptide, or nucleic acid sequences. For example, binding domains can be single stranded DNA (sDNA), double stranded DNA (dsDNA), RNA, nucleic acids with modified bases, and the like. In one embodiment, the binding domain can be an oligonucleotide probe and the target can be a complimentary target nucleic acid. In another embodiment, the binding domain can be a dsDNA strand specific to a target enhancer protein target. The presently disclosed dyes of Formula (I) or Formula (II) can be linked to nucleic acids by any technique known in the art, such as by reaction of linker groups on the dye to reactive groups available on modified bases on the nucleic acid.

Affinity specificity of peptide binding domains can be provided by a short sequence of amino acids (e.g., a sequence of amino acids comprising 3 to 20 residues, i.e., 3, 4, 5, 6, 7, 8, 9, 10, 11, 12, 13, 14, 15, 16, 17, 18, 19, or 20 residues), or the specificity can rely on contributions of amino acid side chains brought in proximity by the primary, secondary, tertiary, and/or quaternary structural conformations of one or more affinity proteins.

Binding domains comprising peptides can have natural amino acid side chains, modified side chains, or the like, that provide reactive groups specifically reactive with linkers on dyes of Formula (I) or Formula (II). In some embodiments, the dye of Formula (I) or Formula (II) can have reactive groups specifically reactive with linker groups present on the binding domain to link the dye to the domain. The position of a dye on a domain can be determined by the location of a reactive group or linker moiety on the domain. In some embodiments, the binding domain has one or more cysteine residues reactive with groups on the dyes, for example, iodoacetyl groups on the dyes.

The presently disclosed biosensors can incorporate binding domains of naturally occurring proteins having specific binding activity. The binding domains can include, for example, full length affinity proteins, members of protein-protein interaction pairs (or portions thereof), Fv antibody fragments, aptamers, Vh antibody fragments, and the like. In one embodiment, the biosensors comprise binding domains that are members of the immunoglobulin family of proteins, or derivatives thereof. For example, the binding domain can be a complete immunoglobulin, fragment, single chain variable fragment (scFv), a heavy or light chain variable region, a CDR peptide sequence, and/or the like.

In some embodiments, an antibody or antibody fragment can be used in a binding domain to which dyes of Formula (I) or Formula (II) can be attached to form a biosensor. An antibody suitable for use with the presently disclosed subject matter can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody," as used herein. The use of any specificity of an antibody, polyclonal or monoclonal, is intended to fall under the scope of the presently disclosed subject matter. In some embodiments, in the context of methods described herein, an antibody, or fragment thereof is used that is immunospecific for a selected target.

As used herein, the term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called Fab fragments, each with a single antigen binding site, and a residual Fc fragment. Fab fragments thus have an intact light chain and a portion of one heavy chain. Pepsin treatment yields an F(ab')$_2$ fragment that has two antigen binding fragments that are capable of cross-linking antigen, and a residual fragment that is termed a pFc' fragment. Fab' fragments are obtained after reduction of a pepsin digested antibody, and consist of an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

Fv is a small antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer Collectively, the six CDRs confer antigen binding specificity to the antibody. Even a single variable domain (or half of an Fv comprising only three CDRs specific for an antigen), however, has the ability to recognize and bind antigen, although at a lower affinity than the entire binding site. Antibody fragments usefully incorporated into the presently disclose biosensors can include, but are not limited to, single CDRs, $V_H$ regions, $V_L$ regions, Fv fragments, F(ab) and F(ab')$_2$ fragments.

Additional fragments can include diabodies, linear antibodies, single-chain antibody molecules, and multispecific antibodies formed from antibody fragments. Antibody fragments suitable for use with the presently disclosed binding domains can include, e.g., natural, synthetic, or recombinant versions. Single chain antibodies are genetically engineered molecules containing the variable region of a light chain and a variable region of the heavy chain, linked by a suitable polypeptide linker as a genetically fused single chain molecule. Such single chain antibodies also are referred to as "single-chain Fv" or "scFv" antibody fragments. Generally, the Fv polypeptide further comprises a polypeptide linker between the $V_H$ and $V_L$ domains that enables the scFv to form the desired structure for antigen binding. For a description of scFv, see Pluckthun, in *The Pharmacology of Monoclonal Antibodies*, vol. 113, Rosenburg and Moore eds. Springer-Verlag, N.Y., pp. 269-315 (1994).

In some embodiments, the binding domain can be a single chain variable fragment (scFv) of an antibody with an attachment site for a dye within a CDR3 region of the scFv, a modified fragment of a naturally occurring protein, or another entity that binds to a specific state of the targeted protein or polypeptide. Any available scFv can be used provided that it binds to a selected target with sufficient affinity to permit detection of a complex formed between the scFv and the selected target. A dye of Formula (I) or Formula (II) can be attached to the selected scFv at any convenient site. The fluorescence of the attached dye, however, can be influenced by its attachment position. Single chain variable fragment (scFv) binding domains can be useful in modular biosensors in which binding domain and/or target modules connected with a linker can be replaced with alternate versions to provide new desired specificities to the sensor. In some embodiments, scFvs can be combined with dyes of Formula (I) or Formula (II) for methods of probing living cells.

Antibody fragments suitable for use with the presently disclosed subject matter do not have to be full-length antibodies. Such antibody fragments, however, can have similar or improved immunological or other properties relative to a full-length antibody. For example, such antibody fragments can be smaller and more stable than full-length antibodies. Such antibody fragments can include about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids, or more.

In general, an antibody fragment can have any upper size limit so long as it is has similar or improved properties relative to an antibody that binds with specificity to a target molecule. For example, smaller antibody fragments can have less than about 200 amino acids, less than about 175 amino acids, less than about 150 amino acids, or less than about 120 amino acids if the antibody fragment is related to a light chain antibody subunit. Moreover, larger antibody fragments can have less than about 425 amino acids, less than about 400 amino acids, less than about 375 amino acids, less than about 350 amino acids, less than about 325 amino acids or less than about 300 amino acids if the antibody fragment is related to a heavy chain antibody subunit.

Antibodies and antibody fragments directed against selected targets can be prepared by techniques commonly known in the art. In some embodiments, antibody fragments can be prepared from full-length antibodies. Methods for the preparation of polyclonal antibodies are available to those skilled in the art. See, for example, Green, et al., Production of Polyclonal Antisera, in: *Immunochemical Protocols* (Manson, ed.), pages 1-5 (Humana Press); Coligan, et al., Production of Polyclonal Antisera in Rabbits, Rats Mice and Hamsters, in: *Current Protocols in Immunology*, section 2.4.1 (1992), which are incorporated herein by reference in their entirety. Such polyclonal antibodies can be cleaved, e.g., by chemical or enzymatic treatment to prepare antibody fragments useful in the presently disclosed methods.

Monoclonal antibodies, and fragments thereof, also can be used in the presently disclosed methods. The term "monoclonal antibody" as used herein refers to an antibody obtained from a population of substantially homogeneous antibodies. In other words, the individual antibodies comprising the population are identical except for occasional naturally occurring mutations in some antibodies that can be present in minor amounts. Monoclonal antibodies are highly specific, being directed against a single antigenic site. Further, in contrast to polyclonal antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method.

The monoclonal antibodies herein specifically include "chimeric" antibodies in which a portion of the heavy and/or light chain is identical or homologous to corresponding sequences in antibodies derived from a particular species or belonging to a particular antibody class or subclass, while the remainder of the chain(s) are identical or homologous to corresponding sequences in antibodies derived from another species or belonging to another antibody class or subclass. Fragments of such antibodies also can be used, so long as they exhibit the desired biological activity. See U.S. Pat. No. 4,816,567; Morrison et al., *Proc. Natl. Acad. Sci.* 81:6851-55 (1984).

The preparation of monoclonal antibodies is conventional. See, for example, Kohler and Milstein, *Nature*, 256:495 (1975); Coligan et al., sections 2.5.1-2.6.7; and Harlow et al., in: *Antibodies: A Laboratory Manual*, page 726 (Cold Spring Harbor Pub. (1988)), which are incorporated herein by reference in their entirety. Monoclonal antibodies can be isolated and purified from hybridoma cultures by a variety of established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., Purification of Immunoglobulin G (IgG), in: *Methods in Molecular Biology*, Vol. 10, pages 79-104 (Humana Press (1992)).

Methods of in vitro and in vivo manipulation of antibodies are available to those skilled in the art. For example, the monoclonal antibodies to be used in accordance with the presently disclosed subject matter can be made by the hybridoma method or can be made by recombinant methods, e.g., as described in U.S. Pat. No. 4,816,567, which is incorporated herein by reference in its entirety Monoclonal antibodies suitable for use with the presently disclosed subject matter also can be isolated from phage antibody libraries using the techniques described in Clackson et al., *Nature* 352:624-628 (1991), as well as in Marks et al., *J. Mol. Biol.* 222:581-597 (1991).

Methods of making antibody fragments are also known in the art (see for example, Harlow and Lane, Antibodies: *A Laboratory Manual*, Cold Spring Harbor Laboratory, New York, (1988), incorporated herein by reference). Antibody fragments suitable for use with the presently disclosed subject matter can be prepared by proteolytic hydrolysis of the antibody or by expression of nucleic acids encoding the antibody fragment in a suitable host: Antibody fragments can be obtained by pepsin or papain digestion of whole antibodies conventional methods. For example, antibody fragments can be produced by enzymatic cleavage of antibodies with pepsin to provide a 5 S fragment described as F(ab')$_2$. This fragment can be further cleaved using a thiol reducing agent, and optionally using a blocking group for the sulfhydryl groups resulting from cleavage of disulfide linkages, to produce 3.5 S Fab' monovalent fragments. Alternatively, enzymatic cleavage using pepsin produces two monovalent Fab' fragments and an Fc fragment directly. These methods are described, for example, in U.S. Pat. Nos. 4,036,945 and 4,331,647, and references contained therein, which patents are incorporated herein by reference in their entireties.

Other methods of cleaving antibodies, such as separation of heavy chains to form monovalent light-heavy chain fragments, further cleavage of fragments, or other enzymatic, chemical, or genetic techniques also can be used, so long as the fragments bind to the antigen that is recognized by the intact antibody. For example, Fv fragments comprise an association of $V_H$ and $V_L$ chains. This association can be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *Methods: a Companion to Methods in Enzymology*, Vol. 2, page 97 (1991); Bird et al., *Science* 242:423-426 (1988); Ladner et al, U.S. Pat. No. 4,946,778; and Pack et al., *Bio/Technology* 11:1271-77 (1993).

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*, Vol. 2, p. 106 (1991).

The amino acid sequence of monoclonal antibodies, polyclonal antibodies, fragments thereof, and such, can be determined by amino acid sequencing methods known in the art. Amino acid sequences of antibodies and fragments of interest can evaluated for binding sequences, such as, e.g., CDR sequences, useful in the presently disclosed biosensors. Desired sequences can be directly synthesized or translated into nucleic acid sequences for manipulation by genetic engineering techniques known in the art Amino acid and nucleic acid sequences thus obtained can be screened for binding characteristics desirable in the presently disclosed biosensors. Optionally, sequences thus obtained can be logically modified and/or randomly mutated to generate additional binding domain candidates that can be screened to identify sequences most useful in particular biosensor systems of interest.

Human and humanized forms of non-human (e.g., murine) antibodies also are suitable for use with the presently disclosed subject matter. Such humanized antibodies are chimeric immunoglobulins, immunoglobulin chains or fragments thereof (such as Fv, scFv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity.

In some embodiments, Fv framework residues of the human immunoglobulin can be replaced by corresponding non-human residues. Furthermore, humanized antibodies can comprise residues that are found neither in the recipient antibody nor in the imported CDR or framework sequences. These modifications can be made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optionally can comprise at least a portion of an immunoglobulin constant region (Fc), typically that of a human immunoglobulin. For further details, see Jones et al., *Nature* 321:522-525 (1986); Reichmann et al., *Nature* 332:323-329 (1988); Presta, *Curr. Op. Struct. Biol.* 2:593-

596 (1992); Holmes et al., *J. Immunol.* 158:2192-2201 (1997) and Vaswani et al., *Annals Allergy, Asthma & Immunol.* 81:105-115 (1998).

In the immune system, specific antibodies are selected and amplified from a large library (affinity maturation). The combinatorial techniques employed in immune cells can be mimicked by mutagenesis and generation of combinatorial libraries of binding entities. Variant binding entities, antibody fragments and antibodies therefore also can be generated through display-type technologies. Such display-type technologies include, for example, phage display, retroviral display, ribosomal display, yeast display and other techniques. Techniques available in the art can be used for generating libraries of binding entities, for screening those libraries and the selected binding entities can be subjected to additional maturation, such as affinity maturation. Wright and Harris, supra, Hanes and Plucthau, *PNAS USA* 94:4937-4942 (1997) (ribosomal display), Parmley and Smith, *Gene* 73:305-318 (1988) (phage display), Scott, *TIBS* 17:241-245 (1992), Cwirla et al., *PNAS USA* 87:6378-6382 (1990), Russel et al., *Nucl. Acids Research* 21:1081-1085 (1993), Hoganboom et al., *Immunol. Reviews* 130:43-68 (1992), Chiswell and McCafferty, *TIBTECH* 10:80-84 (1992), and U.S. Pat. No. 5,733,743.

Methods for mutating antibodies, CDRs or binding domains can be used to optimize their affinity, selectivity, binding strength and/or other desirable properties. A mutant binding domain refers to an amino acid sequence variant of a selected binding domain (e.g., a CDR). In general, one or more of the amino acid residues in the mutant binding domain is different from what is present in the reference binding domain. Such mutant antibodies necessarily have less than 100% sequence identity or similarity with the reference amino acid sequence. In general, mutant binding domains have at least 75% amino acid sequence identity or similarity with the amino acid sequence of the reference binding domain. Preferably, mutant binding domains have at least 80%, more preferably at least 85%, even more preferably at least 90%, and most preferably at least 95% amino acid sequence identity or similarity with the amino acid sequence of the reference binding domain.

For example, affinity maturation using phage display can be utilized as one method for generating mutant binding domains. Affinity maturation using phage display refers to a process described in Lowman et al., *Biochemistry* 30(45): 10832-10838 (1991), see also Hawkins et al., *J. Mol. Biol.* 254: 889-896 (1992). While not strictly limited to the following description, this process can be described briefly as involving mutation of several binding domains or antibody hypervariable regions at a number of different sites with the goal of generating all possible amino acid substitutions at each site. The binding domain mutants thus generated are displayed in a monovalent fashion from filamentous phage particles as fusion proteins. Fusions are generally made to the gene III product of M13. The phage expressing the various mutants can be cycled through several rounds of selection for the trait of interest, e.g. binding affinity or selectivity. The mutants of interest are isolated and sequenced. Such methods are described in more detail in U.S. Pat. Nos. 5,750,373, 6,290,957 and Cunningham et al., *EMBO J.* 13(11):2508-2515 (1994).

Therefore, in one embodiment, the presently disclosed subject matter provides methods of manipulating binding entity or antibody polypeptides or the nucleic acids encoding them to generate binding entities, antibodies and antibody fragments with improved binding properties that recognize selected targets. Such methods of mutating portions of an existing binding entity or antibody involve fusing a nucleic acid encoding a polypeptide that encodes a binding domain to a nucleic acid encoding a phage coat protein to generate a recombinant nucleic acid encoding a fusion protein, mutating the recombinant nucleic acid encoding the fusion protein to generate a mutant nucleic acid encoding a mutant fusion protein, expressing the mutant fusion protein on the surface of a phage, and selecting phage that bind to a target.

Accordingly, the presently disclosed subject matter provides antibodies, antibody fragments, and binding entity polypeptides that can recognize and bind to selected target molecules. Thus, methods for manipulating those antibodies, antibody fragments, and binding entity polypeptides can be used to optimize their binding properties or other desirable properties (e.g., stability, size, ease of use).

In one embodiment, the biosensor molecule includes an HIV-1 neutralizing antibody Fab fragment (X5), which binds to HIV envelope protein gp120 after forming a complex with the host cell receptor CD4. The preparation of such biosensors is described in U.S. Patent Application Publication No. 2006/0029946 to Hahn, which is incorporated herein by reference in its entirety.

In one embodiment, a fragment of WASP, which binds only to the activated state of Cdc42, can be used to detect Cdc42 activation, as also described in U.S. Patent Application Publication No. 2006/0029946 to Hahn. Such biosensors can be used to detect and/or monitor the level of Cdc42 activity in vitro, in cell lysates, and in living cells. For example, a water-soluble and cysteine-reactive analog of AI-BA-CN dye that exhibited favorable characteristics for use in live cells was prepared. Labeling of Wiskott-Aldrich syndrome protein (WASP) fragment with the water soluble and cysteine reactive analog of the AI-BA-CN dye produced a ratiometric biosensor suitable for use in studying guanosine triphosphatase, e.g., Cdc42, protein activity in living cells.

As provided hereinabove, in some embodiments, the presently disclosed biosensors can be linked to a target molecule. In embodiments wherein the presently disclosed biosensors comprise a target molecule of interest, the dye can be linked to the target molecule at a position that results in a change in a signal from the dye upon changes to the target conformation, ligand binding to the target, protein-protein interactions with the target, phosphorylation of the target, or posttranslational modification of the target. The presently disclosed dyes of Formula (I) or Formula (II) can be linked to the target molecule in biosensors using the techniques of dye linkage known in the art and described in U.S. Patent Application Publication No. 2006/0029946 to Hahn. Suitable positions for linkage to provide, for example, improved signal intensity or minimal perturbation of normal biological activity can be identified using screening techniques also described in U.S. Patent Application Publication No. 2006/0029946 to Hahn.

In some embodiments, the presently disclosed dyes can be attached to a protein of interest, wherein an activity, location, and/or conformational change in the protein can result in a change in the fluorescence of the dye. In some embodiments, the protein of interest can be subject to a changed phosphorylation state and/or protein-ligand interaction, where the ligand can be a small molecule or a second protein. Dyes of Formula (I) or Formula (II) can be covalently attached to the protein of interest to provide a signal associated with the phosphorylation state and/or protein-protein interaction. This type of detection is in contrast to previously described detections, see, e.g., Hahn et al., *J. Am. Chem. Soc.* 125:4132-4145 (2003), wherein the biosensors detect a conformational change in the target protein induced by the action of a third element. In the presently disclosed methods, detection can be extended to conformational changes induced by phosphorylation and does not require induction of a conformational change in the protein of interest. One advantage of the presently disclosed methods is that proteins within multiprotein complexes can be monitored in situations where other types of biosensors, for example, those requiring a domain to find the target protein, would be blocked.

Further, the presently disclosed biosensors can allow the detection from a single dye, e.g., without the use of two fluorophores, as in FRET, to provide direct excitation and a brighter signal. In some embodiments, however, two or more of the presently disclosed dyes of Formula (I) or Formula (II) having different emissions wavelengths can be used to enable imaging of multiple protein activities in the same cell simultaneously. Thus, in some embodiments, it can be desirable to provide more than one dye molecule on the binding domain of the biosensor to facilitate monitoring of a binding event.

The presently disclosed subject matter provides methods to examine protein activity, structure, or protein-protein interactions. The presently disclosed methods and biosensors can report protein localization, protein activation and/or report specific aspects of changing protein structure or interaction. The biosensors can be used in living cells and/or for homogeneous assays. For example, the activity of a protein in a complex mixture, such as cell lysate, can be determined by adding and detecting the biosensors without additional steps, such as wash steps, and the like.

In some embodiments, the presently disclosed subject matter provides a biosensor comprising one or more binding domains having a specific affinity for one or more target molecules in a specific state of phosphorylation. For example, the binding domain of the biosensor can have a specific affinity for a binding site produced upon a protein when that protein binds to a guanosine triphosphate, thereby activating the signal transduction protein. Optionally, the biosensor can have a significantly lower affinity for the inactive form of the protein (e.g., the protein bound to guanosine diphosphate instead of guanosine triphosphate). Thus, for example, a dye of the biosensor, e.g., a dye of Formula (I) or Formula (II), can occupy a position on the binding domain near the binding site such that, upon binding to its target, the binding environment alters the fluorescent signal from the dye. Further, the position can provide a detectable signal change in the dye without significantly inhibiting the biological activity of the targeted protein. Detection of the activated target in this embodiment does not require conformational changes in the target or the presence of third molecules interacting with the target.

The presently disclosed biosensors also can detect protein-protein interactions. Such interactions can be high affinity interactions, such as, for example, interactions between antigens and antibodies, or they can be lower affinity interactions, such as, for example, interactions between enzymes and substrates, signal cascade members, or members of protein complexes. In a protein-protein interaction between two binding members, one binding member can be considered the "target" and the other binding member the biosensor "probe." While the distinction between target and probe can be arbitrary, because the two interact with each other these terms are used to facilitate discussion of protein interaction. Generally, as used herein, the target can be the molecule to be detected and the probe can be a binding member introduced to interrogate a sample for the presence of the target in a state or form of interest. In a representative protein-protein biosensor, one member of the binding pair can have a binding domain complimentary to a binding site of the second binding pair member. One or both of the protein-protein interaction pair members can include an attached dye of Formula (I) or Formula (II). The protein-protein interaction pair members can be full-length, naturally occurring proteins, synthetic analogs of naturally occurring proteins, recombinant analogs of naturally occurring proteins, or fragments thereof.

The presently disclosed biosensors capable of having protein-protein interactions can have dyes of Formula (I) or Formula (II) at one or more positions on one or both binding members such that the dyes are positioned between the binding members during binding. In such embodiments, binding can cause a detectable change in the signal from the dye without significantly inhibiting the binding interaction between the binding members. Suitable dye positions can be identified by screening alternative positions for improved signal and/or binding function in the presently disclosed biosensor systems.

In some embodiments, the biosensor can have specific affinity for a target molecule in a specific conformation, bound to a specific ligand, or with a specific posttranslational modification other than phosphorylation.

In some embodiments, the presently disclosed subject matter provides a modular biosensor. Modular biosensors are sensors of unified design that allow certain components to be changed, e.g., to change the target specificity and/or signal character. Modular biosensors typically provide for convenient alteration of binding domain specificity. For example, an affinity molecule can be expressed from a recombinant expression construct, such as an expression vector. The genetic construct can include unique endonuclease sites bracketing the region encoding the binding domain so that alternate binding domains can be readily inserted into the construct for expression as part of a biosensor. The modular binding domains can be selected, e.g., from a library of binding domains. Optionally, the modules can be encoded scFv domains. The modular systems can include affinity molecules with alternate binding domain sites, alternate dye linkage sites, alternate dye linkage reactive molecules, alternate linked targets, alternate linkers, and/or the like. Alternately, the binding domain can be of broad specificity, and the target domain (i.e., different kinase consensus sequence peptides) can be switched in the modular design.

2. Detecting Presence and/or Activity of Target Molecules in Living Cells

Cell behavior can be regulated through transient activation of protein activities at specific subcellular locations. The ability to study translocation of proteins has been enhanced by advances in the microscopy of fluorescent protein analogues within living cells. In many cases, however, localized protein activities are controlled not by translocating proteins to the site of action, but by localized activation of a small portion of the protein pool. See Hahn and Toutchkine, *Curr. Opin. Cell Biol.* 14:167-172 (2002); Wouters et al., *Trends Cell Biol.* 11:203-211 (2001). Such behaviors typically are not apparent when studying protein translocations or when using in vitro biochemical approaches. Further, the outcome of signaling protein activation can depend on subtle variations in activation kinetics that are not discernible in the population averages generated by biochemical techniques. For precise quantification of rapid activation kinetics and of the level of protein activation, it also is necessary to measure protein activity in living cells. See Wouters et al., *Trends Cell Biol.* 11:203-211 (2001); Williams et al., *Nature* 318:558-561 (1985); Berridge, *J. Biol. Chem.* 265:9583-9586 (1990). Accordingly, a need exists for methods for monitoring protein movements in living cells.

The presently disclosed dyes exhibit many properties that make them suitable for detecting target molecules and their interactions in living cells. The dyes are, for example, bright, with long wavelengths outside of cellular autofluorescence background frequencies and that are less damaging to cells. Addition or deletion of parts of the aromatic system, or substituent groups thereon, can shift excitation and/or emission wavelengths of the dyes so that more than one event can be monitored in a cell at the same time.

The presently disclosed dyes can be detected in cells by observing changes in intensity, a change in the shape or maxima of the excitation or emission peak, and/or dye lifetime, to permit ratio imaging and other techniques that can eliminate effects of uneven illumination, cell thickness, and the like.

In some embodiments, the presently disclosed subject matter provides a method of detecting an activity or a location of one or more target molecule within a cell, the method comprising: (a) providing a biosensor comprising a dye of Formula (I) or Formula (II); (b) contacting the biosensor with a cell suspected of containing one or more target molecules to bind the one or more target molecules, if present, to the binding member; (c) irradiating the cell suspected of containing one or more target molecules with electromagnetic radiation to induce the dye of Formula (I) or Formula (II) to fluoresce; and (d) detecting one or more of: (i) a fluorescence property of the dye of Formula (I) or Formula (II); (ii) a change in a fluorescence property of the dye of Formula (I) or Formula (II); (iii) a location of a fluorescence of the dye of Formula (I) or Formula (II); and (iv) combinations thereof, to determine the an activity or location of one or more target molecules in the cell.

In some embodiments, the target molecule is selected from the group consisting of a protein, a receptor, a ligand, and an enzyme. In some embodiments, the cell is selected from the group consisting of a living cell, a cell lysate, a cell library, or a cell culture. In some embodiments, the activity or location of the one or more target molecules is selected from the group consisting of a phosphorylation state, a subcellular location, an interaction with one or more subcellular structures, and an interaction with one or more cellular proteins.

The presently disclosed methods and biosensors can be useful for detecting target molecules in or on the surface of various types of biological cells, including, mammalian, bacterial, fungal, yeast, insect, and plant cells. In some embodiments, target molecules can be detected in freshly isolated cells from mammals (e.g., humans), insects, fugal, or bacterial cells. For example, blood cells, such as B cells, T cells, monocytes, and neutrophils, and the like, can be probed with the presently disclosed biosensors. In other embodiments, stably maintained cell lines such as CHO, HEK-293, L-cells, 3T3 cells, COS, or THP-1 cells can be investigated using the presently disclosed methods.

Useful information can be obtained from any type of cell using the presently disclosed biosensors and methods. For example, mammalian cells, such as human cells or animal cells, that naturally or recombinantly express human proteins can be evaluated to identify potential human therapeutics, observed for interactions between biomolecules, and/or studied for the effects of ligands, drugs, and other molecules on mammalian and human systems. In another example, bacterial or fungal cells can be used to screen for potential antibiotic or anti-fungal agents.

In some embodiments, well characterized cell lines known to provide predictive models of human cell functions can be used to obtain results correlated with human systems in pharmaceutical and medical research. Exemplary cell lines useful in such research include, for example, COS cells, CHO cells, HEK-293 cells, RBL-1, Jurkat, U937, and YB-1 cells.

The cells to be monitored can be provided in either immobilized form or as a suspension culture. Immobilized cells, such as, e.g., cell lawns, tissue slices, or libraries, can be monitored, e.g., by microscopy, scanners, or with imaging systems. The immobilized cells can be monitored live or fixed for detection of target molecules in killed cells.

In many embodiments, cells subject to target molecule detection with the presently disclosed biosensors are in suspension. Suspended cells can be cells from suspension cell cultures or cells liberated from tissues or lawns. Suspended cells are particularly well suited to handling and monitoring in fluidic systems, such as cell sorters, cell counters, and microfluidic systems. Cell suspensions can be provided at cell densities appropriate to the handling system and detection method that is being employed. Determination of optimal cell densities is routine for one of ordinary skill in the art. In the case of flow-through embodiments, cell densities of monitored suspensions generally range from about 1 cell/nL to about 30 cells/nL in, e.g., a reaction vessel or detection channel. In the case of test tube or multiwell plate based reactions, cell densities typically range from about 1,000 cells/mm$^2$ to about 100,000 cells/mm$^2$. Of course, these ranges can vary depending upon, e.g., the cell types used, the type of biosensor employed, the type of interaction to be studied, the relative adherence of the cells to the vessel surfaces, as well as each other factors.

In sum, the presently disclosed subject matter provides biosensors that are capable of studying proteins in living cells. The dyes can be directly attached to proteins, enabling conformational changes to be followed in vivo for proteins incorporated in large molecular machines. For in vitro applications, the dyes exhibit an increased photostability and provide a substantially brighter signal than current solvent-sensitive fluorophores. Thus, they can enhance sensitivity for studying high-affinity binding interactions, small amounts of protein in high-throughput assays, or protein changes that produce only small effects on other dyes.

3. Administration of Biosensors Comprising Dyes of Formula (I) or Formula (II)

The presently disclosed biosensors can be used in vitro and/or in vivo to detect target molecules of interest. In some embodiments, the biosensors can be added to test samples in a homogenous assay and do not require addition of multiple reagents and/or wash steps before detection of the target molecule.

The presently disclosed biosensors can be contacted with target molecules in vitro by addition to a test sample containing the target molecules. Test samples for in vitro assays include molecular libraries, cell lysates, analyte eluates from chromatographic columns, and the like. The in vitro assay can take place in a chamber, such as, e.g., a well of a multiwell plate, a test tube, an Eppendorf tube, a spectrophotometer cell, conduit of an analytical system, channels of a microfluidic system, and the like. In an exemplary in vitro assay, an enzyme protein of interest is coated to the bottom of 96-well dishes also containing solutions representing a library of possible enzyme substrates. A presently disclosed biosensor having a specific affinity for enzyme-substrate complex is added to each well. A multiwell scanning fluorometer can be used to observe each well for fluorescence. Wells containing enzyme substrate can be identified as those in which fluorescent emissions at the wavelength of the biosensor dye. That is, in this example, the binding domain of the biosensor only binds to enzyme acting on substrate; the binding placing the dye into a binding pocket environment that significantly changes the emissions intensity of the dye.

In embodiments wherein the presently disclosed biosensors are administered to living cells, binding can take place with targets on the cell surface, or the biosensor is transferred into the cell to make contact with an intracellular target molecule. In some embodiments, the biosensor can penetrate a cell suspected of containing a selected target passively by mere exposure of the cell to a medium containing the biosensor. In other embodiments, the biosensor is actively transferred into the cell by mechanisms known in the art, such as, e.g., poration, injection, transduction along with transfer peptides, and the like.

In some embodiments, a translocation functionality can be incorporated on the biosensor to facilitate the translocation or internalization of that biosensor from the outside to inside the cell. As used herein, the term "translocation functionality" refers to a chemical compound, group or moiety that increases the cell's ability to internalize another compound or material, for example, a biosensor. Examples of such translocation functionalities include peptide recognition/transport sequences, liposomal compositions, or the like. Alternative translocation methods and compositions also can be used in accordance with the presently disclosed subject matter to induce uptake of the second component, including, e.g., electroporation, cell permeating compositions containing, e.g., PEG, porins, saponins, streptolysin, or the like.

Techniques useful for promoting uptake of biosensors include optoporation, for example, as described in Schneckenburger et al., *J. Biomed. Opt.* 7:410-6 (2002); or Soughayer et al., *Anal. Chem.* 72:1342-7 (2000). A variety of transduction peptides also are useful for promoting uptake of biosensors, including those described in Zelphati et al., *J. Biol. Chem.* 276:35103-10 (2001); Yang et al., *FEBS Lett.* 532:36-44 (2002); and Torchilin et al., *Proc. Natl. Acad. Sci. USA* 100:1972-7 (2003).

Additional techniques such as electroporation also can be used. Examples of electroporation procedures are provided in Glogauer and McCulloch, *Exp. Cell Res.* 200:227-34 (1992); Teruel and Meyer, *Science* 295:1910-2 (2002); and Teruel et al., *J. Neurosci. Methods* 93:37-48 (1999).

Another procedure for introducing molecules such as biosensors into cells is the osmotic shock procedure. Examples of osmotic shock procedures include those described in Okada and Rechsteiner, *Cell* 29:33-41 (1982); and Park et al., *J. Cell Physiol.* 135:443-50 (1988).

One of skill in the art also can use bead/syringe loading to introduce the presently disclosed biosensors into cells. Bead/syringe loading procedures are described in McNeil et al. *J. Cell Biol.* 98:1556-1564 (1984); and McNeil and Warder, *J. Cell Sci.* 88:669-678 (1987).

Nucleic acids encoding binding domains as disclosed herein can be introduced into cells in expression plasmids, e.g., by transduction or other forms of transformation. Once inside the living cells, the binding domain can be translated from the nucleic acid to a functional peptide. Dyes of Formula (I) or Formula (II) can enter the cell, e.g., by injection or diffusion, to become linked to the expressed binding domain to generate a biosensor in situ. The presently disclosed dyes also can be introduced into cells by other methods known in the art, including, but not limited to viral-based delivery systems, including viral-based nanoparticles, and lipid delivery vehicles, including liposomes, and the like.

4. Detection of Target-Biosensor Binding Reactions

A wide variety of binding reactions can be detected and monitored using the presently disclosed biosensors, for example, protein-protein interactions, receptor-ligand interactions, nucleic acid interactions, protein-nucleic acid interactions, and the like. Detection of a target molecule can provide identification of the target in a specified state, quantification of the target, and/or localization of the target. Multiple measurements can allow determination of kinetics. The ability to monitor multiple targets can permit monitoring of the balance between different signaling activities. In the intracellular environment, many of these reaction types are involved in the multiplicity of steps of signal transduction within cells. For example, activation of a particular cellular event is often triggered by the interaction between a cell surface receptor and its ligand. The signal from the receptor is often transmitted along via the binding of enzymes to other proteins, for example, kinases, which then pass the signal on through the cell until the ultimate cell system response is achieved. In many cases, the signal or ultimate response can be detected using the presently disclosed biosensors. For example, signal transduction often involves phosphorylation of system molecules that can be detected directly with the phosphate involved in the binding site, or indirectly through conformational changes induced by the phosphorylation.

In one embodiment, the presently disclosed subject matter provides methods for identifying the activation status of endogenous proteins in living cells. The presently disclosed biosensors can permit identification, quantification, and resolution of the spatial, temporal and compartmental regulation of receptor phosphorylation and activation during various processes, for example, endocytosis. In another embodiment, the presently disclosed biosensors and methods can permit observation of epidermal growth factor receptor (EGFR) effects on the development and progression of breast cancer. In a further embodiment, complex formation between HIV gp120 and CD4 cell receptors can be monitored.

Accordingly, in some embodiments, the presently disclosed subject matter provides a method of detecting an interaction between an endogenous target molecule and a cellular entity, the method comprising: (a) providing a cell comprising an endogenous target molecule; (b) providing a probe comprising a binding member having a specific binding affinity for a binding site on the target molecule and a dye of Formula (I) or Formula (II); (c) observing a background fluorescence signal from the probe of step (b); (d) contacting the probe with the cell; and (e) detecting a change in fluorescence from the probe to indicate an interaction between the target molecule and the cellular entity.

In some embodiments, the cellular entity is selected from the group consisting of a cellular nucleic acid, a protein, a peptide, an enzyme, a receptor, a cytokine, a cytoskeleton, and a signal transduction protein. In some embodiments, the binding member of the probe binds the target molecule at a phosphorylation site. In some embodiments, the binding member has a specific affinity for a conformation, a ligand interaction, or posttranslational modification of the target molecule. In some embodiments, the detecting a change in fluorescence comprises quantifying a protein amount, locating a protein, detecting a conformational change in the target molecule, detecting activation of the target molecule, or detecting phosphorylation of the target molecule.

In some embodiments, the dye of Formula (I) or Formula (II) is linked to the binding member at a site that does not substantially interfere with binding between the probe and the target biomolecule. Further, in some embodiments, the site is selected by an examination of a crystal structure for the binding member or the target molecule. In some embodiments, the method further comprises introducing the probe into the cell by using a technique selected from the group consisting of electroporation, transduction, microporation, and microinjection.

5. Methods for Detecting the Presence or Amount of a Target Molecule

In accordance with the presently disclosed subject matter, binding interactions can occur between a biosensor and one or more target molecules or components of the cell. A 'target molecule of interest" is a molecule that is known by one of skill in the art and is selected for interaction with a presently disclosed biosensor. A target molecule often comprises an endogenous unlabeled and/or untagged component of a test solution or cell. Endogenous components can be, e.g., expressed by the cell naturally, or present as a result of introduction of an appropriate genetic construct within the cell. For example, nucleic acid or protein target molecules can be expressed in the cell, either naturally (e.g., constitutively) or by induction of an appropriate genetic construct introduced into the cell line.

In some embodiments, the presently disclosed subject matter provides a method for determining the presence or amount of one or more target molecules in a sample, the method comprising: (a) providing a biosensor comprising a dye of Formula (I) or Formula (II); (b) contacting the biosensor with a sample suspected of containing one or more target molecules to bind the one or more target molecules, if present, to the binding member; (c) irradiating the sample suspected of containing one or more target molecules with electromagnetic radiation to induce the dye of Formula (I) or Formula (II) to fluoresce; and (d) detecting a fluorescence property of the dye of Formula (I) or Formula (II) to determine the presence or amount of one or more target molecules in the sample.

In some embodiments, the method further comprises: (a) measuring a fluorescence intensity at a first emission wavelength before contacting the biosensor with a sample suspected of containing one or more target molecules; (b) measuring a fluorescence intensity at a second emission wavelength after contacting the biosensor with a sample suspected of containing one or more target molecules; and (c) determining a ratio of the second emission wavelength to the first emission wavelength to determine the presence or amount of one or more target molecules in the sample.

In some embodiments, the method further comprises continuously: (a) contacting the biosensor with the sample suspected of containing one or more target molecules; (b) irradiating the sample with electromagnetic radiation; and (c) detecting the fluorescence property of the dye of Formula (I) or Formula (II).

As used herein, the term "sample" includes any liquid or fluid sample, including a sample derived from a biological source, such as a physiological fluid, including whole blood or whole blood components, such as red blood cells, white blood cells, platelets, serum and plasma; ascites; urine; saliva; sweat; milk; synovial fluid; peritoneal fluid; amniotic fluid; percerebrospinal fluid; lymph fluid; lung embolism; cerebrospinal fluid; pericardial fluid; cervicovaginal samples; tissue extracts; cell extracts; and other constituents of the body that are suspected of containing the analyte of interest. In addition to physiological fluids, other liquid samples, such as water, food products and the like, for the performance of environmental or food production assays are suitable for use with the presently disclosed subject matter. A solid material suspected of containing the analyte also can be used as the test sample. In some instances it might be beneficial to modify a solid test sample to form a liquid medium or to release the analyte.

In some embodiments, the sample can be pre-treated prior to use, such as preparing plasma from blood, diluting viscous fluids, or the like. Such methods of treatment can involve filtration, distillation, concentration, inactivation of interfering compounds, and the addition of reagents.

The sample can be any sample obtained from a subject. The term "subject" refers to an organism, tissue, or cell from which a sample can be obtained. A subject can include a human subject for medical purposes, such as diagnosis and/or treatment of a condition or disease, or an animal subject for medical, veterinary purposes, or developmental purposes. A subject also can include sample material from tissue culture, cell culture, organ replication, stem cell production and the like. Suitable animal subjects include mammals and avians. The term "avian" as used herein includes, but is not limited to, chickens, ducks, geese, quail, turkeys, and pheasants. The term "mammal" as used herein includes, but is not limited to, primates, e.g, humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. Preferably, the subject is a mammal or a mammalian cell. More preferably, the subject is a human or a human cell. Human subjects include, but are not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. A subject also can refer to cells or collections of cells in laboratory or bioprocessing culture in tests for viability, differentiation, marker production, expression, and the like.

6. Biosensor Kits Comprising Dyes of Formula (I) or Formula (II)

The presently disclosed subject matter further provides a packaged composition such as a kit or other container for detecting, monitoring or otherwise observing a target molecule. The kit or container can hold a biosensor comprising a dye of Formula (I) or Formula (II) and instructions for using the biosensor for detecting, monitoring or otherwise observing a target molecule. The biosensor includes at least one binding member and a dye of Formula (I) or Formula (II). In one embodiment, the kit comprises a container containing a biosensor comprising scFv binding domain and a dye. Alternatively, the kit or container holds a dye of Formula (I) or Formula (II) and instructions for using the dye. In some embodiments, kits containing dyes can contain instructions for attaching a dye to a binding domain selected by one of skill in the art.

The presently disclosed kits also can comprise containers with solutions or tools useful for manipulating or using the presently disclosed dyes or biosensors. Such tools include buffers, reaction tubes, reagents for coupling dyes of Formula (I) or Formula (II) to selected binding domains and the like. In one embodiment, the kit can contain a solution of solvents and/or buffers to facilitate coupling of a dye of Formula (I) or Formula (II) to a selected binding domain and/or a solution of mercaptoethanol for quenching the dye-binding domain conjugation reaction. The kit also can include a container of buffer at roughly neutral pH (e.g., sodium phosphate buffer, pH 7.5).

II. Chemical Definitions

While the following terms are believed to be well understood by one of ordinary skill in the art, the following definitions are set forth to facilitate explanation of the presently disclosed subject matter. Unless otherwise defined, all technical and scientific terms used herein have the same meaning as commonly understood by one of ordinary skill in the art to which this presently described subject matter belongs.

Throughout the specification and claims, a given chemical formula or name shall encompass all optical and stereoisomers, as well as racemic mixtures where such isomers and mixtures exist.

When the term "independently selected" is used, the substituents being referred to (e.g., R groups, such as groups $R_1$, $R_2$, and the like, or groups $X_1$ and $X_2$), can be identical or different. For example, both $R_1$ and $R_2$ can be substituted alkyls, or $R_1$ can be hydrogen and $R_2$ can be a substituted alkyl, and the like.

A named "R" or "X" group will generally have the structure that is recognized in the art as corresponding to a group having that name, unless specified otherwise herein. For the purposes of illustration, certain representative "R" and "X" groups as set forth above are defined below. These definitions are intended to supplement and illustrate, not preclude, the definitions that would be apparent to one of ordinary skill in the art upon review of the present disclosure.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, such as a 3- to 7-member substituted or unsubstituted cycloalkyl ring system, including one or more heteroatoms, which can be the same or different, and are selected from the group consisting of N, O, and S, and optionally can include one or more double bonds. The cycloheteroalkyl ring can be optionally fused to or otherwise attached to other cycloheteroalkyl rings and/or non-aromatic hydrocarbon rings. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The term "alkenyl" as used herein refers to a straight or branched hydrocarbon of a designed number of carbon atoms containing at least one carbon-carbon double bond. Examples of "alkenyl" include vinyl, allyl, 2-methyl-3-heptene, and the like.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a straight or branched hydrocarbon of a designed number of carbon atoms containing at least one carbon-carbon triple bond. Examples of "alkynyl" include propargyl, propyne, and 3-hexyne.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—($CH_2$)$_3$—); cyclohexylene (—$C_6H_{10}$—); —CH=CH—CH=CH—; —CH=CH—$CH_2$—; —($CH_2$)$_q$—N(R)—($CH_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—($CH_2$)$_2$—O—). An alkylene group can have about 2 to about 3 carbon atoms and can further have 6-20 carbons.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "heteroaryl" refers to an aromatic ring system, such as, but not limited to a 5- or 6-member ring system, including one or more heteroatoms, which can be the same or different, and are selected from the group consisting of N, O, and S. The heteroaryl ring can be fused or otherwise attached to one or more heteroaryl rings, aromatic or non-aromatic hydrocarbon rings, or heterocycloalkyl rings. Representative heteroaryl ring systems include, but are not limited to, pyridyl, pyrimidyl, pyrrolyl, pyrazolyl, azolyl, oxazolyl, isoxazolyl, oxadiazolyl, thiazolyl, isothiazolyl, imidazolyl, furanyl, thienyl, quinolinyl, isoquinolinyl, indolinyl, indolyl, benzothienyl, benzothiazolyl, enzofuranyl, benzimidazolyl, benzisoxazolyl, benzopyrazolyl, triazolyl, tetrazolyl, and the like.

A structure represented generally by the formula, wherein the ring structure can be aromatic or non-aromatic:

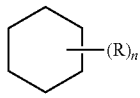

as used herein refers to a ring structure, for example, but not limited to a 3-carbon, a 4-carbon, a 5-carbon, a 6-carbon, and the like, aliphatic and/or aromatic cyclic compound, including a saturated ring structure, a partially saturated ring structure, and an unsaturated ring structure as defined herein, comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure above where n is 0 to 2 would comprise compound groups including, but not limited to:

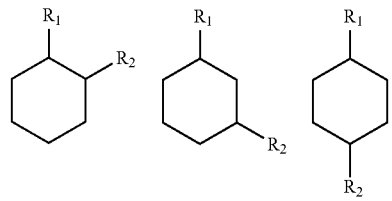

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

When a named atom of an aromatic ring or a heterocyclic aromatic ring is defined as being "absent," the named atom is replaced by a direct bond.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Alkoxyl" refers to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

The term "alkyl-thio-alkyl" as used herein refers to an alkyl-S-alkyl thioether, for example, a methylthiomethyl or a methylthioethyl group.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl. "Aryloxycarbonyl" refers to an aryl-O—CO— group. Exemplary aryloxycarbonyl groups include phenoxy- and naphthoxy-carbonyl. Aralkoxycarbonyl" refers to an aralkyl-O—CO— group. An exemplary aralkoxycarbonyl group is benzyloxycarbonyl.

"Carbamoyl" refers to an $H_2N$—CO— group. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

The term "alkylamino" refers to an —NHR group wherein R is an alkyl group and/or a substituted alkyl group as previously described. Exemplary alkylamino groups include methylamino, ethylamino, and the like.

"Dialkylamino" refers to an —NRR' group wherein each of R and R' is independently an alkyl group and/or a substituted alkyl group as previously described. Exemplary dialkylamino groups include ethylmethylamino, dimethylamino, and diethylamino.

"Acylamino" refers to an acyl-NH— group wherein acyl is as previously described. "Aroylamino" refers to an aroyl-NH— group wherein aroyl is as previously described.

A "quaternary nitrogen atom," is a pentavalent nitrogen atom bound to four atoms, for example, four carbon atoms, and having a positive charge available for binding ionically to an anion for the remaining valence. A quaternary nitrogen atom is designated herein as "$N^+$."

The term "carbonyl" refers to the —(C=O)— group.
The term "carboxyl" refers to the —COOH group.
The term "cyano" refers to the —C≡N group.
The terms "halo", "halide", or "halogen" as used herein refer to fluoro, chloro, bromo, and iodo groups.
The term "hydroxyl" refers to the —OH group.
The term "hydroxyalkyl" refers to an alkyl group substituted with an —OH group.
The term "mercapto" refers to the —SH group.
The term "oxo" refers to a compound described previously herein wherein a carbon atom is replaced by an oxygen atom.
The term "nitro" refers to the —$NO_2$ group.
The term "thio" refers to a compound described previously herein wherein a carbon or oxygen atom is replaced by a sulfur atom.
The term "sulfate" refers to the —$SO_4$ group.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Characterization of Cyano-Substituted S-SO and I-SO Merocyanine Dyes

The photophysical and photochemical properties of I-SO-CN and S-SO-CN were compared with those of the unsubstituted analogues I-SO and S-SO (see Table 2). Solutions of I-SO, S-SO, I-SO-CN and S-SO-CN dyes were irradiated by a halogen tungsten lamp (150 W). Absorption spectra of the solutions were recorded at different times to monitor dye photobleaching. As indicated by the data provided in Table 2, the cyano group improved the photostability of the dyes. Photobleaching followed first-order kinetics for all dyes. Rate constants were obtained from a plot of lnC vs. time (see FIGS. 1-3, Table 2).

Referring now to FIGS. 1A and 1B, the relative photobleaching rates of I-SO and I-SO-CN dyes are illustrated. FIG. 1A shows the normalized absorbance decay vs. illumination time of I-SO and I-SO-CN dyes. FIG. 1B shows the first-order kinetics of photobleaching for I-SO and I-SO-CN dyes. Referring now to FIGS. 2A-2D, the relative photobleaching rates of S-SO and S-SO-CN is illustrated. FIG. 2A shows the normalized absorbance decay vs. illumination time of S-SO and S-SO-CN dyes. FIG. 2B shows first-order kinetics of photobleaching for S-SO and S-SO-CN dyes. FIG. 2C shows first-order kinetics of photobleaching for S-SO dye. FIG. 2D shows first-order kinetics of photobleaching for S-SO-CN dye. FIG. 3 shows the absorbance decay of I-SO, S-SO, I-SO-CN, and S-SO-CN.

The dyes having cyano groups substituted on the first carbon of the central polymethine chain were more photostable than their unsubstituted counterparts. Cyano substitution, e.g, dyes I-SO-CN and S-SO-CN, decreased photobleaching rates for I-SO and S-SO dyes by 5.5- and 39-fold, respectively. Introduction of the cyano-group suppressed the extinction coefficients of the dyes in methanol by 34% (S-SO) and 62% (I-SO), and led to hypsochromic shifts, i.e., a shift to shorter wavelength (higher frequency), of both absorption (about 55 nm) and emission (about 20 nm) wavelength maxima. The fluorescence quantum yields in methanol were unaffected for both dyes.

TABLE 2

Photobleaching Rates of Cyano-substituted Dyes and Their Unsubstituted Analogs (in Methanol).

| Dye | Absorbance $\lambda_{max}$/nm ($\epsilon^a$) | Emission $\lambda_{max}$/nm | $\Phi^b$ | Photo- bleaching Rate, $s^{-1}$ | Relative Photo- bleaching Rates | Decrease in Photobleaching (CN vs. H) |
|---|---|---|---|---|---|---|
| I-SO | 586 (143000)$^c$ | 615 | 0.03 | $1.33 \times 10^{-6}$ | 9.85 | N/A |
|  | 587 (134000)$^d$ | 618 | 0.2 |  |  |  |
| S-SO | 598 (143000)$^c$ | 617 | 0.05 | $5.23 \times 10^{-6}$ | 38.7 | N/A |
|  | 604 (163000)$^d$ | 622 | 0.12 |  |  |  |
| I-SO-CN | 528 (55000)$^c$ | 595 | 0.03 | $0.242 \times 10^{-6}$ | 1.79 | 5.50 |
|  | 527 (56000)$^d$ | 594 | 0.04 |  |  |  |

TABLE 2-continued

Photobleaching Rates of Cyano-substituted Dyes and Their Unsubstituted Analogs (in Methanol).

| Dye | Absorbance $\lambda_{max}$/nm ($\epsilon^a$) | Emission $\lambda_{max}$/nm | $\Phi^b$ | Photo-bleaching Rate, s$^{-1}$ | Relative Photo-bleaching Rates | Decrease in Photobleaching (CN vs. H) |
|---|---|---|---|---|---|---|
| S-SO-CN | 547 (95000)$^c$ | 597 | 0.05 | 0.135 × 10$^{-6}$ | 1.00 | 38.7 |
|  | 550 (91000)$^d$ | 599 | 0.16 |  |  |  |

$^a$Extinction coefficient.
$^b$Fluorescence quantum yield.
$^c$Methanol (MeOH).
$^d$Butanol (BuOH).

Example 2

Characterization of Cyano-Substituted AI Merocyanine Dyes

The approach disclosed in the present example is to increase the contribution of the charged form in the ground state of the dye by using a strong donor, e.g., 10H-pyrido[1,2-a]indolium. A representative 10H-pyrido[1,2-a]indolium compound is 8,10,10-trimethyl-10H-pyrido[1,2-a]indolium, the structure of which is shown below:

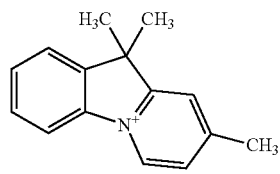 [SMILES: Cc1cc[n+]2c(c1)C(C)(C)c1ccccc1-2]

8,10,10-trimethyl-10H-pyrido[1,2-a]indolium

The ground states of the merocyanine dyes having this donor exist predominately in the polar form. See Scheme 5 and Scheme 6. The polar, zwitterionic form of the dyes in the ground state is stabilized because of the restored aromaticity of the pyridine ring.

Scheme 5. Structure of ground states of the presently disclosed dyes.

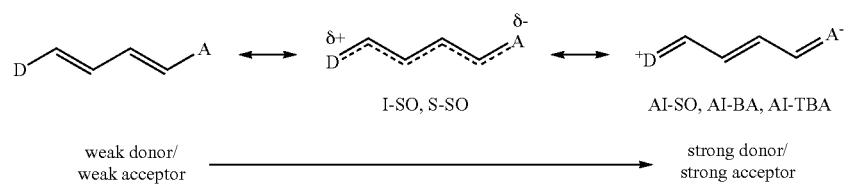

Scheme 6. Ground state of polar merocyanine dyes.

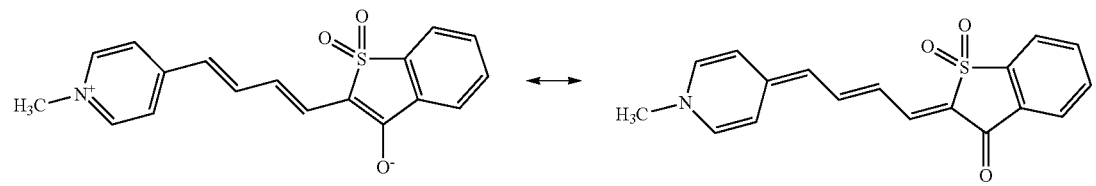

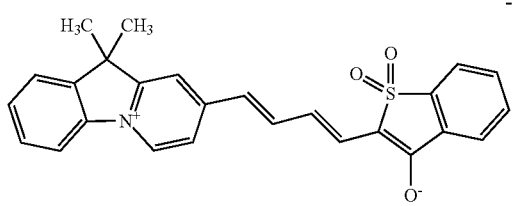

dipolar, aromatic

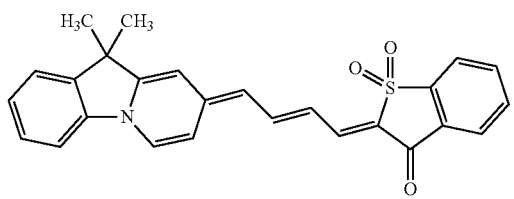

neutral, non-aromatic

Dyes having a 10H-pyrido[1,2-a]indolium donor exhibit a strongly solvent sensitive absorption and emission. See Table 3. One advantage of merocyanine dyes based on a 10H-pyrido[1,2-a]indolium heterocycle is that such dyes exhibit large fluorescence quantum yields even in polar solvents. In contrast, dyes based on other strong donor heterocycles, e.g., 1,4-methylpyridinium, have very low fluorescence quantum yields even though they are strongly solvent sensitive.

The presence of a strong donor can be useful for making the absorption and/or fluorescence of the presently disclosed AI-SO-CN, AI-BA-CN, and AI-TBA-CN). The presently disclosed dyes are solvent-sensitive and photostable.

For example, a cyano-substituted AI-SO-CN is about 45 times more photostable than an unsubstituted AI-SO. Referring now to FIGS. 4A and 4B, the relative photobleaching rates of AI-SO and AI-SO-CN dyes are illustrated. FIG. 4A shows the normalized absorbance decay vs. illumination time. FIG. 4B shows first-order kinetics of photobleaching for AI-SO and AI-SO-CN dyes.

TABLE 3

Photobleaching Rates of Cyano-Substituted AI Dyes and Their Unsubstituted Analogs.

| Dye | Absorbance $\lambda_{max}$/nm ($\epsilon^a$) | Emission $\lambda_{max}$/nm | $\Phi^b$ | Photo-bleaching Rate, s$^{-1}$ | Relative Photo-bleaching Rates | Decrease in Photobleaching (CN vs. H) |
|---|---|---|---|---|---|---|
| AI-BA | 585 (83000)$^c$ | 618 | 0.52 | | | |
|  | 615 (154000)$^d$ | 654 | 0.29 | | | |
| AI-TBA | 576 (38000)$^c$ | —$^f$ | —$^f$ | | | |
|  | 619 (53000)$^d$ | —$^f$ | —$^f$ | | | |
| AI-SO | 610 (65000)$^c$ | 654 | 0.54 | 167 × 10$^{-6}$ | 1240 | N/A |
|  | 650 (118000)$^d$ | 675 | 0.92 | | | |
| AI-BA-CN | 578 (123000)$^e$ | 607 | 0.15 | | | |
|  | 589 (180000)$^c$ | 613 | 0.05 | | | |
|  | 600 (189000)$^d$ | 620 | 0.25 | | | |
| AI-TBA-CN | 593 (77000)$^e$ | 625 | 0.17 | | | |
|  | 606 (146000)$^c$ | 632 | 0.22 | | | |
|  | 621 (188000)$^d$ | 641 | 0.33 | | | |
| AI-SO-CN | 601 (128000)$^e$ | 624 | 0.08 | 3.78 × 10$^{-6}$ | 28 | 44.3 |
|  | 608 (163000)$^c$ | 624 | 0.08 | | | |
|  | 619 (168000)$^d$ | 640 | 0.29 | | | |

$^a$Extinction coefficient.
$^b$Fluorescence quantum yield.
$^c$Methanol (MeOH).
$^d$Butanol (BuOH).
$^e$Water-Methanol (H$_2$O—MeOH).
$^f$Not determined because of dye decomposition.

dyes solvent-sensitive and also makes the dyes less photostable. The AI dyes are much less photostable than I-SO because the α-carbon of the polymethine chain, i.e., the location of primary singlet oxygen attack on the dye, has more electron density in AI-SO or AI-BA dyes than in I-SO. The present example discloses a method for increasing the photostability of dyes by inhibiting dye reaction with singlet oxygen through substitution with a cyano-group at the α-carbon.

The present example uses this strategy to prepare cyano-substituted analogs of AI-SO, AI-BA, and AI-TBA dyes (e.g., Example 3

Characterization of Fluorine-Substituted AI Merocyanine Dyes and Cy5 Dyes

In some embodiments, a double bond of the polymethine chain can be substituted with fluorine to protect the double bond from reaction with singlet oxygen. Fluorine is an electronegative atom that reduces electron density on the double bond, thereby making the bond less susceptible to attack by singlet oxygen. Representative fluorinated analogs of Cy5 and AI-SO dyes, e.g., Cy5-F and AI-SO-F, are provided in Table 1. The fluorinated analogs of Cy5 and AI-SO showed improved photostability as compared to the unsubstituted dyes (see Table 4).

TABLE 4

Photobleaching Rates of Fluorine-substituted Dyes and Their Unsubstituted Analogs.

| Dye | Photobleaching Rate, s$^{-1}$ | Relative Photobleaching Rates | Decrease in Photobleaching (F vs. H) |
|---|---|---|---|
| AI-SO | 167 × 10$^{-6}$ | 45 | N/A |
| AI-SO-F | 17.1 × 10$^{-6}$ | 4.6 | 9.8 |
| Cy-5 | 3.75 × 10$^{-6}$ | 1.00 | N/A |
| Cy-5-F | 1.75 × 10$^{-6}$ | 0.47 | 2.2 |

Referring now to FIGS. 5A and 5B, the photobleaching of Cy5 and Cy5-F and AI-SO and AI-SO-F dyes is illustrated. FIG. 5A shows the normalized absorbance decay vs. illumination time for Cy5 and Cy5-F. FIG. 5B shows the normalized absorbance decay vs. illumination time for AI-SO(4) and AI-SO(4)-F.

Example 4

Photobleaching of S-SO, I-SO, S-SO-CN, I-SO-CN Dyes in the Presence of Photosensitizer (Methylene Blue)

The reactivity of the dyes with singlet oxygen also was examined to confirm that the cyano substituent group affected photobleaching mediated by singlet oxygen. Singlet oxygen was generated using the photosensitizer Methylene Blue (MB), which has a high quantum yield for singlet oxygen production and allows singlet oxygen to be introduced into the system without excitation of the merocyanine dye. See Murov and Carmichael, *Handbook of Photochemistry*, 2nd ed.; Dekker: New York (1993).

15 mL of a methanol solution containing dye (3.33 µM) and Methylene Blue (3.33 µM) were placed in a 20-mL Borosilicate Glass Scintillation Vial (Fisher Scientific). The vial was illuminated with the light of a 90 W halogen reflector lamp (120 V, 1280 Lumens, 12 Degree Beam Spread). To avoid direct excitation of the dye and to permit selective excitation of MB, light was filtered through a methanol solution containing 6.67 µM of each of the dyes: I-SO, S-SO, I-SO-CN, and S-SO-CN. The length of the filtering solution was 1.0 cm. The distance between the vial and the lamp was 11.0 cm. A fan (120 V, 150 mm)) was used to cool the vial. At selected time intervals a sample was removed and the sample absorbance spectrum was obtained on a Hewlett-Packard 8453 diode array spectrophotometer (Agilent, Technologies, Inc.). Rate constants of dye photobleaching were obtained from a plot of ln(A) vs. time (see Table 5).

TABLE 5

Photobleaching of S-SO and S-SO-CN dyes.

| Dye | Time (seconds) | $A_t/A^a_0$ | $-\ln(A_t/A_0)$ |
|---|---|---|---|
| S-SO | 0 | 1.0000 | 0.0000 |
| | 66900 | 0.7409 | 0.3000 |
| | 154200 | 0.4485 | 0.8018 |
| | 258300 | 0.2880 | 1.2448 |
| | 349800 | 0.1560 | 1.8579 |
| S-SO-CN | 0 | 1.0000 | 0.0000 |
| | 66900 | 0.9851 | 0.0150 |
| | 154200 | 0.9790 | 0.0212 |
| | 258300 | 0.9613 | 0.0395 |
| | 349800 | 0.9530 | 0.0481 |

$^a$Absorbances were measured at wavelengths equal to $\lambda_{max}$ (597 nm for S-SO and 550 nm for S-SO-CN).

Figure 6:
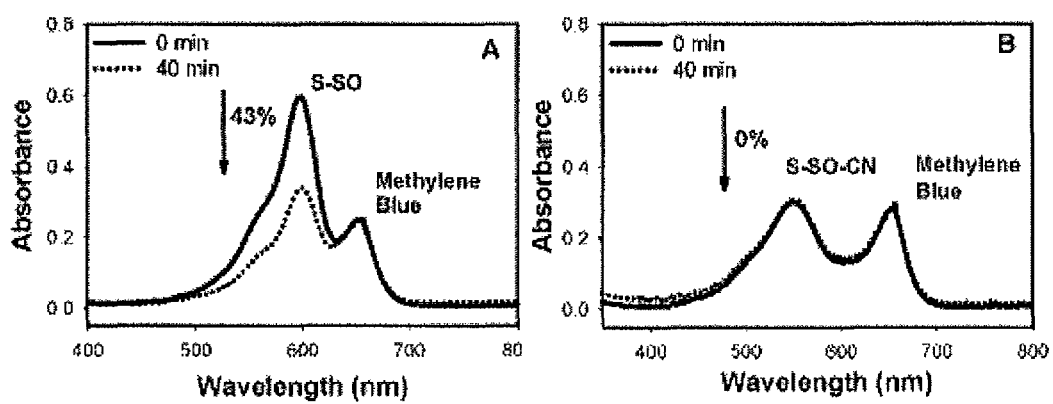

Referring now to FIG. 6, the irradiation of MB resulted in 43 percent bleaching of S-SO, but no bleaching of S-SO-CN. Under the same conditions, I-SO and I-SO-CN dyes showed 27% and 0% bleaching, respectively. These results indicate that substitution of —CN at the first carbon of the central polymethine chain blocks detectable bleaching by singlet oxygen. Again, without wishing to be bound to any one particular theory, the greater reactivity of S-SO vs. I-SO toward singlet oxygen can be attributed to the greater electron donating capacity of the benzothiazole moiety relative to the indolenine ring system.

The relative rates of S-SO and I-SO bleaching are different when bleaching is solely due to singlet oxygen (FIG. 6) or to light (Table 2). The relative bleaching rate, $k_{S-SO}/k_{I-SO}$ was 1.78 in the MB solution, compared to 3.93 for light-induced bleaching (Table 2). This observation likely arises because S-SO produces singlet oxygen more efficiently than I-SO. Heavy atoms, like the additional sulfur in S-SO, increase the probability of singlet-triplet intersystem crossing and promote singlet oxygen formation. See Koziar and Cowan, *Accounts of Chemical Research* 11:334-341 (1978).

Substitution of a cyano group at the central polymethine chain blocked destruction of the dyes by singlet oxygen, yet the cyano-substituted dyes still underwent light-induced bleaching (albeit much more slowly). This light-induced bleaching likely involves a reactive oxygen species other than singlet oxygen, e.g., superoxide. Superoxide has been detected in solutions of cyanine dyes upon illumination with light and is generated by electron transfer from the singlet excited state of the dye to an oxygen molecule. See Clapp and Armitage, *Macromolecules* 30:32-41 (1997); Chen et al., *Dyes and Pigments* 37:213-222 (1998). This mechanism can be facilitated by higher energy excited states and is consistent with the observation that a dye with a shorter excitation wavelength bleaches more rapidly (see Table 2: $k_{S-SO-CN}/k_{I-SO-CN}$=0.56).

Example 4

Synthesis of S-SO-CN and I-SO-CN Dyes 4.1 Materials.

Analytical grade reagents were purchased from Sigma-Aldrich Co. (St. Louis, Mo.). (2Z)-2-[(2E)-3-methoxyprop-2-en-1-ylidene]-1-benzothiophen-3(2H)-one 1,1-dioxide, (2Z)-2-[(2E,4Z)-4-(3-ethyl-1,3-benzothiazol-2(3H)-ylidene)but-2-en-1-ylidene]-1-benzothiophen-3(2H)-one 1,1-dioxide (S-SO), (2Z)-2-[(2E,4E)-4-(1,3,3-trimethyl-1,3-dihydro-2H-indol-2-ylidene)but-2-en-1-ylidene]-1-benzothiophen-3(2H)-one 1,1-dioxide (I-SO) were prepared as described by Toutchkine et al., *J. Am. Chem. Soc.* 125:4132-4145 (2003).

4.2 Methods.

Absorption spectra were recorded on a Hewlett-Packard 8453 diode array UV-Vis spectrophotometer (Agilent Technologies, Inc., Santa Clara, Calif.), and fluorescence measurements were taken on a SPEX® Fluorolog 2 spectrofluorometer (HORIBA Jobin Yvon, Inc., Edison, N.J.). Melting points are not corrected. NMR spectra were obtained on a Varian Mercury 300 MHz (Varian, Inc., Palo Alto, Calif.) or on a Bruker 300 MHz DRX 300 spectrometer (Bruker Biospin Corp., Billerica, Mass.). Mass spectra were obtained on a Hewlett-Packard 1100 high-performance liquid chromatograph equipped with an 1100 mass selective detector (MS-ESI) (Agilent Technologies, Inc.). Quantum yields were measured using merocyanine 540 or Cy5 as internal standards.

4.3 Synthesis Schemes

Referring now to Scheme 7, a scheme for the synthesis of representative S-SO and I-SO dyes having a cyano group at the first carbon, e.g., the α-carbon, of the central polymethine chain (referred to herein as S-SO-CN and I-SO-CN) is provided.

Scheme 7. Synthesis of Cyano-Substituted Dyes S-SO-CN and I-SO-CN.

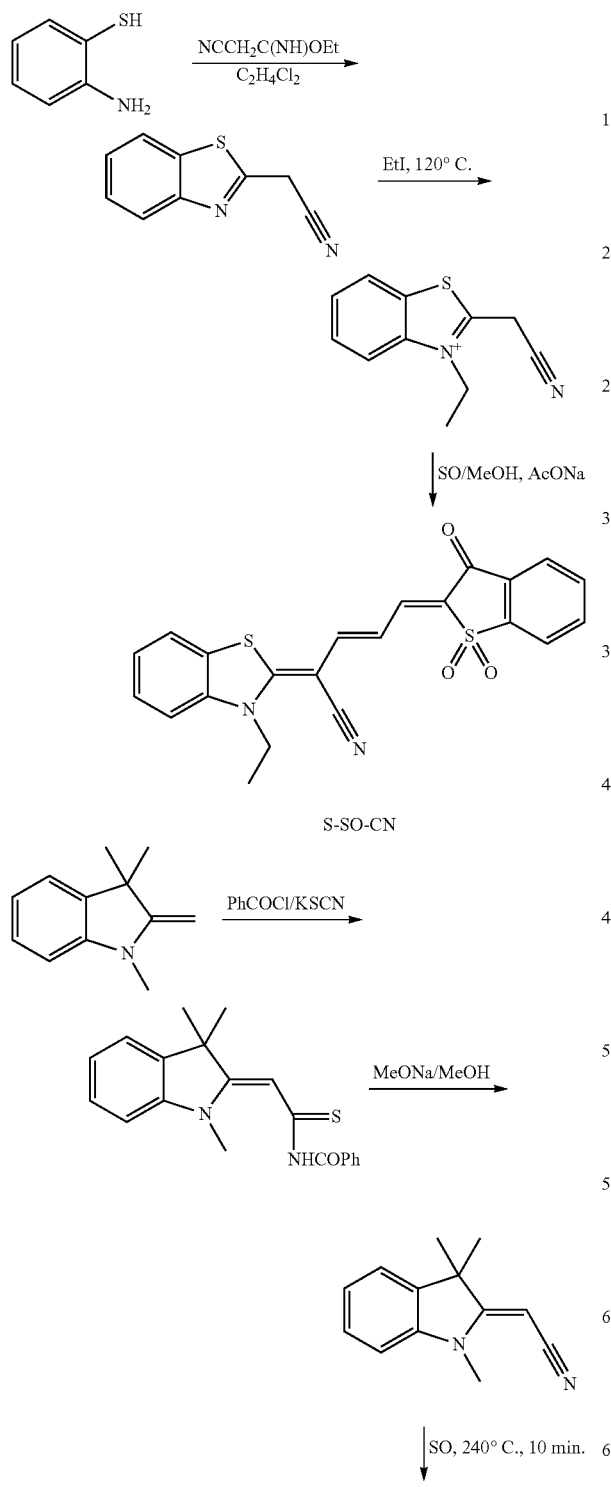

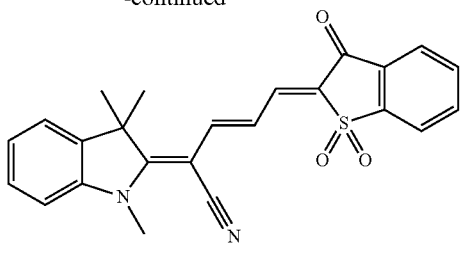

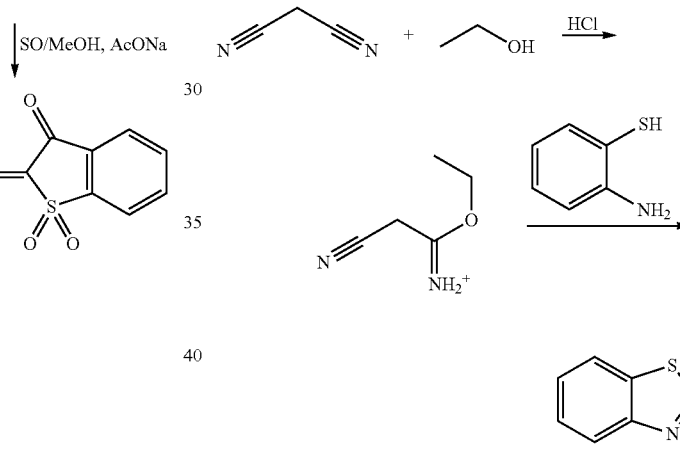

Representative methods for preparing S-SO-CN are provided below.

4.3.1.1 Synthesis of 1,3-benzothiazol-2-ylacetonitrile

To a solution of malonodinitrile (13.22 g, 0.200 mole) in dry chloroform (100 mL) was added ethanol (9.2 g, 0.200 mole). Hydrogen chloride (8.0 g, 0.220 mole) was passed into the solution at room temperature and the resulting suspension was stirred for an additional 16 hours at room temperature. The excess of hydrogen chloride was removed by passing dry nitrogen into the reaction mixture. A solution of o-aminothiophenol (25 g, 0.200 mole) in chloroform was added to the reaction mixture dropwise during 30 min and the reaction mixture was stirred for 1 hour at 60° C. After that the reaction mixture was cooled to room temperature, washed with water (2×100 mL) and dried with magnesium sulfate. Chloroform was removed using a rotary evaporator. The solid residue was recrystallized from ethyl alcohol. White crystals. The yield was 26.1 g (75% of theory). Mp=101-103° C.

$^1$H NMR (CDCl$_3$, 300 MHz) δ 4.24 (s, 2H), 7.44 (t, $^3J_{H-H}$=7.8 Hz, 1H), 7.53 (t, $^3J_{H-H}$=7.8 Hz, 1H), 7.89 (d, $^3J_{H-H}$=7.8 Hz, 1H), 8.04 (d, $^3J_{H-H}$=7.8 Hz, 1H).

$^{13}$C NMR (CDCl$_3$, 75 MHz) δ 22.3, 116.4, 122.2, 122.5, 125.5, 126.4, 135.0, 152.2, 160.4.

4.3.1.2 Synthesis of 2-(cyanomethyl)-3-ethyl-1,3-benzothiazol-3-ium iodide

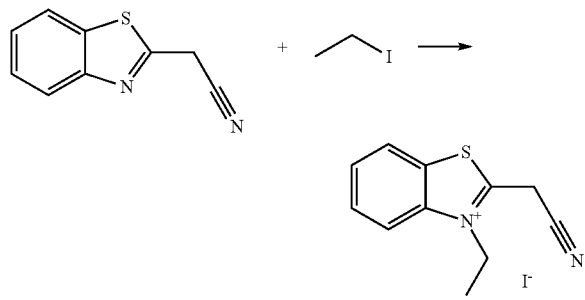

A solution of 1,3-benzothiazol-2-ylacetonitrile (10 g, 0.057 mole) in iodoethane (10 mL, 0.125 mole) was heated in sealed tube at 120° C. for 36 hours. The precipitated solid was filtered, washed with ether (100 mL) and dried. The yield was 10 g (53% of theory).

$^1$H NMR (DMSO-$d_6$, 300 MHz) δ 1.31 (t, $^3J_{H-H}$=7.0 Hz, 3H, CH$_3$CH$_2$—), 3.93 (q, $^3J_{H-H}$=7.0 Hz, 2H, CH$_3$CH$_2$—), 4.76 (s, CH$_2$—CN), 7.09 (t, $^3J_{H-H}$=7.5 Hz, 1H), 7.23 (t, $^3J_{H-H}$=7.5 Hz, 1H), 7.31 (d, $^3J_{H-H}$=7.5 Hz, 1H), 7.58 (d, $^3J_{H-H}$=7.5 Hz, 1H).

$^{13}$C NMR (DMSO-$d_6$, 75 MHz) δ 11.9, 55.1, 111.3, 122.0, 123.2, 123.9, 127.8, 142.2, 162.1.

4.3.1.3. Synthesis of (2E,3E,5Z)-5-(1,1-dioxido-3-oxo-1-benzothien-2(3H)-ylidene)-2-(3-ethyl-1,3-benzothiazol-2(3H)-ylidene)pent-3-enenitrile (S-SO-CN)

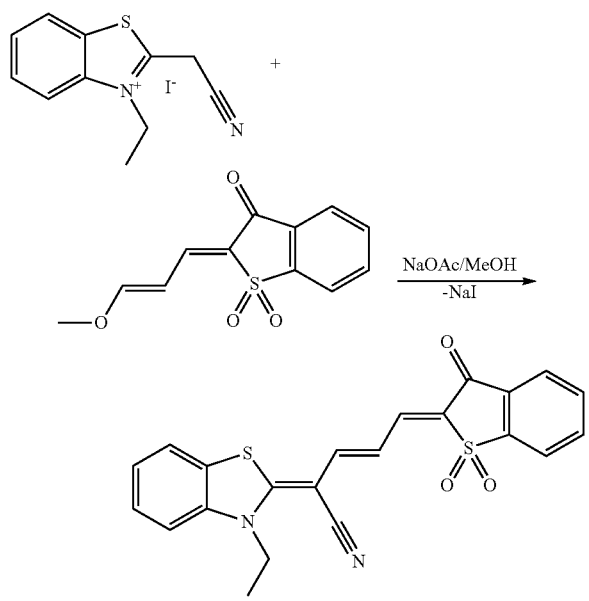

In a one-necked round bottom 100-mL flask equipped with magnetic stir bar and reflux condenser were added 2-(cyanomethyl)-3-ethyl-1,3-benzothiazol-3-ium iodide (1.00 g, 3.03 mmol), (2Z)-2-[(2E)-3-methoxyprop-2-en-1-ylidene]-1-benzothiophen-3-(2H)-one 1,1-dioxide (1.00 g, 4.00 mmol) and CHCl$_3$-MeOH mixture (1:1, 20 mL). The flask was heated on an oil bath with stirring until boiling began, and a solution of sodium acetate (320 mg, 4.00 mmol) in 10 mL of methanol was added to the flask. The stirring was continued under reflux for an additional 30 min. The flask was cooled to room temperature and the precipitated solid was filtered, washed with methanol and dried. Green crystals. The yield was 730 mg (57% of theory).

$^1$H NMR (CDCl$_3$, 300 MHz) δ 1.49 (t, $^3J_{H-H}$=7.2 Hz, 3H), 4.71 (q, $^3J_{H-H}$=7.2 Hz, 2H), 6.78 (t, $^3J_{H-H}$=12.9 Hz, 1H), 7.47 (t, $^3J_{H-H}$=7.5 Hz, 1H), 7.61 (t, $^3J_{H-H}$=7.5 Hz, 1H), 7.8-8.2 (m, 8H).

ESI-MS: 421 (MH$^+$).

4.3.2. Synthesis of I-SO-CN

4.3.1.1 Synthesis of N-[(2Z)-2-(1,3,3-trimethyl-1,3-dihydro-2H-indol-2-ylidene)ethanethioyl]benzamide

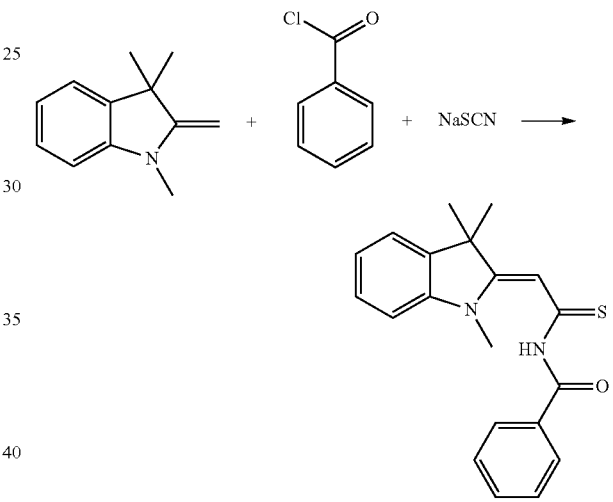

A two-necked round bottom 500-mL flask was equipped with a magnetic stir bar, additional funnel and a reflux condenser. To the flask were added sodium thiocyanate (8.1 g, 0.10 mole) and dry acetone (100 mL). The stirring was started and benzoyl chloride (14.1 g, 0.1 mole) was added to the flask by drops. When the addition of benzoyl chloride was complete the flask was heated on an oil bath with stirring until boiling began and the flask contents were stirred under reflux for an additional 30 minutes. The oil bath was removed and 3,3-trimethyl-2-methyleneindoline (15.8 g, 0.10 mole) was added to the flask by drops. After completion of the addition the flask was heated again on an oil bath for an additional 30 min at reflux. The flask was cooled to room temperature and the reaction mixture was poured in 1-L beaker containing 500 mL of water. The precipitated solid was filtered, washed with water and dried. The product was purified by recrystallization from methanol. The yield was 19.1 g (57% of theory). Mp=108-110° C.

$^1$H NMR (CDCl$_3$, 300 MHz) δ 1.76 (s, 6H), 3.75 (s, 3H), 7.19 (d, $^3J_{H-H}$=7.8 Hz, 1H), 7.31 (t, $^3J_{H-H}$=7.2 Hz, 1H), 7.40-7.46 (m, 2H), 7.60-7.80 (m, 4H), 8.02 (d, $^3J_{H-H}$=6.9 Hz, 2H), 9.31 (s, 1H, NH).

$^{13}$C NMR (CDCl$_3$, 75 MHz) δ 25.8, 37.2, 49.5, 99.2, 110.0, 122.0, 124.1, 127.2, 127.9, 128.7, 132.3, 133.9, 139.8, 144.6, 163.7, 177.4, 185.2.

4.3.2.2 Synthesis of (1,3,3-trimethyl-2,3-dihydro-1H-indol-2-yl)acetonitrile

4.3.2.3 Synthesis of (2Z,3E,5Z)-5-(1,1-dioxido-3-oxo-1-benzothiophen-2(3H)-ylidene)-2-(1,3,3-trimethyl-1,3-dihydro-2H-indol-2-ylidene)pent-3-enenitrile (I-SO-CN)

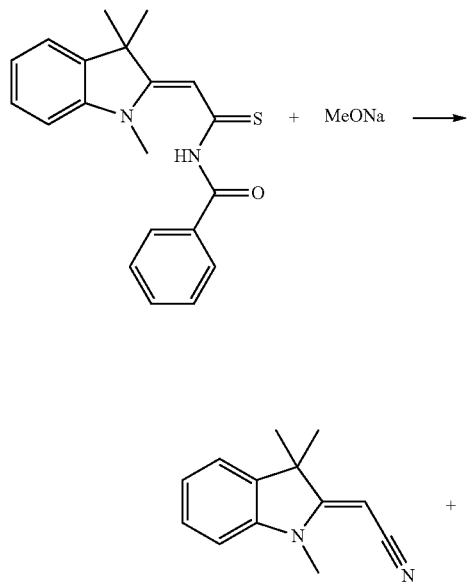

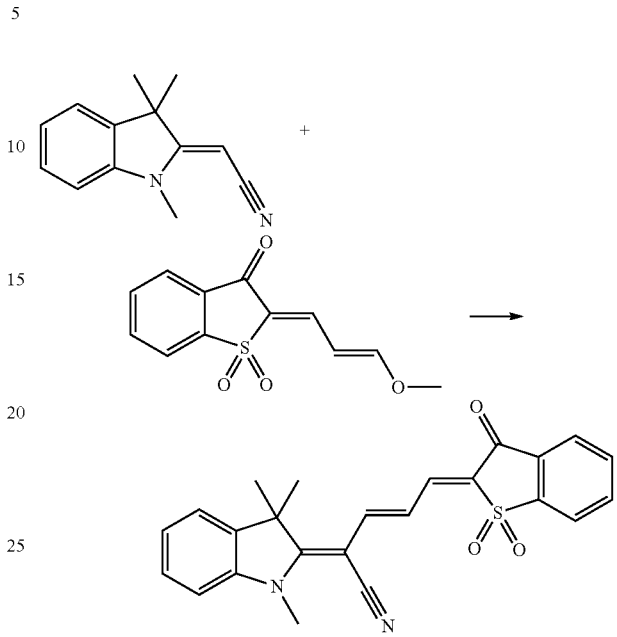

A 500-mL one-necked flask was equipped with a magnetic stir bar and a reflux condenser. 200 mL of methanol were added to the flask, sodium (3.0 g, 0.13 mole) was added to the methanol as small pieces (approximately 0.5 g). After the sodium dissolved, N-[(2Z)-2-(1,3,3-trimethyl-1,3-dihydro-2H-indol-2-ylidene)ethanethioyl]-benzamide (19.0 g, 0.056 mole) was added to the flask and the reaction mixture was heated at reflux with stirring for 2 hours. The reaction mixture was cooled to room temperature and the methanol was evaporated using a rotary evaporator. The residue was treated with 200 mL of water and extracted with dichloromethane (3×100 mL). Combined organic extracts were dried over magnesium sulfate and the solvent was evaporated on a rotary evaporator. The red solid was recrystallized from methanol-water (7:3) to give slightly red crystals. The yield was 4.5 g (40% of theory). Mp=74-76° C.

$^1$H NMR (DMSO-d$_6$, 300 MHz) δ 1.55 (s, 6H, 2*CH$_3$), 3.13 (s, 3H, CH$_3$), 4.48 (s, 1H, CH—CN), 6.85-7.0 (m, 2H), 7.21 (t, $^3J_{H-H}$=7.7 Hz, 1H), 7.31 (d, $^3J_{H-H}$=6.9 Hz, 1H).

$^{13}$C NMR (DMSO-d$_6$, 75 MHz) δ 25.3, 28.9, 46.3, 57.6, 107.4, 120.2, 121.3, 121.7, 137.1, 143.6, 171.9.

A mixture of (1,3,3-trimethyl-2,3-dihydro-1H-indol-2-yl)acetonitrile (397 mg, 2.00 mmol) and (2Z)-2-[(2E)-3-methoxyprop-2-en-1-ylidene]-1-benzothiophen-3(2H)-one 1,1-dioxide (501 mg, 2.00 mmol) were placed in a 10-mL one-necked round bottom flask. The flask was heated in an oil bath at 210° C. for 2 hours and then cooled to room temperature. The reaction mixture was extracted with dichloromethane (100 mL). The organic solution was passed through a short silica column, the dichloromethane was evaporated and the pure dye was obtained by recrystallization from methanol. The yield was 511 mg of green crystals (63% of theory).

$^1$H NMR (CDCl$_3$, 300 MHz) δ 1.68 (s, 6H, 2*CH$_3$), 3.86 (s, 3H, CH$_3$), 6.89 (t, $^3J_{H-H}$=13.1 Hz, 1H), 7.1-8.4 (m, 10H). ESI-MS: 431 (MH$^+$).

Example 5

Synthesis of Dyes Comprising a 10H-pyrido[1,2-a]indolium Donor Moiety

A representative scheme for the synthesis of AI dyes is provided in Scheme 8.

Scheme 8. Synthesis of AI-SO, AI-BA, and AI-TBA dyes.

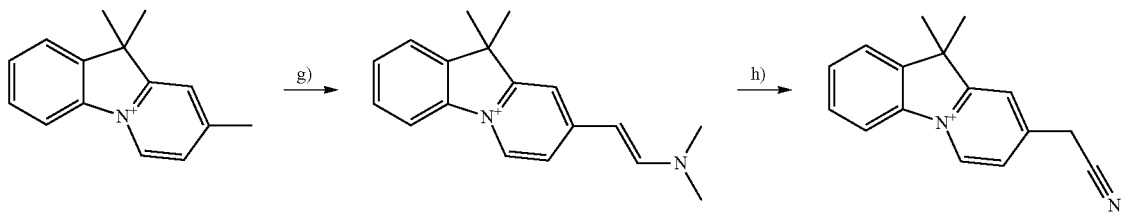

-continued
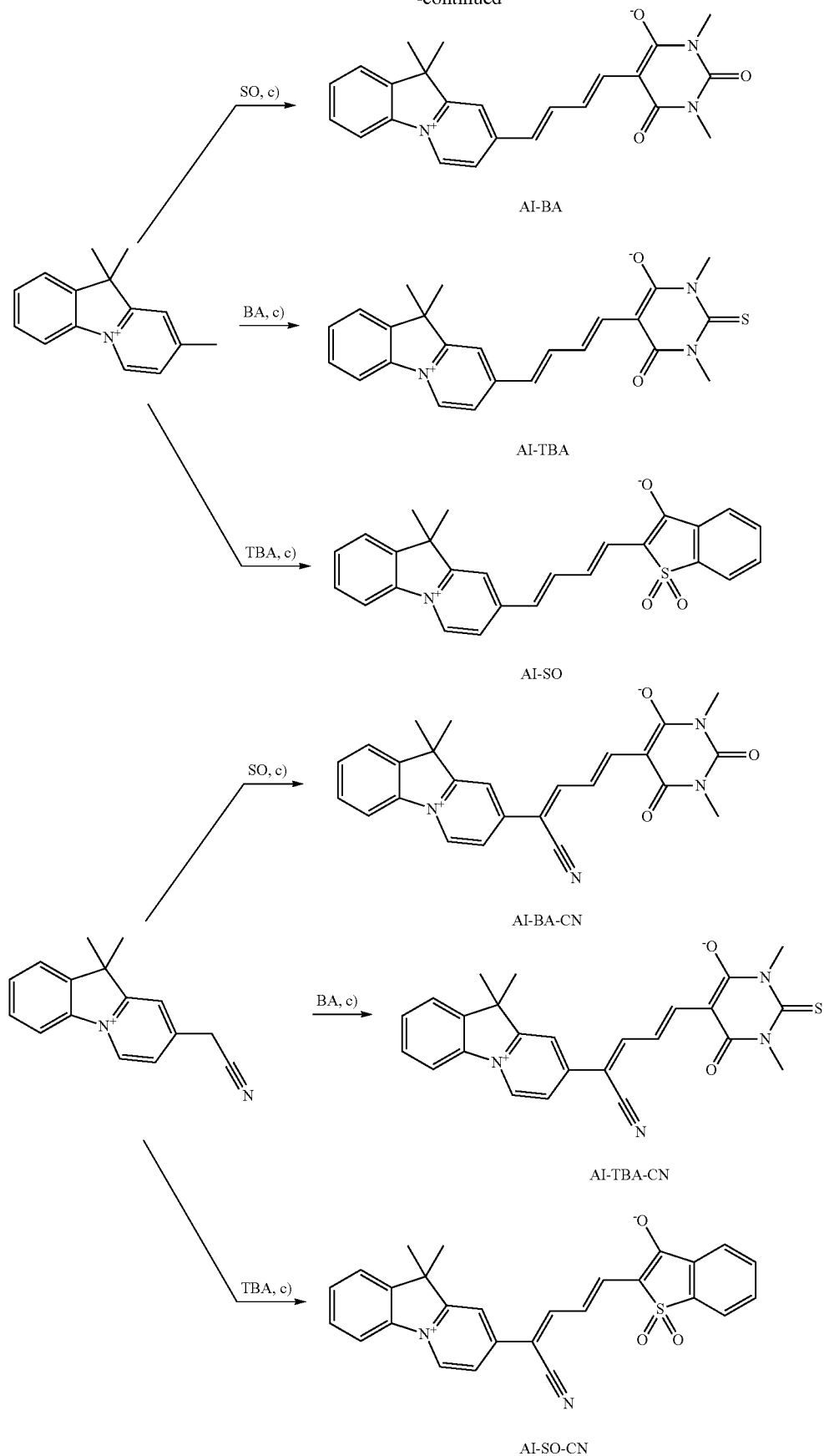

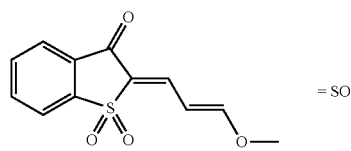 = SO
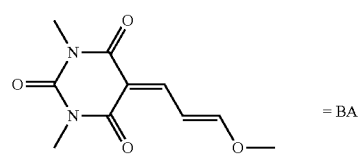 = BA
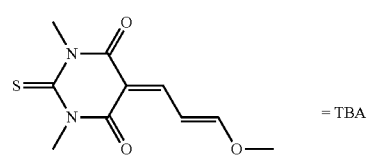 = TBA
A schematic representation of the synthesis of the reactive forms of these dyes is shown in Scheme 9.
Scheme 9. Schematic representation of the synthesis of the reactive forms of AI-BA dyes.
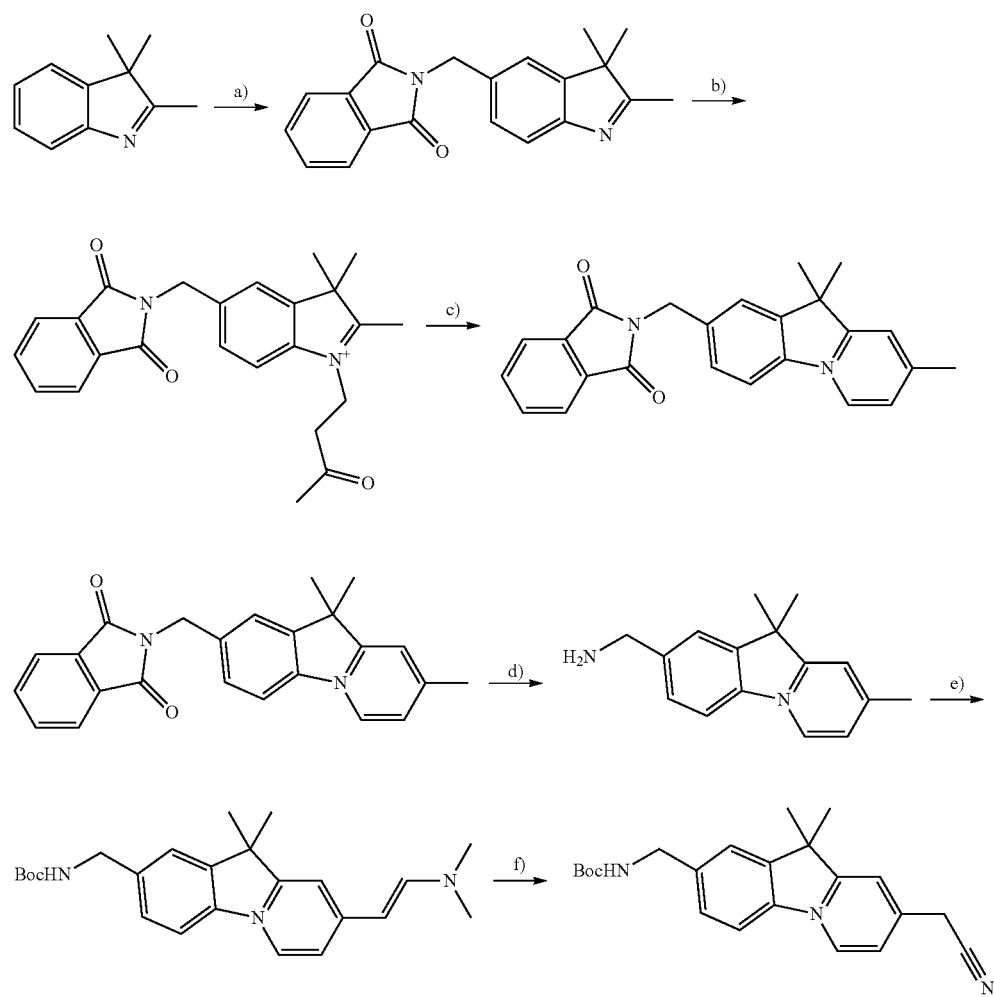

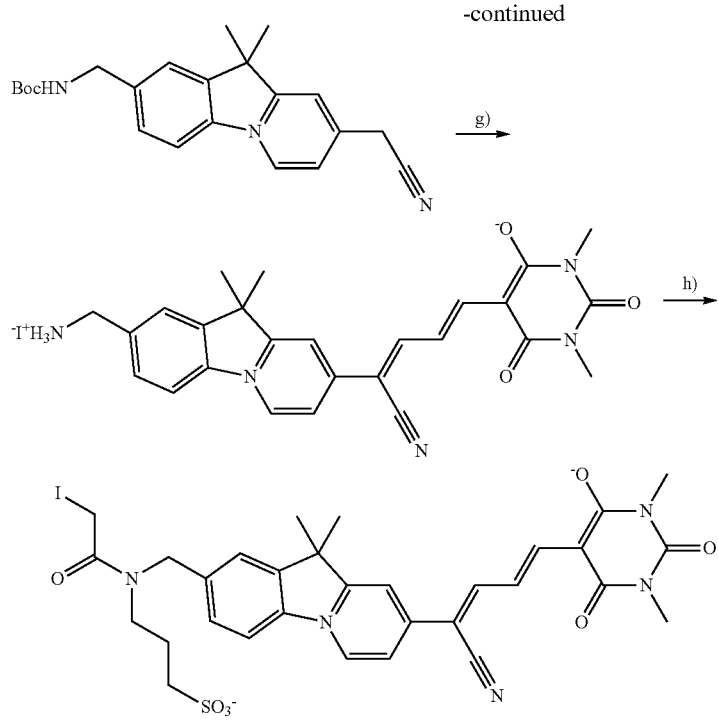

5.1 Synthesis of Intermediate 1

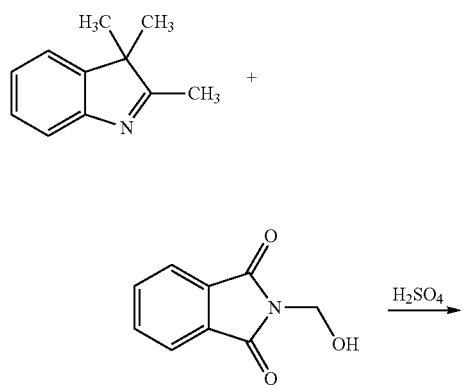

200 mL of sulfuric acid were cooled to 0° C. 48 g of 2,3,3-trimethylindolenine were added to the sulfuric acid followed by the addition of 54 g of N-hydroxymethyl-phthalimide. The reaction mixture was stirred at room temperature for 7 days. The reaction mixture then was added to 500 g of crushed ice in a 2000-mL conical flask immersed in ice-salt bath. A solution of about 225 g of sodium hydroxide in 500 mL of water was cooled to 10° C. and then added dropwise to the magnetically stirred mixture in the conical flask. A white precipitate starts to form after addition of about half of the solution of sodium hydroxide. Addition of the sodium hydroxide is continued until the pH of the reaction mixture is strongly basic (pH>12). The white solid is then filtered, washed with water (3×100 mL) and air-dried on a Buchner funnel for about 1 hour. The solid is then transferred to a 1000-mL one-neck round bottom flask, 300 mL of acetone is added and the mixture is stirred under reflux for 30 min. The flask is then cooled to 10° C. and the white product is filtered with suction on a Buchner funnel, washed with acetone (1×50 mL), and air dried.

The yield of the pure product is 70-75% (67-70 g). NMR: (DMSO-$d_6$, 300 MHz) δ 1.33 (s, 6H, 2×CH$_3$), 2.31 (s, 3H, CH$_3$), 4.91 (s, 2H, CH$_2$), 7.32 (dd, $^3J_{H\text{-}H}$=8.7 Hz, $^5J_{H\text{-}H}$=1.2 Hz, 1H), 7.48 (dd, $^5J_{H\text{-}H}$=8.7 Hz, 1H), 7.51 (dd, $^5J_{H\text{-}H}$=1.2 Hz, 1H, 7.9-8.1 (m, 4H).

5.2 Synthesis of Intermediate 2

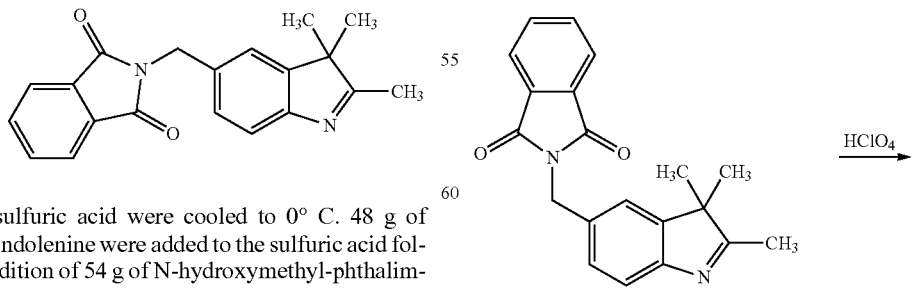

2-[(2,3,3-trimethyl-3H-indol-5-yl)methyl]-1H-isoindole-1,3(2H)-dione

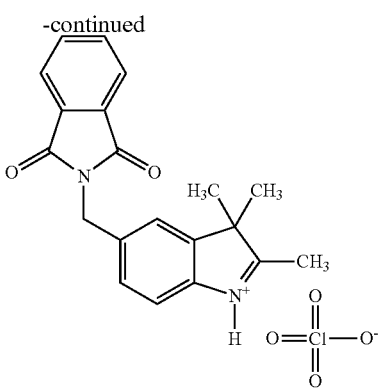

5-[(1,3-dioxo-1,3-dihydro-2H-isoindol-2-yl)
methyl]-2,3,3-trimethyl-3H-indolium perchlorate 63 g of isoindole-dione (0.198 mole) were suspended in 150 mL of ethanol. 17.0 mL of 70% HClO₄ (d=1.67, 5% excess) were added to the suspension and the mixture was then heated at the reflux with strong stirring for 30 min. The mixture was cooled at 10° C. for 1 hour and the solid was filtered and washed with cold ethanol, ether, and dried. The yield was 77.0 g (93%).

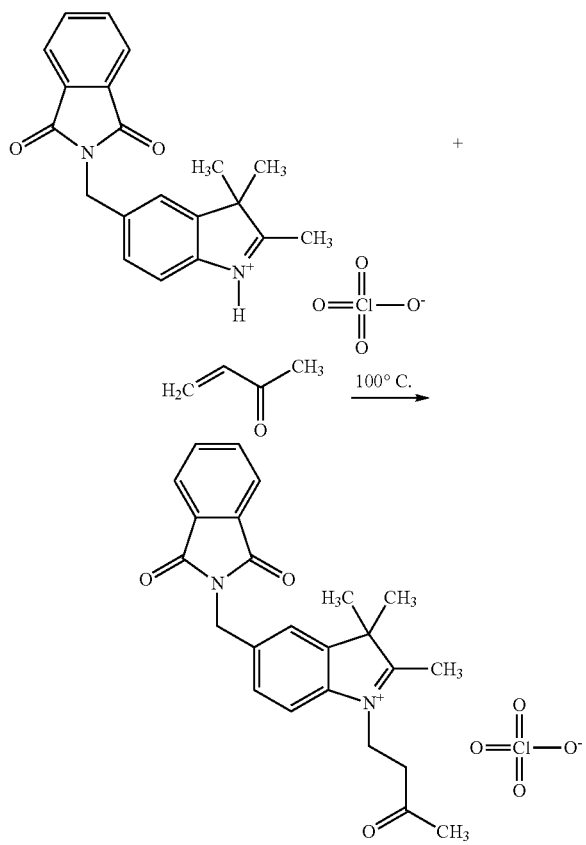

The suspension of 77 g of 5-[(1,3-dioxo-1,3-dihydro-2H-isoindol-2-yl)methyl]-2,3,3-trimethyl-3H-indolium perchlorate in 140 mL of methyl vinyl ketone was heated at 100° C. with stirring until the solution was brought to a boil. The heating was continued for 15 min. The excess of methyl vinyl ketone was removed in vacuum. The residue was dissolved in 200 mL of acetone with heating. Upon cooling (−10° C., 12 hr), the product crystallized. The product was filtered, washed with cold acetone, ether, and dried. The yield was 80.2 g (89%).

NMR: (DMSO-d₆, 300 MHz), δ 1.49 (s, 6H, 2×CH₃), 2.11 (s, 3H, CH₃), 2.82 (s, 3H, CH₃), 3.10 (t, $^3J_{H-H}$=6.6 Hz, 2H, CH₂), 4.54 (t, $^3J_{H-H}$=6.6 Hz, 2H, CH₂), 4.89 (s, 2H, CH₂), 7.55 (dd, $^3J_{H-H}$=8.7 Hz, $^5J_{H-H}$=1.2 Hz, 1H) 7.80 (dd, $^5J_{H-H}$=1.2 Hz, 1H), 7.9-8.1 (m, 5H).

5.3 Synthesis of Intermediate 3

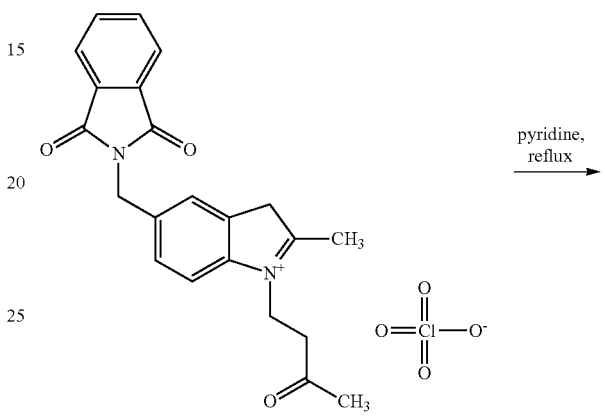

MW = 488.9
5-[(1,3-dioxo-1,3-dihydro-2H-isoindol-2-yl)
methyl]-2,3,3-trimethyl-1-(3-oxobutyl)-
3H-indolium perchlorate

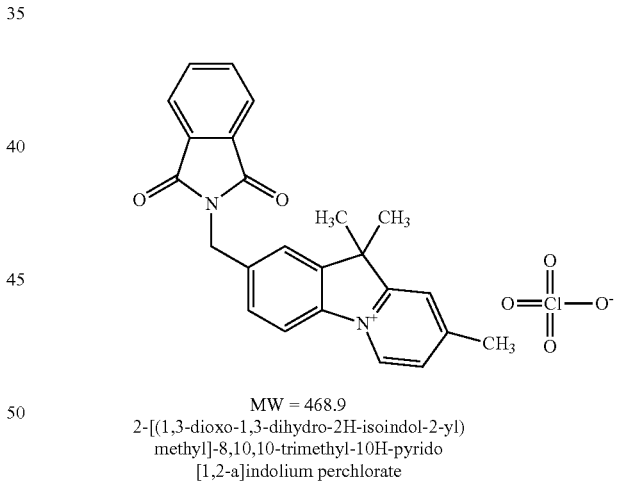

MW = 468.9
2-[(1,3-dioxo-1,3-dihydro-2H-isoindol-2-yl)
methyl]-8,10,10-trimethyl-10H-pyrido
[1,2-a]indolium perchlorate The solution of 79 g of the salt in 200 mL of pyridine was heated at reflux for 1 hour. The pyridine was removed in vacuum. The residue was refluxed with 150 mL of benzene for 20 min. The precipitated solid was filtered. The solid was then stirred with 200 mL of hot EtOH. The suspension was cooled and the crystals were filtered, washed with cold ethanol, ether, and dried. The yield was 41.0 g (54%).

NMR: (DMSO-d₆, 300 MHz), δ 1.66 (s, 6H, 2×CH₃), 2.70 (s, 3H, CH₃), 4.93 (s, 2H, CH₂N), 7.63 (dd, 1H, $^{3a}J_{H-H}$=8.4 Hz and 1.5 Hz), 7.8-8.1 (M, 5H), 8.07 (dd, 1H, $^3J_{H-H}$=6.5 Hz and 1.1 Hz), 8.30 (d, 1H, $^3J_{H-H}$=8.5 Hz), 8.43 (s, 1H), 8.66 (d, 1H, $^3J_{H-H}$=6.5 Hz).

5.4 Synthesis of Intermediate 4

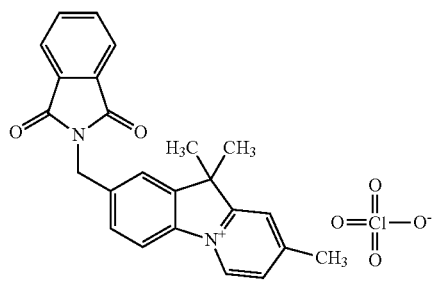

2-[(1,3-dioxo-1,3-dihydro-2H-isoindol-2-yl)methyl]-8,10,10-trimethyl-10H-pyrido[1,2-a]indolium

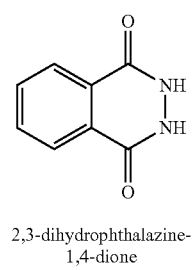

2,3-dihydrophthalazine-1,4-dione

+

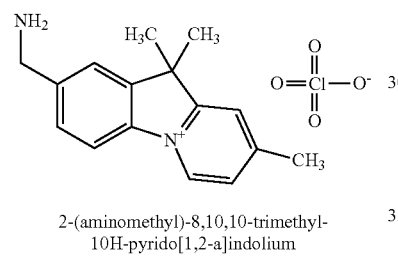

2-(aminomethyl)-8,10,10-trimethyl-10H-pyrido[1,2-a]indolium

Dissolved 15 g of pyrido[1,2-a]indolium salt in 200 mL of $CH_2Cl_2$—$CH_3OH$ mixture (120:80). Added 5.05 g of hydrazine hydrate. Stirred the mixture at room temperature for 24 hr. The separated hydrazide was filtered off and washed with dichloromethane-methanol (30 mL 1:1). The combined filtrate solution was evaporated in vacuum, the solid was stirred with ether (100 mL) and filtered. Then the solid was washed with hot benzene (50 mL) and dried. The yield of crude amine was 10 g (100% yield).

NMR: (DMSO-$d_6$, 300 MHz), δ 1.67 (s, 6H, 2×$CH_3$), 2.71 (s, 3H, $CH_3$), 3.89 (s, 2H, $CH_2$), 7.66 (dd, $^3J_{H-H}$=8.4 Hz, $^3J_{H-H}$=1.2 Hz, 1H), 7.85 (d, $^3J_{H-H}$=1.2 Hz, 1H), 8.07 (dd, $^3J_{H-H}$=6.3 Hz, $^3J_{H-H}$=1.2 Hz, 1H) 8.27 (d, $^3J_{H-H}$=8.4 Hz, 1H), 8.44 (s, 1H), 9.64 (d, $^3J_{H-H}$=6.3 Hz, 1H).

5.5 Synthesis of Intermediate 5

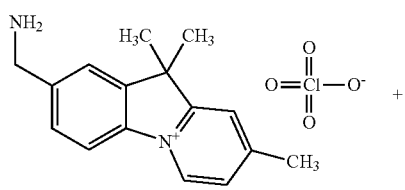

Intermediate 4

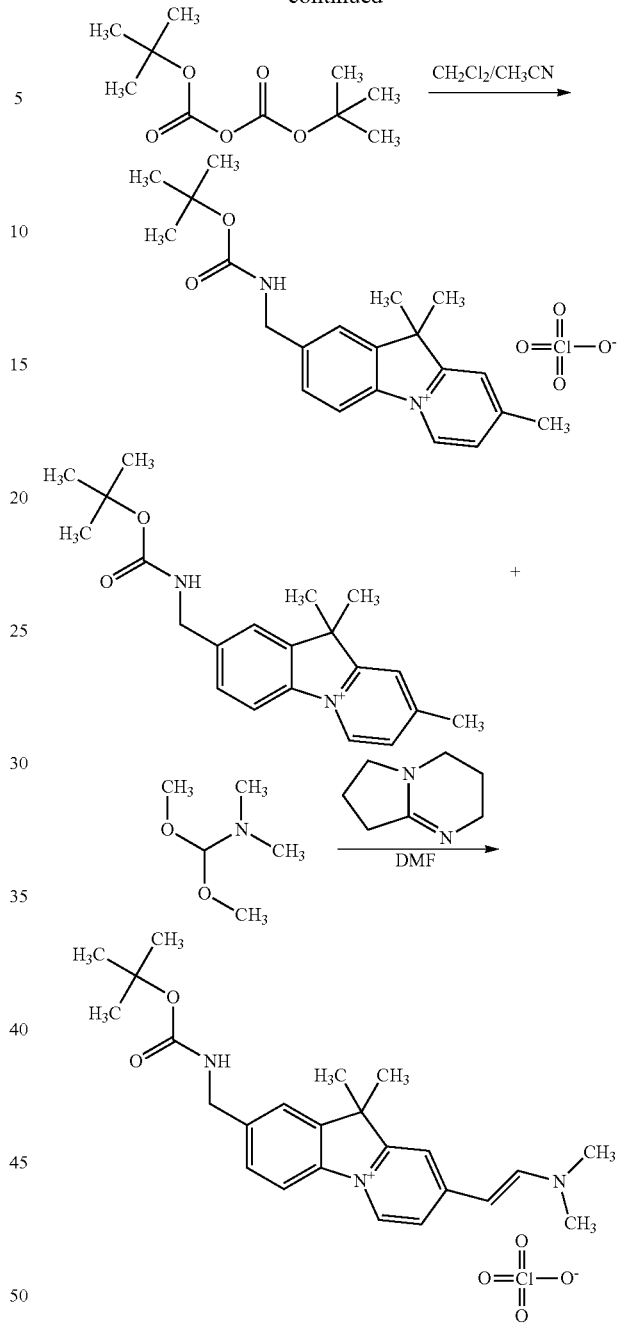

Intermediate 5

Step 1. To the suspension of 5.4 g of intermediate 4 in 100 mL of a 3:1 mixture of $CH_2Cl_2$—$CH_3CN$ were added 1.65 g of $Et_3N$ followed by 3.5 g of t-butyl-pyrocarbonate. The stirring was continued for 24 hours. The solvent was removed in vacuum and the crude protected amine was used in the step 2 without purification.

Step 2. The oily product from step 1 immediately hereinabove was dissolved in 15 mL of dimethylformamide. 8.0 mL of dimethylformamide dimethylacetal were added to the solution, followed by 20 mg (2 drops) of 1,5-diazabicyclo[4.3.0]non-5-ene. The mixture was heated with stirring at 100° C. for 30 min, then cooled. The dimethylformamide was evaporated in vacuum. The residue was recrystallized from MeOH. The yield was 4.0 g (51%).
NMR (300 MHz DMSO-$d_6$): δ1.44 (s, 9H, 3×CH$_3$), 1.57 (s, 6H, 2×CH$_3$), 3.00 (s, 3H, CH$_3$), 3.26 (s, 3H, CH$_3$), 4.22 (d, 2H, $^3J_{H-H}$=6.0 Hz, CH$_2$N), 5.46 (d, 1H, $^3J_{H-H}$=12.6 Hz), 7.39 (dd, 1H, $^3J_{H-H}$=8.4 and 1.0 Hz), 7.2-8.0 (bs, 2H), 7.49 (t, 1H, $^3J_{H-H}$=6.0 Hz, NH), 7.55 (d, 1H, $^3J_{H-H}$=1.2 Hz), 7.94 (d, 1H, $^3J_{H-H}$=8.4 Hz), 8.22 (d, 1H, $^3J_{H-H}$=12.6 Hz), 8.84 (d, 1H, $^3J_{H-H}$=7.2 Hz).
5.6 Synthesis of Intermediate 6
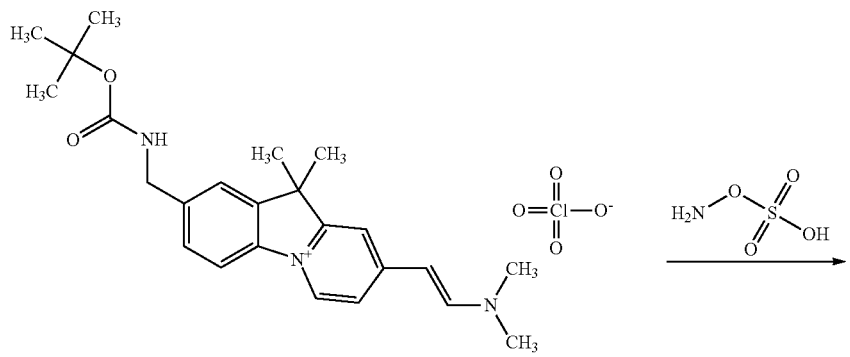
Intermediate 5
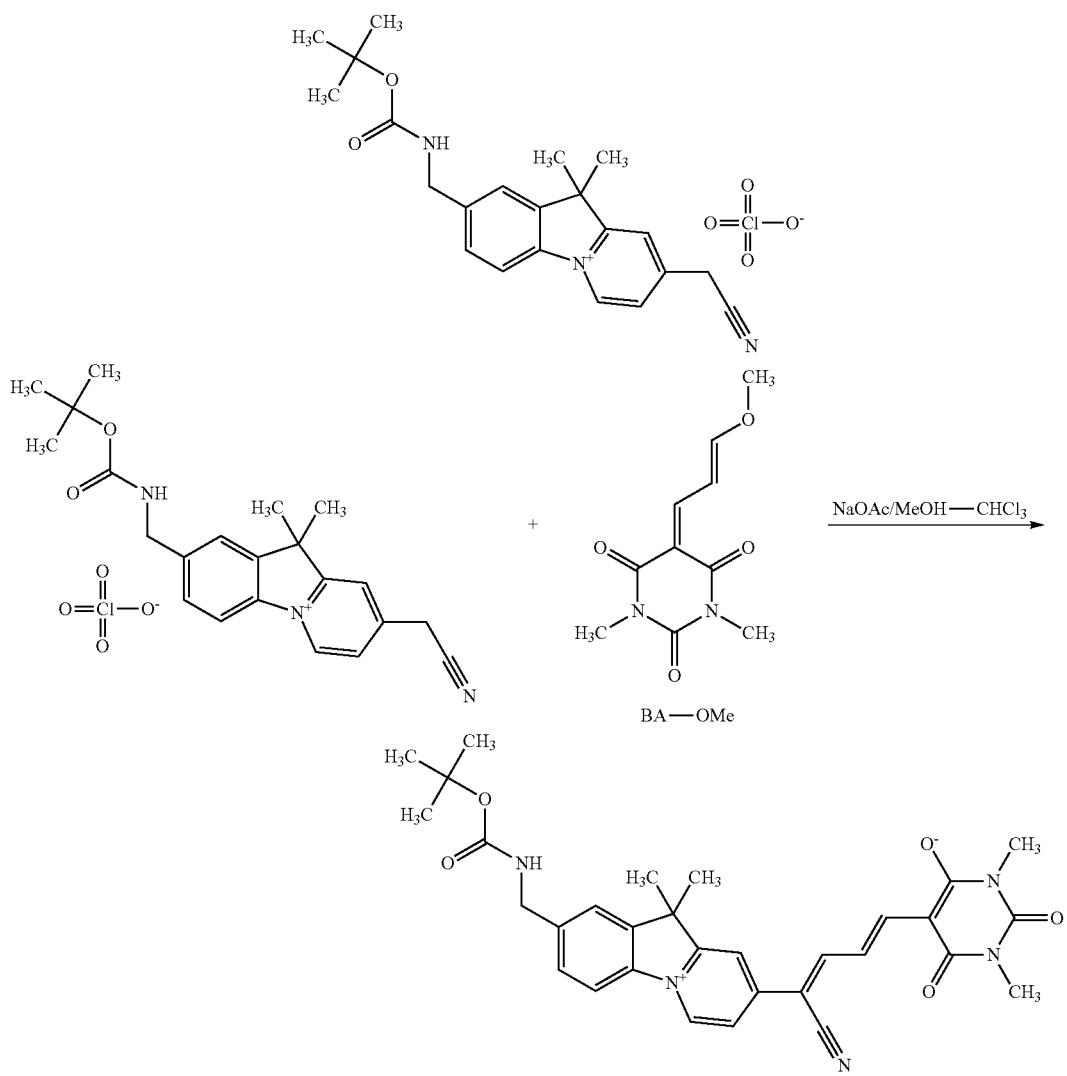
Intermediate 6

1.0 g of intermediate 5 was added to the solution of 1.0 g of Hydroxylamine-O-sulfonic acid in 25 mL of MeOH:H₂O mixture (1:1) and the resulting suspension was stirred at room temperature for 24 hours. The solid was filtered off and the volume of the solution was reduced in about a half on Rotovapor. The dark residue deposited on the wall, the solution was discarded and the residue was washed with water (2×20 mL). The residue was dissolved in 25 mL of MeOH—CHCl₃ (1:1) mixture, 600 mg of BA-OMe was added followed by 200 mg of NaOAc. The mixture was stirred under reflux for 30 min, during this time mixture become a very deep-blue colored. The solution was cooled and the solvents were evaporated. The dye was purified by silica gel chromatography using acetone as eluent.

5.7 Synthesis of Intermediate 7

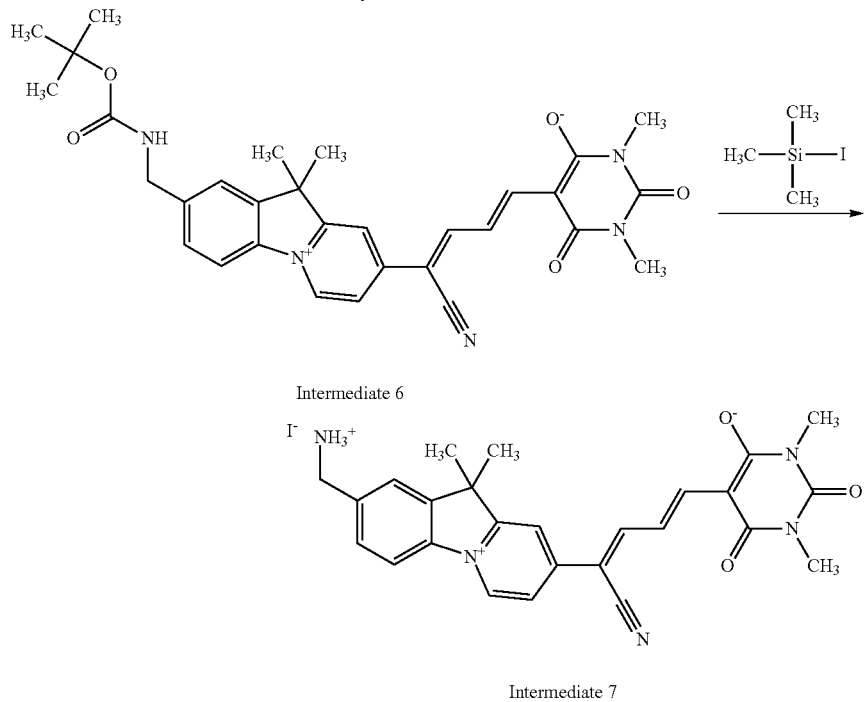

600 mg of the intermediate 6 were dissolved in 20 mL of acetonitrile. 0.5 mL of trimethylsilyl iodide was added to the solution and the mixture was stirred under nitrogen for 1 hour. Immediately after addition of trimethylsilyl iodide (TMSI) the color of the mixture rapidly changed from deep blue to orange. 5 mL of methanol were added to destroy excess of TMSI and the complex of TMSI with the dye. The solution became blue again. The solution was reduced in volume to about 10 mL in vacuum. The intermediate 7 precipitated (it is not soluble in acetonitrile). The dye was filtered, washed with acetonitrile (2×10 mL) and dried. The yield was 580 mg (92%).

NMR (300 MHz DMSO-d₆): 1.65 (s, 6H, 2*CH₃), 3.15 (s, 3H, CH₃), 3.18 (s, 3H, CH₃), 4.15 (q, 2H, $^3J_{H-H}$=5.4 Hz, CH₂N), 7.55 (bs, 1H), 7.63 (dd, 1H, $^3J_{H-H}$=8.4 and 1.2 Hz), 7.76 (t, 1H, $^3J_{H-H}$=13.2 Hz), 7.80 (d, 1H, $^3J_{H-H}$=1.5 Hz), 8.1 (bs, 4H), 8.42 (d, 1H, $^3J_{H-H}$=12.9 Hz), 9.04 (d, 1H, $^3J_{H-H}$=7.2 Hz).

5.8 Synthesis of Intermediate 8

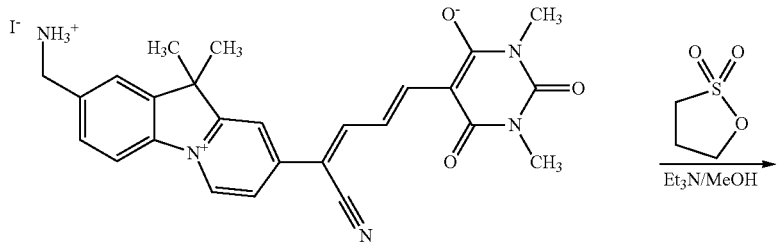

Intermediate 7

-continued

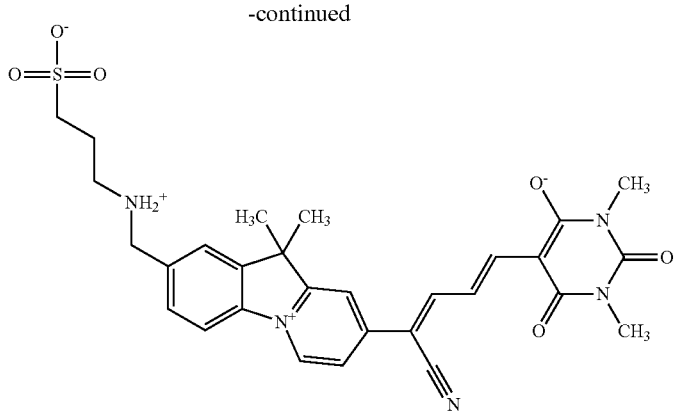

Intermediate 8

500 mg (0.86 mmol) of intermediate 7 were dissolved in 10 mL of anhydrous methanol, 87 mg (0.86 mmol) of triethylamine were added to the solution followed by 104 mg (0.86 mmol) of propane sulfone. The mixture was stirred under reflux for 24 hours. During 10-h time intervals an aliquot was taken from the mixture and analyzed by HPLC. The HPLC conditions are as follows:

TABLE 6

HPLC Conditions for Analysis of Reaction Product for Intermediate 8

1) column - C18 Vydac Cat. # 218TP54
2) Eluent: gradient acetonitrile in water, 1.0 mL/min.
Solution A - 10% acetonitrile, 90% water, 0.1% TFA
Solution B - 90% acetonitrile, 10% water, 0.1 TFA
Gradient:

0 min - 100% A, 0% B
31 min - 40% A, 60% B

TABLE 6-continued

HPLC Conditions for Analysis of Reaction Product for Intermediate 8

35 min - 0% A, 100% B
36 min - 100% A, 0% B.

An example of representative HPLC traces are shown in FIGS. 7A and 7B, in which the peak with peak with tR of approximately 24.6-24.9 minutes is intermediate 7 and the peak with tR of approximately 23.7 minutes is intermediate 8. When a conversion of about 60% to about 70% was achieved the reaction was stopped. The crude product was used in the next step. The pure dye can be isolated by HPLC.

NMR (300 MHz DMSO-$d_6$): 1.66 (s, 6H, 2*$CH_3$), 2.09 (p, 2H, $^3J_{H-H}$=6.8 Hz, $CH_2CH_2CH_2$), 2.78 (p, 2H, $^3J_{H-H}$=6.8 Hz, $CH_2SO_3$), 3.16 (s, 3H, $CH_3$), 3.18 (s, 3H, $CH_3$), 4.15 (q, 2H, $^3J_{H-H}$=5.4 Hz, $CH_2N$), 4.25 (t, 2H, $^3J_{H-H}$=6.6 Hz, $CH_2N$), 7.55 (bs, 1H), 7.63 (m, 1H), 7.76 (t, 1H, $^3J_{H-H}$=13.2 Hz), 7.80 (m, 1H, $^3J_{H-H}$=1.5 Hz), 8.06 (d, 1H, $^3J_{H-H}$=13.2 Hz), 8.13 (m, 1H), 8.22 (bs, 1H), 8.42 (d, 1H, $^3J_{H-H}$=12.9 Hz), 9.04 (m, 1H), 9.2 (bs, 1-2H, $NH_2^+$).

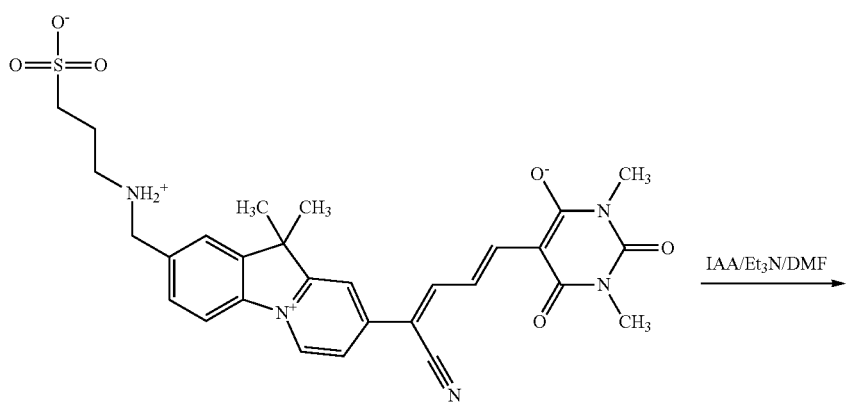

Intermediate 8

IAA/Et$_3$N/DMF →

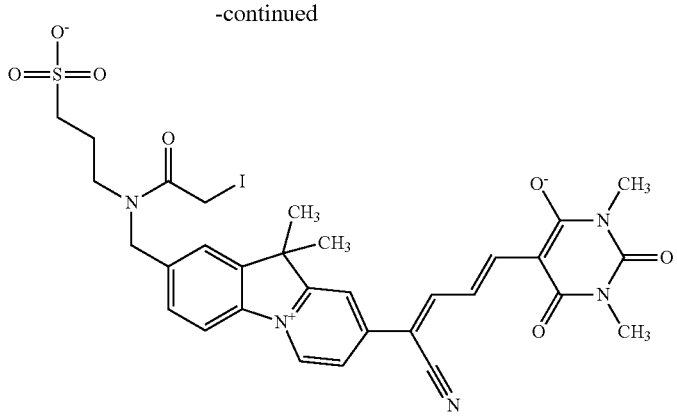

500 mg of the crude intermediate 8 were dissolved in 10 mL of DMF, 0.5 mL of triethylamine was added to the solution, followed by 0.5 g of iodoacetic anhydride. The mixture was stirred at room temperature for 2 hours. The solvent was evaporated and the residue was purified on preparative HPLC.

TABLE 7

Analytical HPLC Conditions 1) column - C18 Vydac Cat. # 218TP54
2) Eluent: gradient acetonitrile in water, 1.0 mL/min.
Solution A - 10% acetonitrile, 90% water, 0.1% TFA
Solution B - 90% acetonitrile, 10% water, 0.1 TFA
Gradient:

0 min - 100% A, 0% B
31 min - 40% A, 60% B
35 min - 0% A, 100% B
36 min - 100% A, 0% B.

A representative HPLC trace is shown in FIG. 8, wherein the compound with tR=23.352 is unreacted intermediate 8, the compound with tR=27.6 is the final dye product and the compound with tR=31.4 is a byproduct.

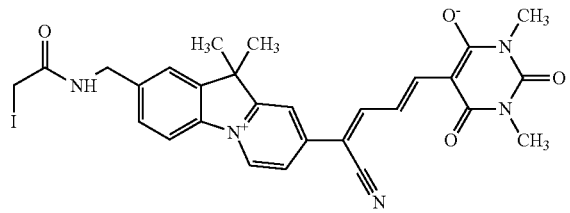 [SMILES: Cn1c([O-])c(/C=C/C=C(\C#N)c2cc[n+]3c(c2)C(C)(C)c2cc(CNC(=O)CI)ccc2-3)c(=O)n(C)c1=O]

TABLE 8

Preparative HPLC Conditions.

1) column - C18 Vydac Cat. # 218TP152022
2) Eluent: gradient acetonitrile in water, 3.0 mL/min.
Solution A - 10% acetonitrile, 90% water, 0.1% TFA
Solution B - 90% acetonitrile, 10% water, 0.1 TFA
Gradient:

0 min - 100% A, 0% B
40 min - 70% A, 30% B
80 min - 40% A, 60% B
120 min - 0% A, 100% B TABLE 8-continued Preparative HPLC Conditions.

140 min - 0% A 100% B
150 min - 100% A, 0% B

Example 6

Synthesis of N-ethyl-N-isopropylpropan-2-aminium 3-(N-((8-((1Z,3E)-1-cyano-4-(1,3-dimethyl-6-oxido-2,4-dioxo-1,2,3,4-tetrahydropyrimidin-5-yl)buta-1,3-dienyl)-10,10-dimethyl-10H-pyrido[1,2-a]indolium-2-yl)methyl)-2-iodoacetamido)propane-1-sulfonate

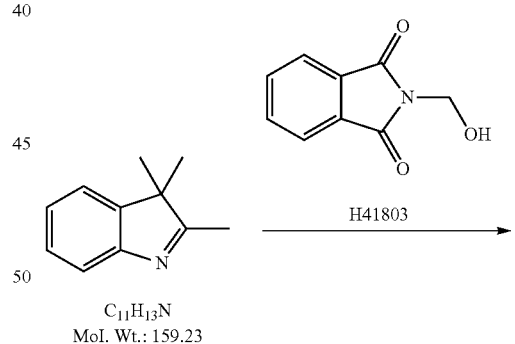

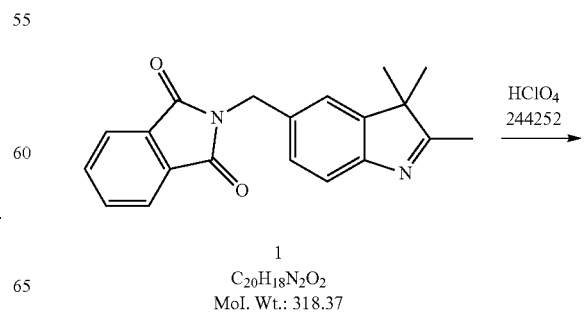

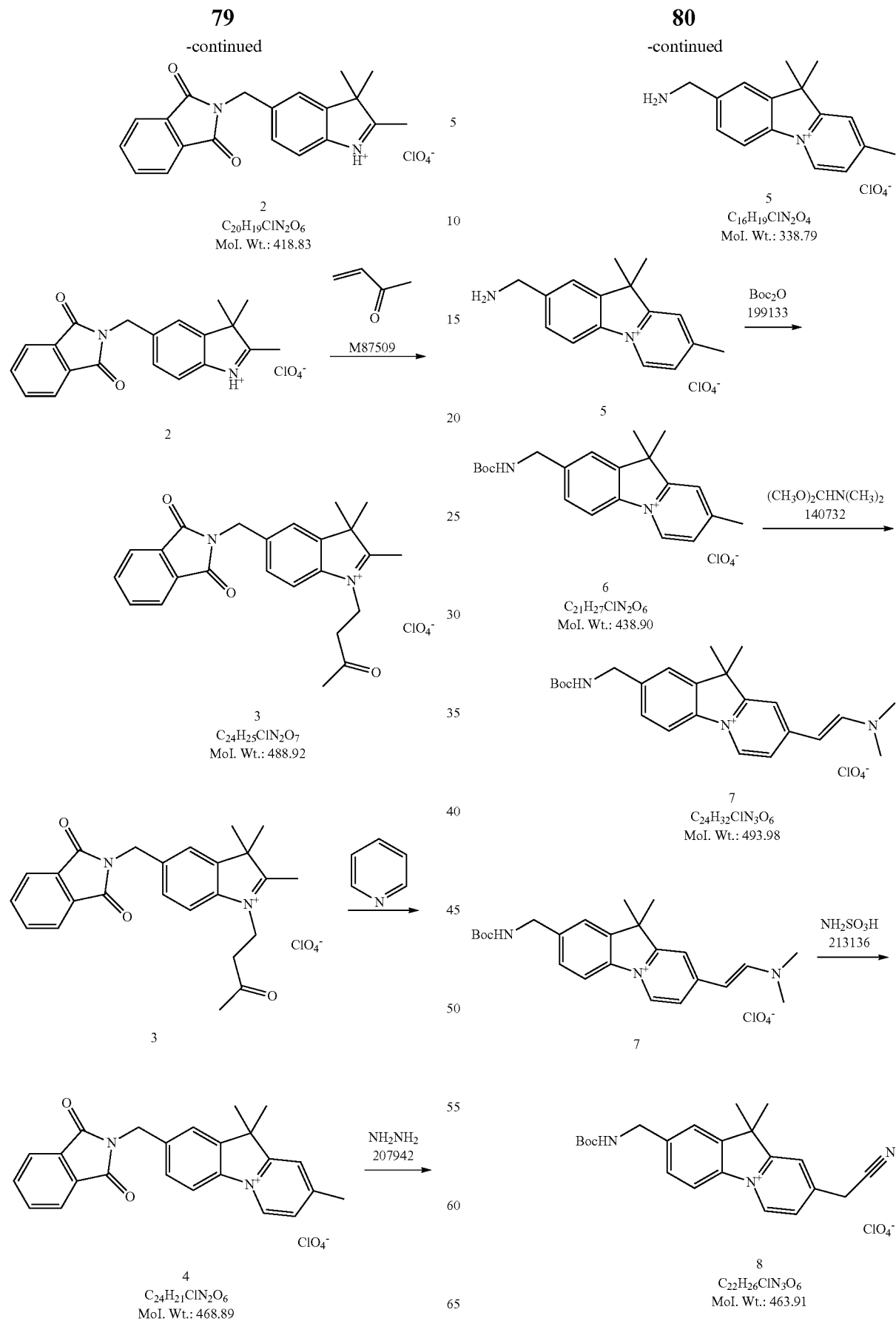

Scheme 10. Synthesis of N-ethyl-N-isopropylpropan-2-aminium 3-(N-((8-((1Z,3E)-1-cyano-4-(1,3-dimethyl-6-oxido-2,4-dioxo-1,2,3,4-tetrahydropyrimidin-5-yl)buta-1,3-dienyl)-10,10-dimethyl-10H-pyrido[1,2-a]indolium-2-yl)methyl)-2-iodoacetamido)propane-1-sulfonate
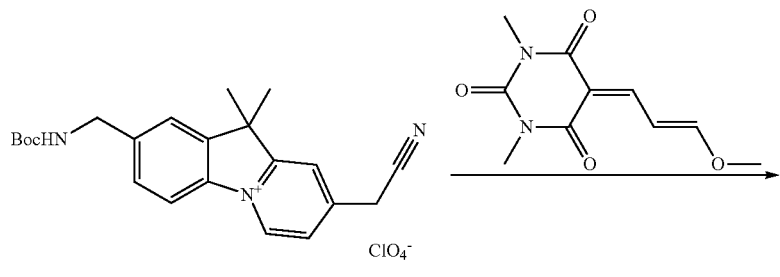
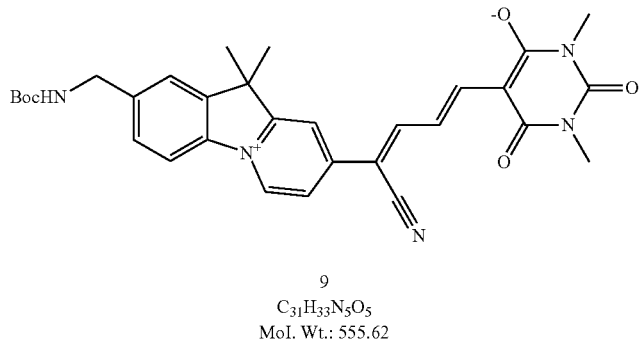
9
$C_{31}H_{33}N_5O_5$
Mol. Wt.: 555.62
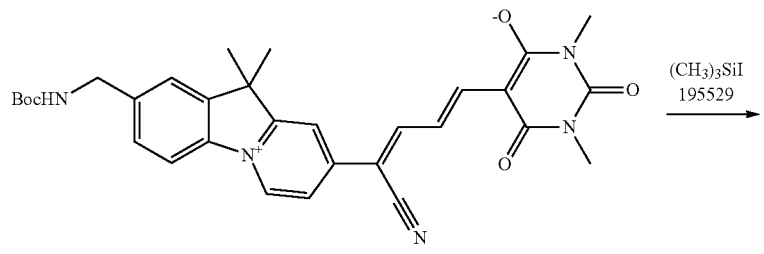
9
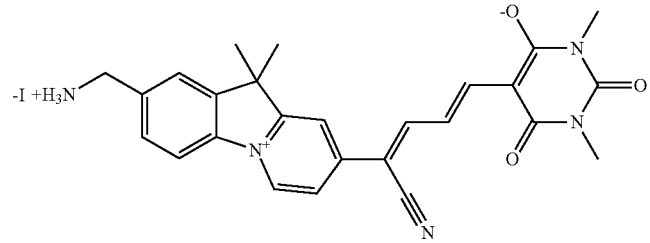
10
$C_{26}H_{26}IN_5O_3$
Mol. Wt.: 583.42

-continued
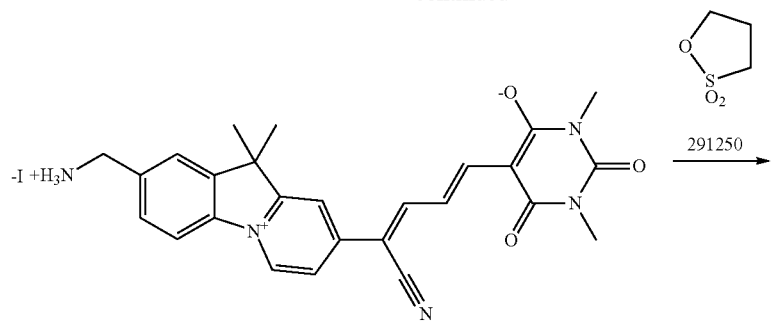
10
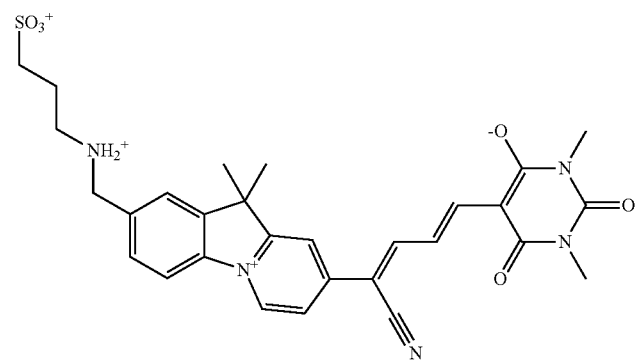
11
C29H31IN5O6S
Mol. Wt.: 577.65
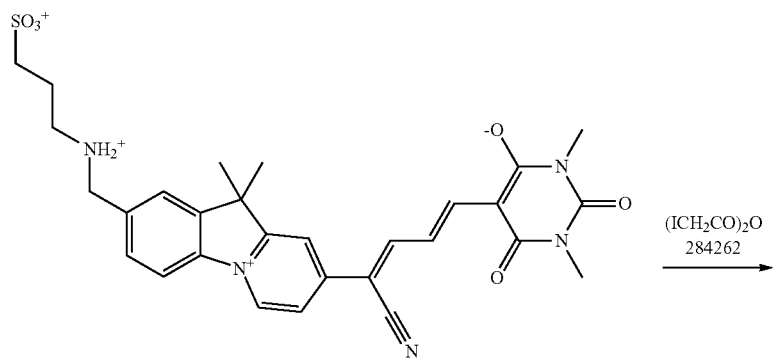
11
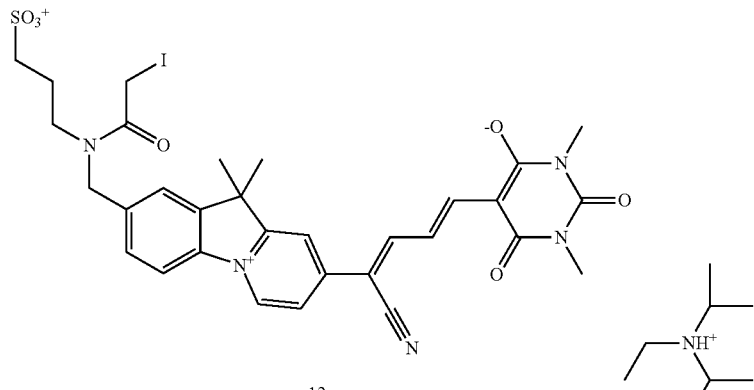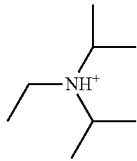
12
C39H51IN6O7S
Mol. Wt.: 874.83

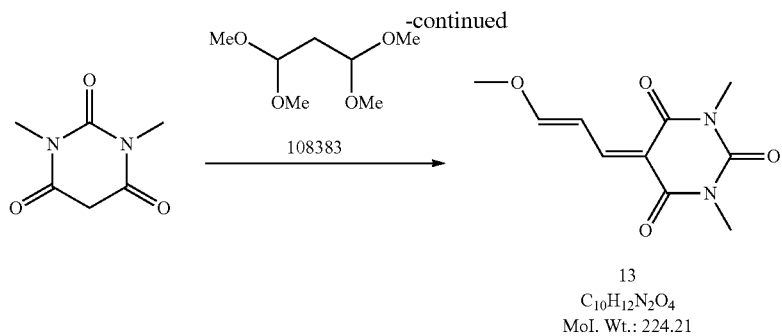

13
$C_{10}H_{12}N_2O_4$
Mol. Wt.: 224.21

Scheme 10 (con't). Synthesis of N-ethyl-N-isopropylpropan-2-aminium 3-(N-((8-((1Z,3E)-1-cyano-4-(1,3-dimethyl-6-oxido-2,4-dioxo-1,2,3,4-tetrahydropyrimidin-5-yl)buta-1,3-dienyl)-10,10-dimethyl-10H-pyrido[1,2-a]indolium-2-yl)methyl)-2-iodoacetamido)propane-1-sulfonate

6.1 2-(2,3,3-Trimethyl-3H-indol-5-ylmethyl)-isoindole-1,3-dione, 1

Sulfuric acid (420.0 mL, 7.879 mol; Sigma-Aldrich) was placed to the 1 L one-neck, round-bottom flask equipped with magnetic stirrer. The flask was cooled in ice-water bath and 2,3,3-trimethyl-3H-Indole, (100.0 g, 0.6280 mol; Sigma-Aldrich) was added to the sulfuric acid by drops during 45 min with stirring. The reaction mixture becomes a very viscous upon addition of 2,3,3-trimethyl-3H-indole, so stirring plate with adequate power and large magnetic stir bar is required. When addition of 2,3,3-trimethyl-3H-Indole was completed the ice bath was removed and 2-(hydroxymethyl)-1H-Isoindole-1,3(2H)-dione, (112 g, 0.632 mol; Aldrich) was added to the reaction mixture at once. The flask was closed with a glass stopper and the stirring was continued for 168 hours at room temperature. In about 12 hours all solid, 2-(hydroxymethyl)-1H-Isoindole-1,3(2H)-dione dissolved and clear brown solution formed.

After 168 hours the content of the flask was poured into 4-L conical flask containing 1 kg of ice. The 4-L flask was immersed in ice-salt bath, equipped with mechanical stirrer. A cooled to 10° C. solution of 550 g of NaOH in 1.5 L of water was slowly added to the reaction mixture at such rate that temperature inside of flask didn't increase higher than 20° C. The addition takes about 1 hour. The white precipitate formed was filtered on Buchner funnel with suction and dried on air for 12 hours.

The crude 2-(2,3,3-Trimethyl-3H-indol-5-ylmethyl)-isoindole-1,3-dione was placed in conical 2 L flask, 1 L of acetone was added and the mixture was magnetically stirred with heating until acetone start to boil. The heating was reduced to maintain a very gentle boiling and the content of the flask was stirred for additional 10 min. Flask was cooled using ice-water bath and the separated crystals were filtered, washed with acetone and dried.

The yield of the first crop with m.p.=186-187° C. was 82 g. The mother liquor was reduced in volume to about 300 mL and cooled at −10° C. overnight. The separated crystals were filtered, washed with acetone and dried. The yield of the second crop with m.p.=184-185° C. was 45 g. The total yield was 126 g (63% of theoretical).

Analytical Results for 1:
M.p.=186-187° C.
$^1$H NMR (CDCl$_3$, 300 MHz) δ 1.28 (s, 6H), 2.25 (s, 3H), 4.87 (s, 2H), 7.38-7.45 (m, 3H), 7.68-7.71 (m, 2H), 7.83-7.86 (m, 2H).
$^{13}$C NMR (CDCl$_3$, 75 MHz) δ 15.4, 23.0, 41.7, 53.7, 119.8, 122.0, 123.3, 128.4, 132.2, 133.3, 133.9, 146.1, 153.5, 168.0, 188.5.

6.2 5-(1,3-Dioxo-1,3-dihydro-isoindol-2-ylmethyl)-2,3,3-trimethyl-3H-indolium perchlorate, 2

2-(2,3,3-Trimethyl-3H-indol-5-ylmethyl)-isoindole-1,3-dione (126 g, 0.396 mol; Sigma-Aldrich) was placed in 1 L one-necked flask equipped with magnetic stir bar and a reflux condenser. 500 mL Ethanol (500 mL, 8 mol; Pharmco) were added to the flask followed by addition of perchloric acid (35 mL, 0.40 mol; Aldrich). The reaction mixture was stirred with heating under reflux until all solids dissolved. The solution was then cooled at −10° C. for 3 hours and the separated crystals were filtered, washed with cold ethanol (100 mL), diethyl ether (2*100 mL) and dried. The yield was 166 g (100% of theoretical).

Analytical Results for 2:
M.p.>250° C.
$^1$H NMR (DMSO-d$_6$, 300 MHz) δ 1.46 (s, 6H), 2.64 (s, 3H), 4.87 (s, 2H), 7.43 (d, $^3J_{H-H}$=8.0 Hz, 1H), 7.58 (d, $^3J_{H-H}$=8.1 Hz, 1H), 7.71 (s, 1H), 7.86-7.90 (m, 4H).
$^{13}$C NMR (DMSO-d$_6$, 75 MHz) δ 14.8, 21.9, 40.7, 53.8, 116.7, 122.0, 123.2, 127.5, 131.5, 134.5, 136.8, 143.7, 167.6, 196.1.

6.3 5-(1,3-Dioxo-1,3-dihydro-isoindol-2-ylmethyl)-2,3,3-trimethyl-1-(3-oxo-butyl)-3H-indolium perchlorate, 3

5-(1,3-Dioxo-1,3-dihydro-isoindol-2-ylmethyl)-1,2,3,3-tetramethyl-3H-indolium; perchlorate (166 g, 0.384 mol; Sigma-Aldrich) was placed in 1 L one-necked round-bottom flask equipped with magnetic stir bar and reflux condenser. Methyl vinyl ketone (200 mL, 2 mol; Aldrich) was added to flask and the flask was heated with stirring using an oil bath at 100° C. In about 3 minutes after the heating the reaction mixture started to boil. The oil bath was removed and mixture was stirred for 5 minutes without heating until boiling stopped. Flask was again heated with stirring using an oil bath at 100° C. for additional 15 minutes. After the heating was stopped, the flask was cooled to room temperature and unreacted methyl vinyl ketone was removed in vacuum. 300 mL of acetone was added to the semi-solid dark-brown residue and flask was heated with stirring until residue dissolved. The flask was then cooled to −10° C. for 3 hours. The crystallized product was separated by filtration, washed cold acetone (2*100 mL), ether (2*100 mL) and dried. The yield was 112 g (59.7% of theory).
Analytical Results for 3:
M.p.=85-90° C. (dec.)
$^1$H NMR (DMSO-d$_6$, 300 MHz) δ 1.50 (s, 6H), 2.12 (s, 3H), 2.83 (s, 3H), 3.20 (t, $^3J_{H-H}$=6.6 Hz, 2H), 4.55 (t, $^3J_{H-H}$=6.6 Hz, 2H), 4.90 (s, 2H), 7.56 (d, $^3J_{H-H}$=6.6 Hz, 1H), 7.80 (s, 1H), 7.87-7.94 (m, 5H).
$^{13}$C NMR (DMSO-d$_6$, 75 MHz) δ 14.0, 21.7, 29.6, 42.6, 54.1, 115.5, 122.1, 123.1, 127.7, 131.5, 134.4, 138.3, 140.1, 142.1, 167.6, 197.3.

6.4 2-(1,3-Dioxo-1,3-dihydro-isoindol-2-ylmethyl)-8,10,10-trimethyl-10H-pyrido[1,2-a]indolylium, 4

5-(1,3-Dioxo-1,3-dihydro-isoindol-2-ylmethyl)-2,3,3-trimethyl-1-(3-oxo-butyl)-3H-indolium perchlorate (112 g, 0.229 mol; Sigma-Aldrich) and pyridine (260 mL, 3.2 mol) were placed into 1-L round bottom one-necked flask equipped with magnetic stir bar and reflux condenser. The reaction mixture was refluxed with stirring for one hour. The reaction mixture was cooled to room temperature and pyridine was removed under vacuum. The semi-solid red residue was treated with boiling toluene (200 mL) with stirring for 30 min. The flask was cooled and the toluene layer was decanted from solid residue. 200 mL of ethanol was added to the residue and the mixture was stirred under reflux for 20 min. The solid was filtered from hot solution and treated again with 200 mL of boiling ethanol with stirring for 10 min. The solid was filtered from hot solution and treated again with boiling ethanol (200 mL) for 10 min. The solid was filtered, washed with hot ethanol and dried. The yield was 26 g. The combined ethanol solution was evaporated and the residue was treated in the same way with boiling ethanol (3 times, 100 mL). The second crop was 9 g. The total yield was 35 g (white solid, 32% of theory).
Analytical Results for 4:
M.p.>250° C.
$^1$H NMR (DMSO-d$_6$, 300 MHz) δ 1.67 (s, 6H), 2.71 (s, 3H), 4.93 (s, 2H), 7.64 (d, $^3J_{H-H}$=8.4 Hz, 1H), 7.87-7.94 (m, 5H), 8.08 (d, $^3J_{H-H}$=6.4 Hz, 1H), 8.31 (d, $^3J_{H-H}$=8.1 Hz, 1H), 8.43 (s, 1H), 9.66 (d, $^3J_{H-H}$=6.5 Hz, 1H).

6.5 2-Aminomethyl-8,10,10-trimethyl-10H-pyrido[1,2-a]indolylium perchlorate, 5

2-(1,3-Dioxo-1,3-dihydro-isoindol-2-ylmethyl)-8,10,10-trimethyl-10H-pyrido[1,2-a]indolylium perchlorate (36 g, 0.077 mol; Sigma-Aldrich) was added to a conical 1-L flask equipped with magnetic stir bar, followed by 480 mL of CH$_2$Cl$_2$—CH$_3$OH mixture (3:2). Stirring was started and hydrazine monohydrate (25 g, 0.50 mol; Aldrich) was added to the reaction mixture at once. Stirring was continued until all solid was dissolved. The flask was closed with a stopper and let to stand at room temperature overnight without stirring. After about 16 hours the precipitated solid phthalhydrazide was filtered off, washed with 100 mL of CH$_2$Cl$_2$—CH$_3$OH mixture (3:2) and discarded. The combined filtrates were evaporated and the resulted solid was washed with Ether-CH$_3$OH. The solid was filtered, washed with ether and dried. The yield was 26 g (100% of theory).
Analytical Results for 5:
M.p.>250° C.
$^1$H NMR (DMSO-d$_6$, 300 MHz) δ 1.67 (s, 6H), 2.07 (bs, 2H), 2.70 (s, 3H), 3.87 (s, 2H), 4.87 (s, 2H), 7.65 (d, $^3J_{H-H}$=8.1 Hz, 1H), 7.85 (s, 1H), 8.08 (d, $^3J_{H-H}$=6.3 Hz, 1H), 8.27 (d, $^3J_{H-H}$=8.4 Hz, 1H), 8.44 (s, 1H), 9.65 (d, $^3J_{H-H}$=6.3 Hz, 1H).
$^{13}$C NMR (DMSO-d$_6$, 75 MHz) δ 21.8, 25.0, 45.2, 47.1, 114.2, 122.4, 123.5, 126.5, 127.7, 134.3, 137.0, 141.3, 147.7, 158.6, 162.4.

6.6 2-(tert-Butoxycarbonylamino-methyl)-8,10,10-trimethyl-10H-pyrido[1,2-a]indolylium perchlorate, 6

2-Aminomethyl-8,10,10-trimethyl-10H-pyrido[1,2-a]indolylium; perchlorate (26.0 g, 0.077 mol) was placed in 1 L round bottom, one-necked flask equipped with magnetic stir bar. 480 mL of 3:1 mixture of CH$_2$Cl$_2$—CH$_3$CN was added to the flask followed by 12.0 g of triethylamine and 27.0 g of tert-butyl pyrocarbonate. The stirring was continued for 24 hours at room temperature. The solvent was removed in vacuum and the crude product (viscous oil) was used in the next step without additional purification. Yield 34 g (100%).
Analytical Results for 6:
$^1$H NMR (DMSO-d$_6$, 300 MHz) δ 1.38-1.43 (m, 15H), 2.71 (s, 3H), 4.28 (d, $^3J_{H-H}$=6.0 Hz, 2H), 7.54 (d, $^3J_{H-H}$=8.4 Hz, 1H), 7.71 (s, 1H), 8.07 (d, $^3J_{H-H}$=6.3 Hz, 1H), 8.29 (d, $^3J_{H-H}$=8.4 Hz, 1H), 8.43 (s, 1H), 9.63 (d, $^3J_{H-H}$=6.3 Hz, 1H).

6.7 2-(tert-Butoxycarbonylamino-methyl)-8-(2-dimethylamino-vinyl)-10,10-dimethyl-10H-pyrido[1,2-a]indolylium perchlorate, 7

2-(tert-Butoxycarbonylamino-methyl)-8,10,10-trimethyl-10H-pyrido[1,2-a]indolylium perchlorate (34 g, 0.077 mol; Sigma-Aldrich) was placed in 1-L round-bottom, one-necked flask equipped with magnetic stir bar and a reflux condenser. 75 mL of dimethylformamide and 38.5 mL of 1,1-Dimethoxy-N,N-dimethylmethanamine (38.5 mL, 0.290 mol; Aldrich) were added to the flask followed by 1,8-Diazabicyclo[5.4.0]undec-7-ene (0.1 g, 0.0006 mol; Aldrich). The flask was immersed in oil bath with temperature set to 100° C. Stirring was started and continued for 30 min. The flask was cooled to room temperature, the solvent was evaporated in vacuum and the residue was recrystallized from methanol. The yield was 29 g (green crystals, 71% of theory).
Analytical Results for 7:
M.p.=247-252° C. (dec.)
$^1$H NMR (DMSO-d$_6$, 300 MHz) δ 1.41 (s, 9H), 1.58 (s, 6H), 2.99 (s, 3H), 3.26 (s, 3H), 4.21 (d, $^3J_{H-H}$=6.0 Hz, 2H), 5.46 (d, $^3J_{H-H}$=12.9 Hz, 1H), 7.39 (d, $^3J_{H-H}$=8.4 Hz, 1H), 7.4 (bs, 2H), 7.45 (t, $^3J_{H-H}$=6.0 Hz, 1H), 7.55 (s, 1H), 7.93 (d, $^3J_{H-H}$=8.4 Hz, 1H), 8.20 (d, $^3J_{H-H}$=12.9 Hz, 1H), 8.82 (d, $^3J_{H-H}$=7.2 Hz, 1H).
$^{13}$C NMR (DMSO-d$_6$, 75 MHz) δ 26.2, 28.1, 45.8, 48.5, 77.9, 93.8, 112.1, 122.1, 127.1, 131.4, 137.4, 140.0, 140.5, 153.0, 155.5, 155.7, 159.9.

6.8 2-(tert-Butoxycarbonylamino-methyl)-8-cyanomethyl-10,10-dimethyl-10H-pyrido[1,2-a]indolylium perchlorate, 8

2-(tert-Butoxycarbonylamino-methyl)-8-(2-dimethylamino-vinyl)-10,10-dimethyl-10H-pyrido[1,2-a]indolylium perchlorate (14 g, 0.028 mol; Sigma-Aldrich) was placed into 500-mL conical flask equipped with magnetic stir bar followed by 400 mL of 1:1 MeOH—H2O mixture. Stirring was started and hydroxylamine-O-sulfonic acid (14 g, 0.12 mol; Aldrich) was added to the flask in one portion. In about 2 hours all solid was dissolved and stirring was continued for additional 48 hours at room temperature. Sodium bicarbonate (2.00 g) was added to the reaction mixture to adjust pH equal to 7.0. The reaction mixture was transferred into 1-L round bottom one-necked flask and 80% of the reaction solvent was evaporated under vacuum. The product deposited on flask wall as a slightly yellow tar. The aqueous solution (ca 80-100 mL) that contained excess of hydroxylamino sulfonic acid was discarded and the deposited tar was washed with water (2*60 mL) and dissolved in 250 mL water-methanol (1:1) mixture. Most of the solvent was again removed in vacuum, aqueous solution (approximately 50 mL) discarded, the separated organic residue was washed with water (2*60 mL), ether and dried. The crude product was used in the next step without additional purification. The yield of crude material was 13.1 g (100% of theory).

Analytical Results for 8:

$^1$H NMR (DMSO-d$_6$, 300 MHz) δ 1.41 (s, 9H), 1.70 (s, 6H), 4.25 (d, $^3J_{H\text{-}H}$=5.4 Hz, 2H), 4.58 (s, 2H), 7.55-7.58 (m, 2H), 7.73 (s, 1H), 8.19 (d, $^3J_{H\text{-}H}$=6.3 Hz, 1H), 8.33 (d, $^3J_{H\text{-}H}$=8.4 Hz, 1H), 8.55 (s, 1H), 9.77 (d, $^3J_{H\text{-}H}$=6.6 Hz, 1H).

$^{13}$C NMR (DMSO-d$_6$, 75 MHz) δ 23.4, 24.8, 28.1, 43.28, 47.6, 78.1, 115.0, 122.3, 122.7, 125.6, 127.6, 135.8, 141.9, 150.5, 155.8, 163.4.

6.9 {8-[1-Cyano-4-(1,3-dimethyl-2,4,6-trioxo-tetrahydro-pyrimidin-5-ylidene)-but-2-enylidene]-10,10-dimethyl-8,10-dihydro-pyrido[1,2-a]indol-2-ylmethyl}-carbamic acid tert-butyl ester, 9

2-(tert-Butoxycarbonylamino-methyl)-10,10-dimethyl-8-prop-2-ynyl-10H-pyrido[1,2-a]indolylium (13.1 g, 0.0360 mol; Sigma-Aldrich) was placed in 1-L round bottom, one-necked flask equipped with magnetic stir bar and a reflux condenser. 300 mL of CH$_2$Cl$_2$-MeOH mixture (1:1) was added to the flask followed by 5-(3-Methoxy-allylidene)-1,3-dimethyl-pyrimidine-2,4,6-trione (10 g, 0.04 mol; Sigma-Aldrich). The stirring was started and the flask was heated until a gentle reflux began and then a solution of sodium acetate (6 g, 0.07 mol; Aldrich) in 60 mL of methanol were added to the flask through the top of the reflux condenser. The flask was heated with stirring under reflux for additional 1 hour. The reaction mixture becomes deep blue during this time. TLC showed formation of a blue dye with Rf about 0.5, silica gel, eluent acetone as a major product. The flask was cooled to room temperature, the solvent was evaporated and the crude residue was used in the next step without additional purification.

6.10 8-[1-Cyano-4-(1,3-dimethyl-2,4,6-trioxo-tetrahydro-pyrimidin-5-ylidene)-but-2-enylidene]-10,10-dimethyl-8,10-dihydro-pyrido[1,2-a]indol-2-ylmethyl-ammonium iodide, 10

{8-[1-Cyano-4-(1,3-dimethyl-2,4,6-trioxo-tetrahydro-pyrimidin-5-ylidene)-but-2-enylidene]-10,10-dimethyl-8,10-dihydro-pyrido[1,2-a]indol-2-ylmethyl}-carbamic acid tert-butyl ester (20 g, 0.04 mol; Sigma-Aldrich) from previous step was placed in one-necked round bottom 1 L flask equipped with magnetic stir bar and dissolved in 150 mL of acetonitrile. The flask was closed with rubber septa and flashed with dry nitrogen. 10 g of iodotrimethylsilane were added to the flask with use of syringe, and reaction mixture was stirred at room temperature for 30 min. During addition of iodotrimethylsilane the color of the flask changed from deep blue to deep orange. 25 mL of methanol were added to the reaction mixture and its color become deep blue again. The volume of reaction mixture was reduced in about half using rotary evaporator. During this operation most of the methanol was removed from the reaction mixture and the product, which is insoluble in acetonitrile, precipitates. The product was filtered, washed with acetonitrile, dried and transferred to a 500-mL conical flask equipped with magnetic stirrer. 200 mL of dichloromethane were added to the flask, and flask content was stirred with mild heating (very gentle DCM boiling) for 10 min. The mixture was filtered when still hot, the dye was washed with DCM and dried. The yield was 10 g (50% of theory based on two steps).

Analytical Results for 10:

M.p.>250° C.

$^1$H NMR (DMSO-d$_6$, 300 MHz) δ 1.65 (s, 6H), 3.15 (s, 3H), 3.18 (s, 3H), 4.15 (d, $^3J_{H\text{-}H}$=5.4 Hz, 1H), 7.5 (bs, 1H), 7.63 (dd, $^3J_{H\text{-}H}$=8.0 Hz, $^4J_{H\text{-}H}$=1.2 Hz, 1H), 7.76 (t, $^3J_{H\text{-}H}$=13.2 Hz, 1H), 7.80 (d, $^4J_{H\text{-}H}$=1.2 Hz, 1H), 8.0-8.2 (bs, 1H), 8.05 (d, $^3J_{H\text{-}H}$=13.2 Hz, 1H), 8.10 (d, $^3J_{H\text{-}H}$=8.7 Hz, 1H), 8.2 (bs, 3H), 8.42 (d, $^3J_{H\text{-}H}$=12.9 Hz, 1H), 9.05 (d, $^3$=7.2 Hz, 1H).

6.11 3-((8-((1Z,3E)-1-cyano-4-(1,3-dimethyl-6-oxido-2,4-dioxo-1,2,3,4-tetrahydropyrimidin-5-yl)buta-1,3-dienyl)-10,10-dimethyl-10H-pyrido[1,2-a]indolium-2-yl)methylammonio)propane-1-sulfonate, 11

5-((1E,3Z)-4-(2-(ammoniomethyl)-10,10-dimethyl-10H-pyrido[1,2-a]indolium-8-yl)-4-cyanobuta-1,3-dienyl)-1,3-dimethyl-2,6-dioxo-1,2,3,6-tetrahydropyrimidin-4-olate (1.000 g, 0.001714 mol; Sigma-Aldrich) was placed in the 25 mL, round bottom, one-necked flask equipped with magnetic stir bar and a glass stopper. N-Methylpyrrolidinone (NMP, 20 mL, 0.2 mol; Aldrich) was added to the flask, followed by sodium acetate (0.281 g, 0.00343 mol; Aldrich). Stirring was started and 1,3-propane sultone (0.324 g, 0.00266 mol; Aldrich) was added to the flask as the solution in 5 mL of NMP. The flask was purged with nitrogen, closed with a stopper and stirring was continued for 48 hours. Analysis of the reaction mixture sample by HPLC revealed that conversion was 75% with the total yield of target compound 50%. The reaction was stopped and the reaction mixture was used in the next step without additional purification.

HPLC conditions: water-acetonitrile gradient. Start 15% acetonitrile in water. Ramp to 95% over 8 minutes. Hold 95% acetonitrile in water for 1 minute then return to 15% acetonitrile in water over 1 minute. Column is a Zorbax column eclipse xdb-c8 4.6×150 mm. Flow rate is 2 ml/minute. Detector is set at 249 nm. Retention time of the product was 2.83 min.

6.12 N-ethyl-N-isopropylpropan-2-aminium 3-(N-((8-((1Z,3E)-1-cyano-4-(1,3-dimethyl-6-oxido-2,4-dioxo-1,2,3,4-tetrahydropyrimidin-5-yl)buta-1,3-dienyl)-10,10-dimethyl-10H-pyrido[1,2-a]indolium-2-yl)methyl)-2-iodoacetamido)propane-1-sulfonate, 12

3-((8-((1Z,3E)-1-cyano-4-(1,3-dimethyl-6-oxido-2,4-dioxo-1,2,3,4-tetrahydropyrimidin-5-yl)buta-1,3-dienyl)-10,10-dimethyl-10H-pyrido[1,2-a]indolium-2-yl)methylammonio)propane-1-sulfonate (0.50 g, 0.00086 mol; Sigma-Aldrich) from previous step was placed in 100 mL round-bottom, one-necked flask equipped with magnetic stir bar. N-methylpyrrolidinone (10 mL) was added to the flask and the flask was closed with rubber septa and flushed with dry nitrogen. Flask was wrapped in alumina foil to protect dye from light. A solution of iodoacetic anhydride (0.7 g, 0.002 mol) in 5 mL of N-methylpyrrolidinone was added to the flask using a syringe, followed by the addition of a solution of N,N-Diisopropylethylamine (0.5 g, 0.004 mol; Aldrich) in 5 mL of N-methylpyrrolidinone. The reaction mixture was stirred at room temperature for 30 min and then 70 mL of diethyl ether were added to the flask to precipitate product. The purple solid was decanted from ether layer and treated with 50 mL of methanol-acetone mixture with stirring at room temperature for 1 hour. The acetone-methanol solution of the dye was filtered from insoluble impurities and mixed with 5 g of Silica gel. The solvent was removed in vacuum and the dye on silica was placed on the top of pre-made silica gel column. (Column was made from 100 g of Silica Gel in 300 mL of acetone. Size: diameter=1 inch, silica gel length=8 inch). The column was eluted with acetone-methanol mixtures. The product was eluted in 20% methanol. The combined solutions containing 12 were evaporated to about 10 mL. 100 mL of diethyl ether was added to precipitate the dye. The dye was filtered, dried and dissolved in 25 mL of $H_2O$-Acetonitrile mixture (4:1). The solution was filtered and then loaded on preparative C18 column, ModCol 50×250 mm. Program: flow rate 25 mL/min, 24 min pure water, 24 min 10% Acetonitrile, 10 min 15% Acetonitrile, 72 min 20% Acetonitrile, 50 min 80% Acetonitrile. The product started eluting at 80 min. The fractions were collected at 86-112 min. The dye solutions were evaporated to about 25 mL, frozen at −78° C. and then lyophilized for 72 hours. The yield was 230 mg (30% of theory based on two steps) of material with purity higher than 99% by HPLC analysis.

Analytical Results for 12:
M.p.=164-170° C. (dec.)

$^1$H NMR (DMSO-$d_6$, 300 MHz) δ 1.15-1.30 (m, 15H), 1.64-1.66 (m, 2H), 1.70-2.00 (m, 2H), 2.30-2.50 (m, 2H), 3.09-3.18 (m, 8H), 3.30-3.40 (m, 2H), 3.50-3.60 (m, 2H), 4.01 (s, 2H), 4.59 (s, 2H), 7.41 (d, $^3J_{H-H}$=8.4 Hz, 1H), 7.5 (bs, 1H), 7.58 (s, 1H), 7.78 (t, $^3J_{H-H}$=13.2 Hz, 1H), 8.0-8.4 (m, 4H), 8.44 (d, $^3J_{H-H}$=12.9 Hz, 1H), 9.08 (d, $^3J_{H-H}$=6.2 Hz, 1H).

MS-ESI (negative detection): 744.

6.13 5-(3-Methoxy-allylidene)-1,3-dimethyl-pyrimidine-2,4,6-trione, 13

1,3-Dimethylbarbituric acid (20 g, 0.1 mol; Aldrich) was placed in 100 mL round-bottom one-necked flask equipped with magnetic stir bar and reflux condenser, 1,1,3,3-tetramethoxy-propane, (40 mL, 0.2 mol; Aldrich) and 1 mL of Trifluoroacetic Acid (2 mL, 0.03 mol; Sigma) were added to the reaction mixture. The flask was heated at 100° C. with stirring for 5 hours and then cooled to room temperature. The crystallized product was filtered, washed with methanol and dried. The yield was 23 g (80% of theory).

Analytical Results for 13:
$^1$H NMR (CDCl$_3$, 300 MHz) δ 3.29-3.31 (m, 6H), 3.90 (s, 3H), 7.42-7.52 (m, 2H), 8.03 (d, $^3J_{H-H}$=11.7 Hz, 1H).

Example 7

Synthesis of Succinimidyl Esters of AI Dyes

A representative method for the synthesis of succinimidyl esters of AI dyes is provided in Scheme 11.

Scheme 11. Synthesis of Succinimidyl Esters of AI Dyes.

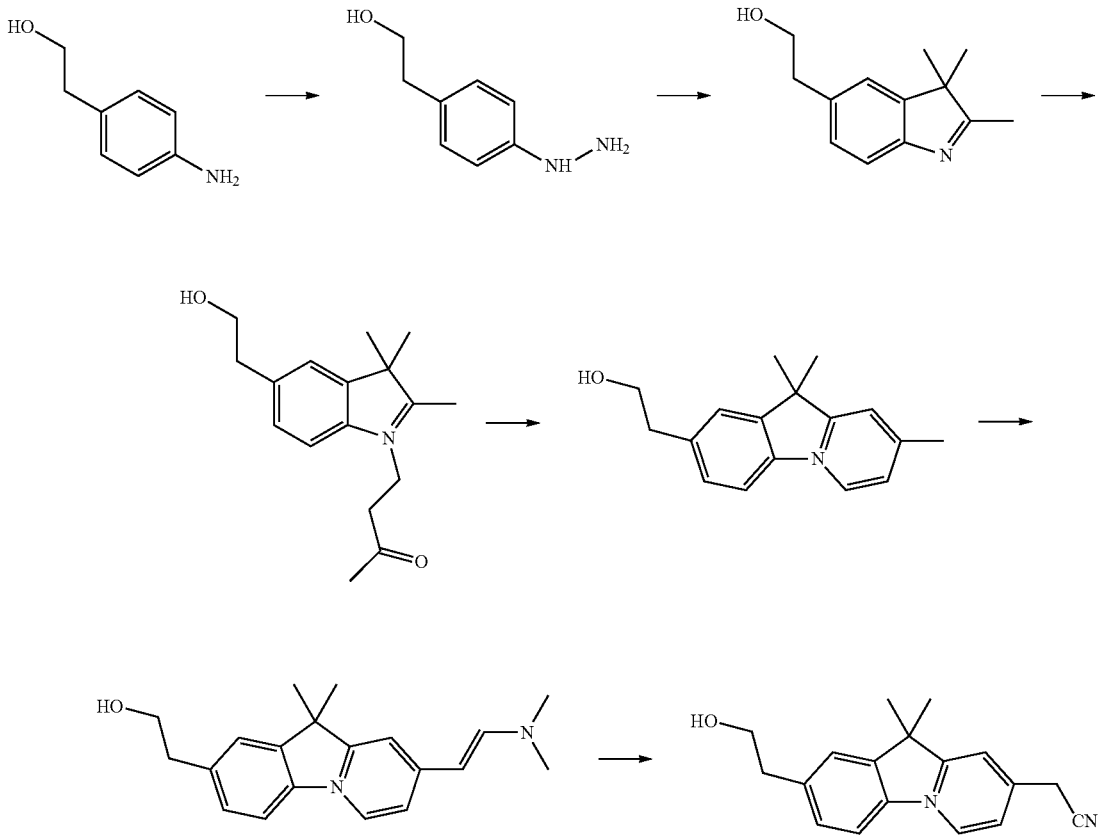

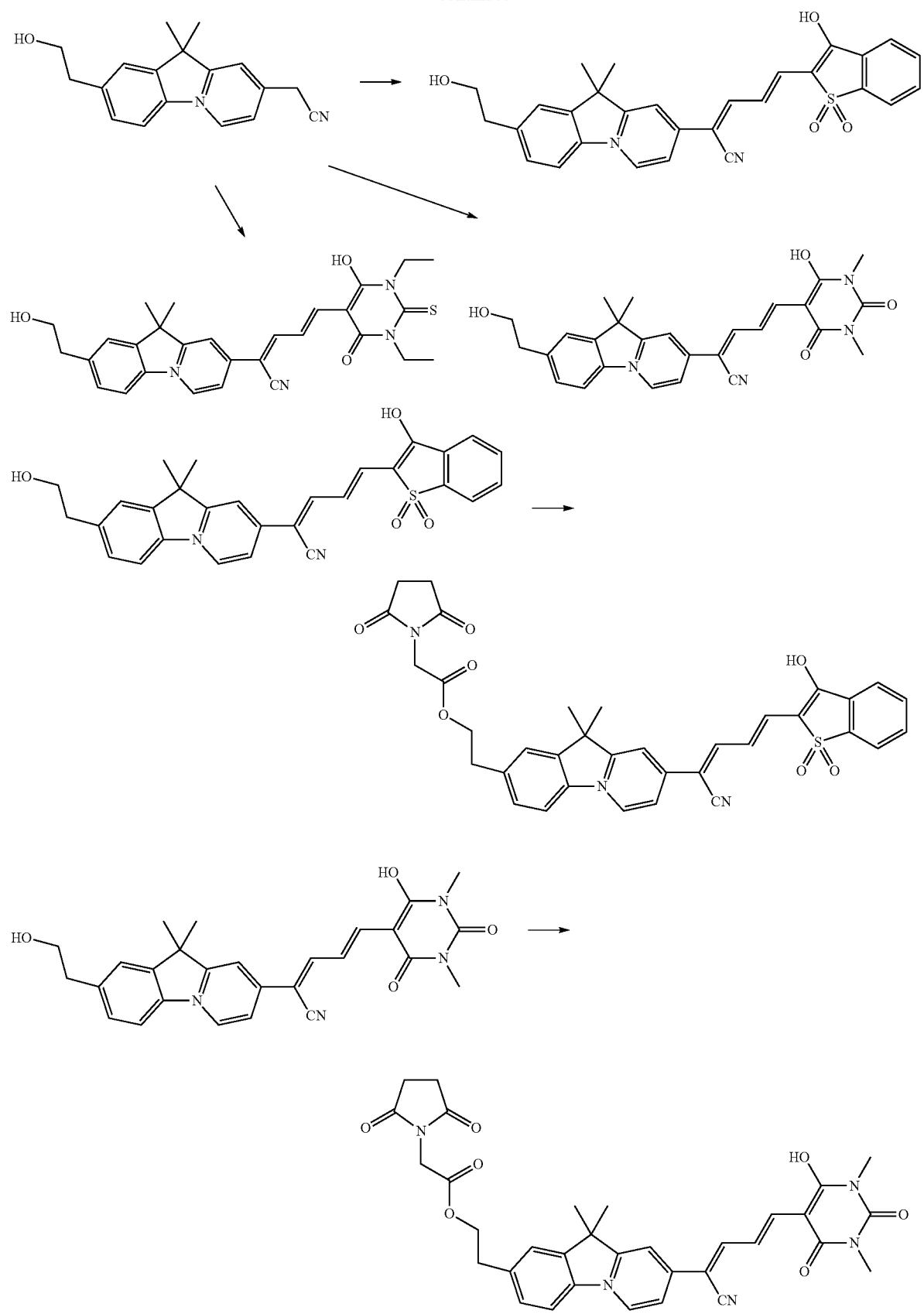

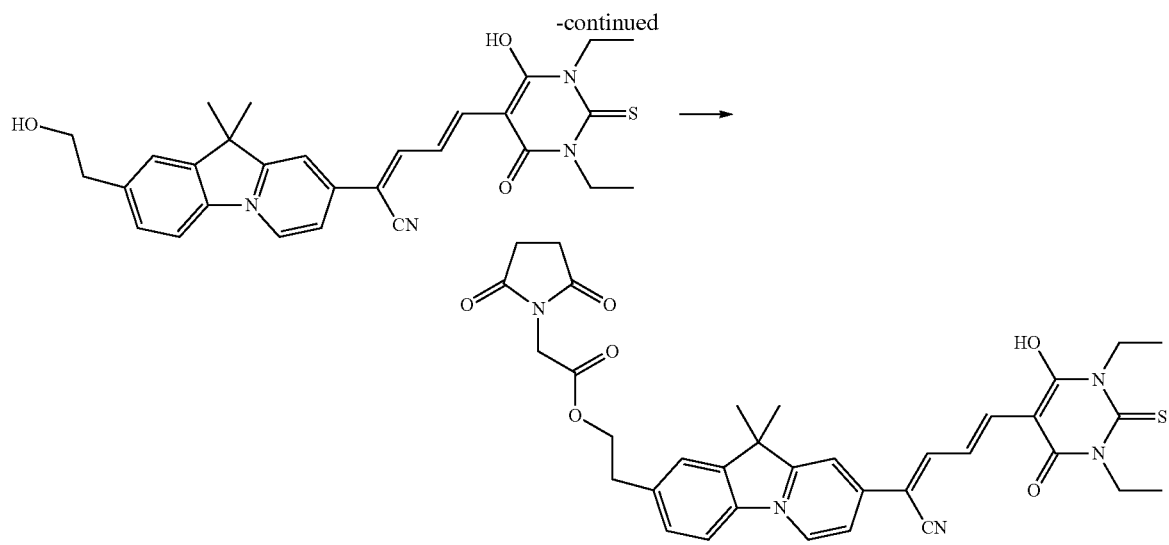
Representative succinimidyl esters of AI dyes are provided in Scheme 12.
Scheme 12. Representative succinimidyl esters of AI dyes.
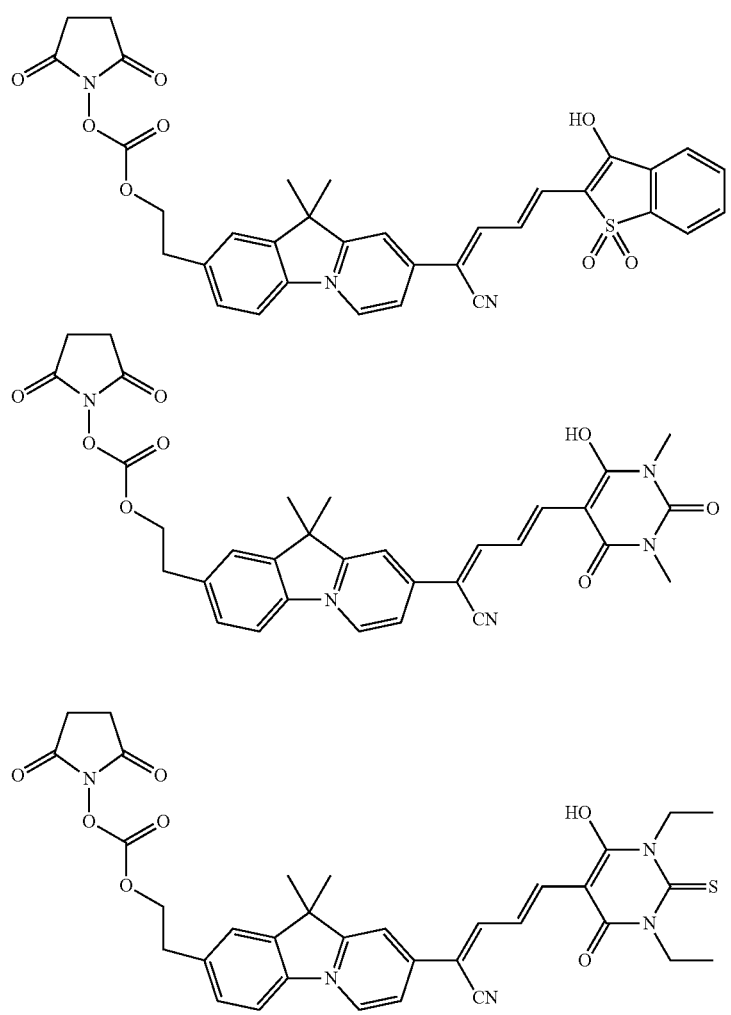

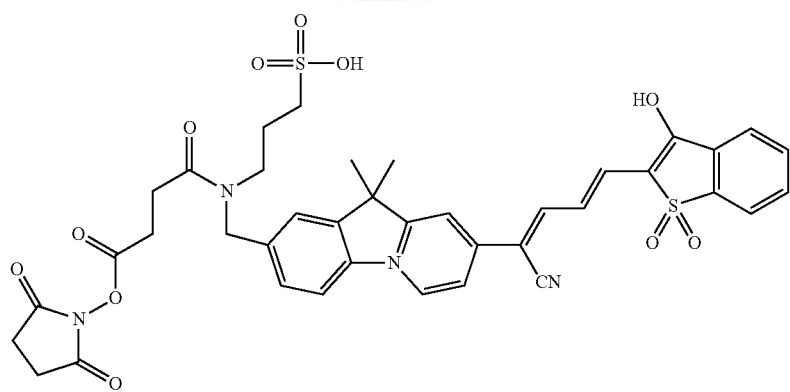
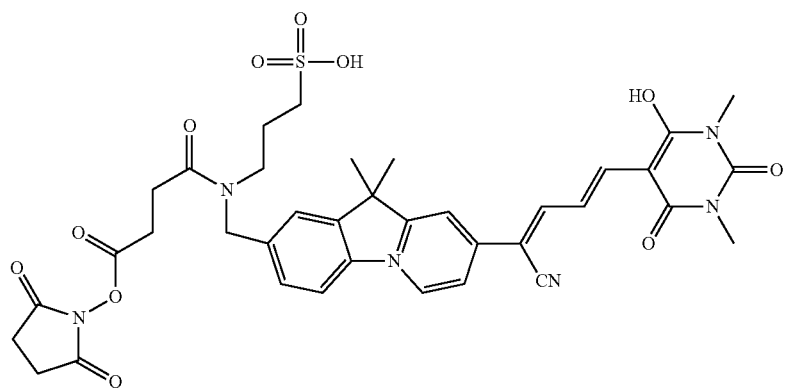
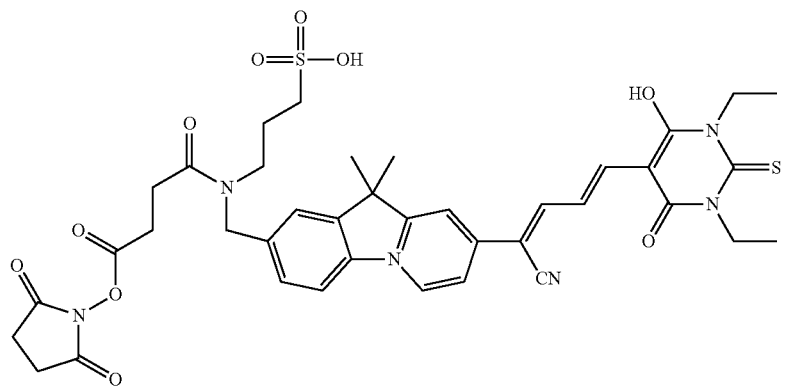

Example 8
Synthesis of Chloroacetamide and Iodoacetamide Esters of AI Dyes
A representative method for the synthesis of chloroacetamide and iodoacetamide esters of AI dyes is provided in Schemes 13-15. Representative chloroacetamide and iodoacetamide esters of AI dyes are provided in Scheme 16.
Scheme 13. Synthesis of Chloroacetamide esters of AI dyes.
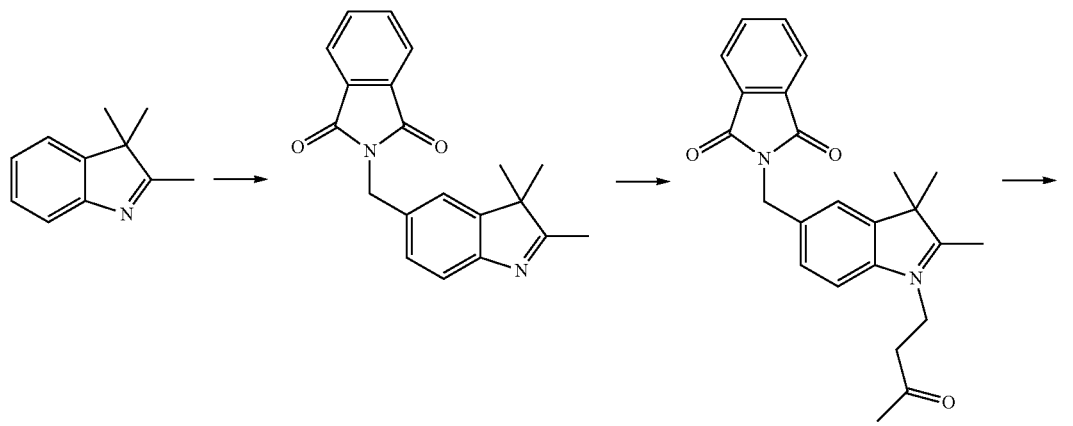
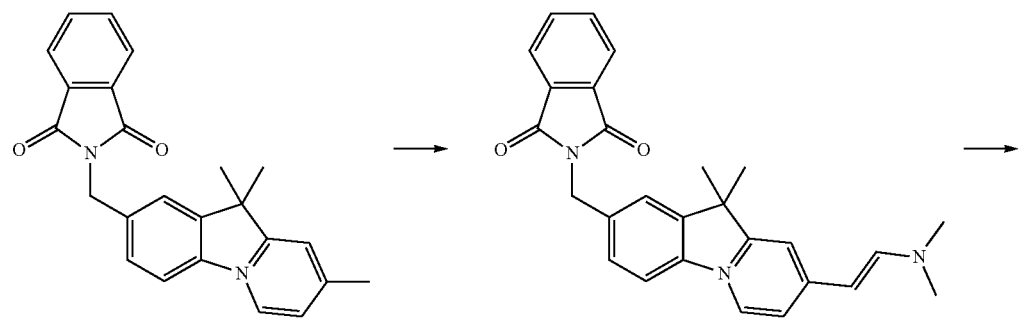
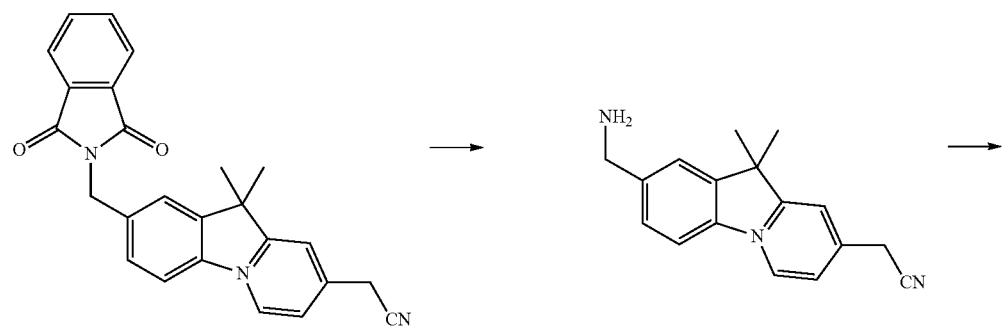

101
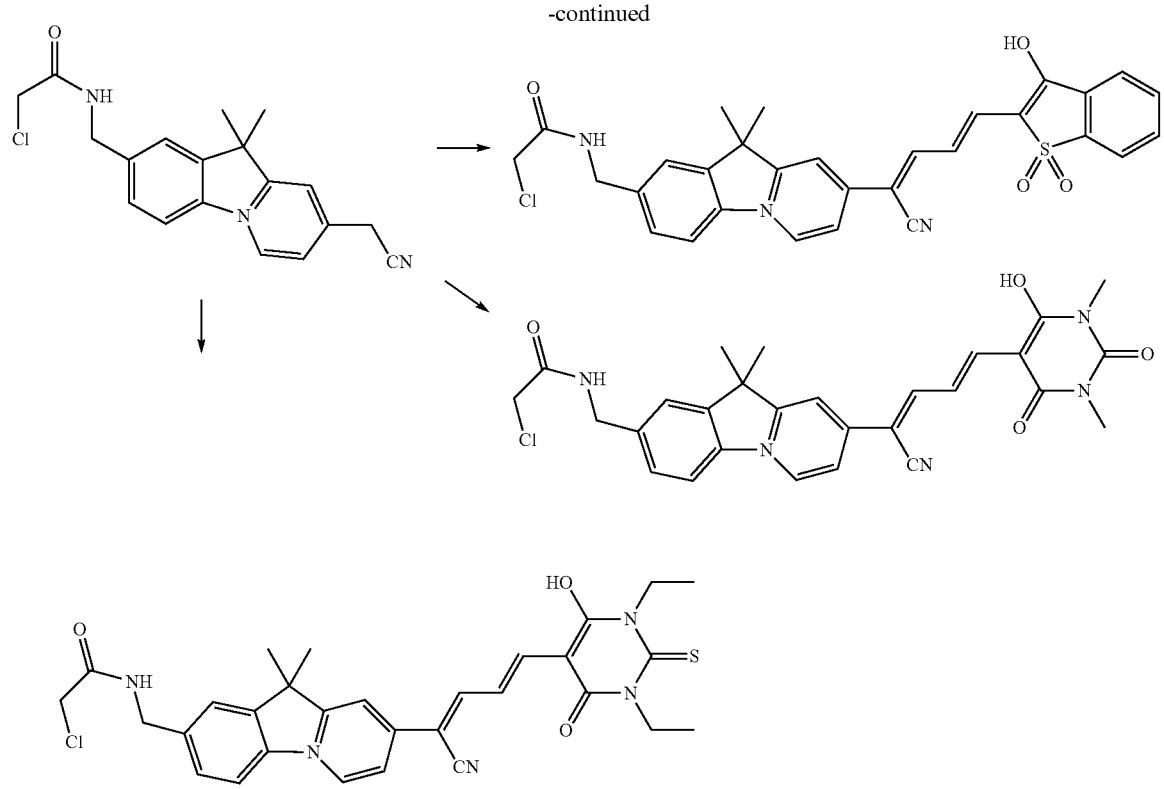
102
-continued
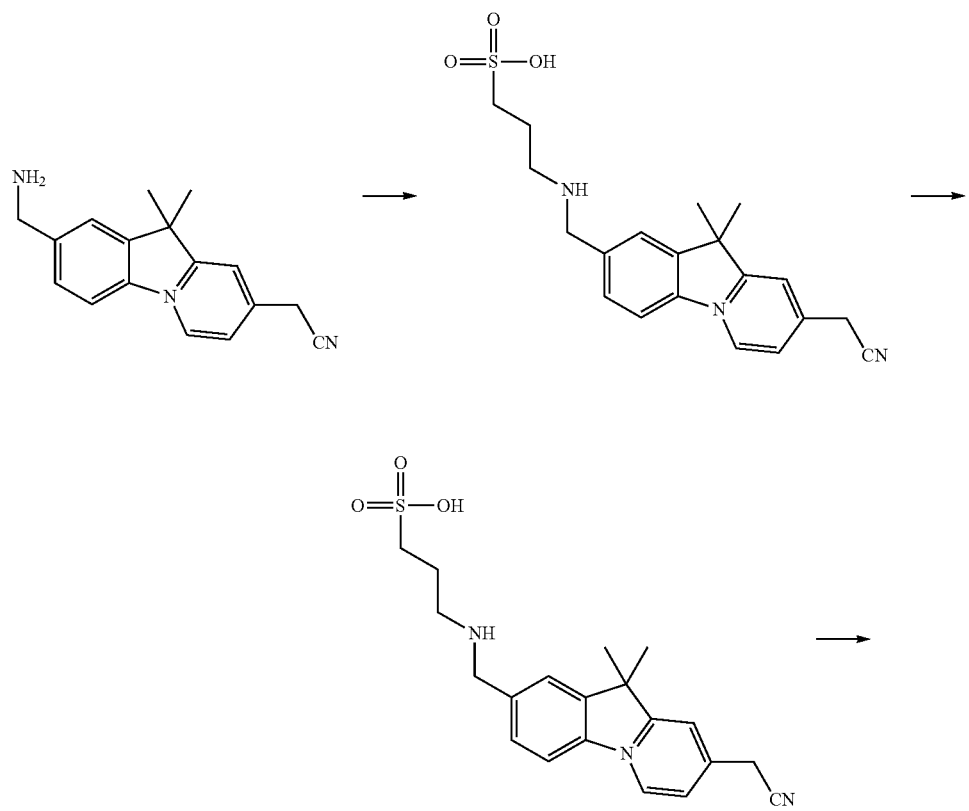
Scheme 14. Synthesis of Chloroacetamide esters of AI dyes.

103 104
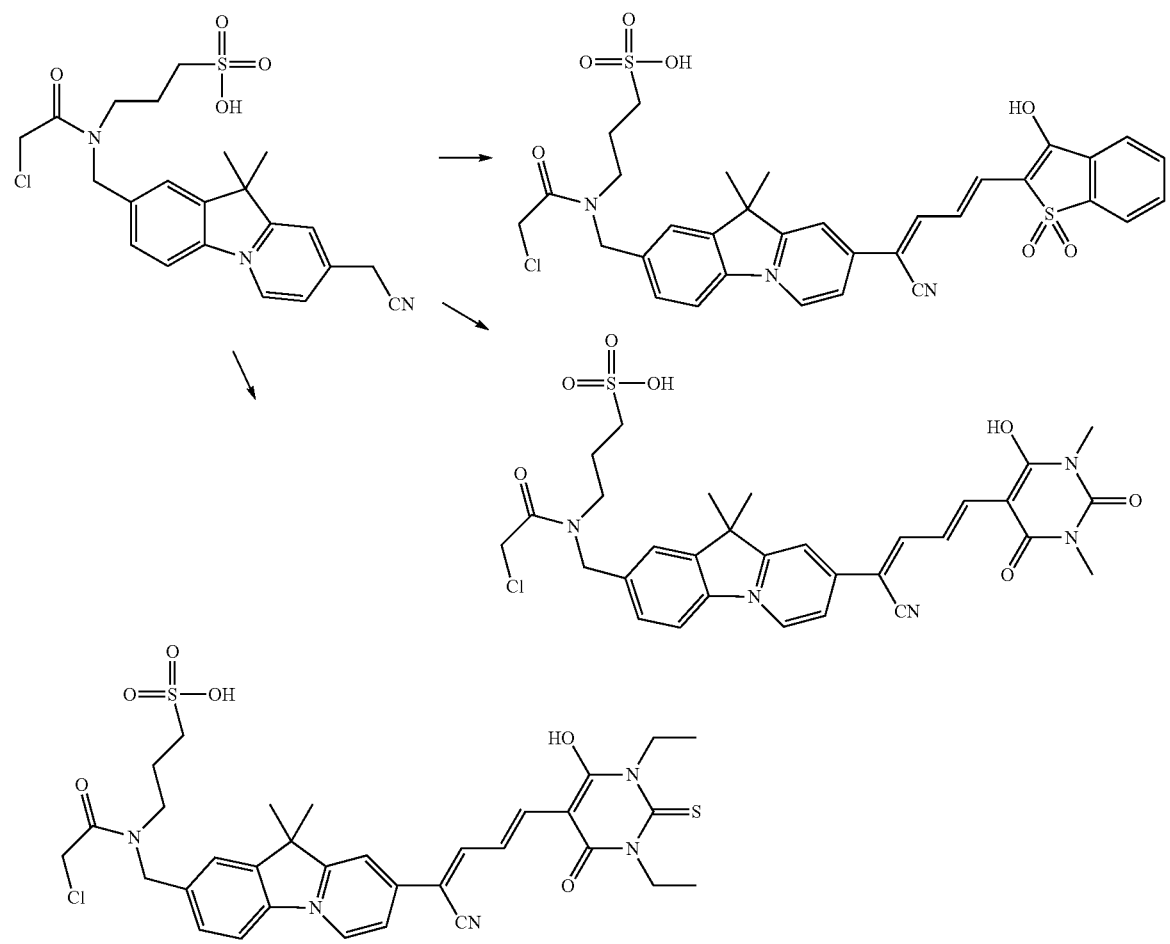
Scheme 15. Synthesis of Iodoacetamide esters of AI Dyes.
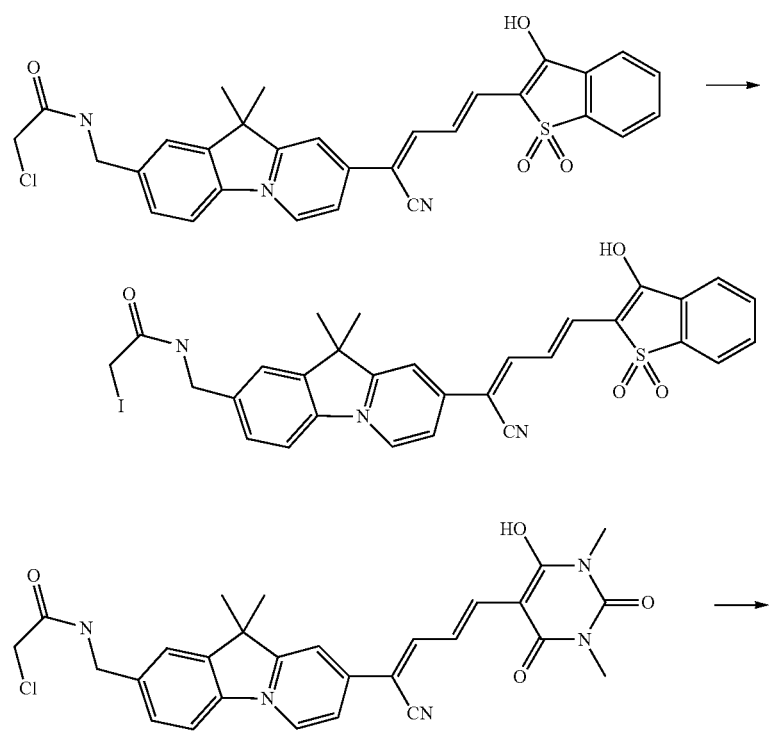

105
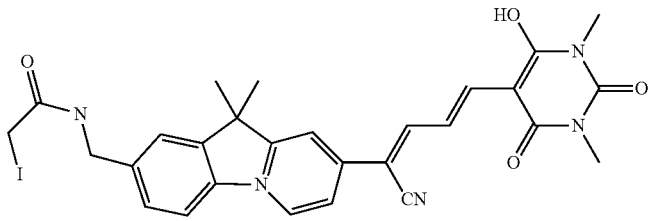
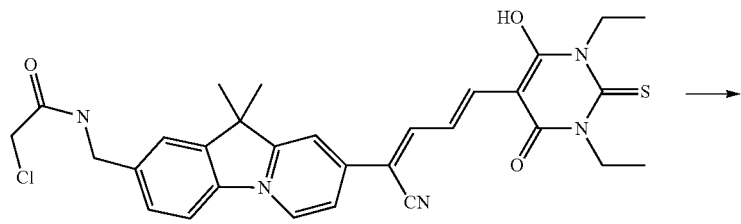
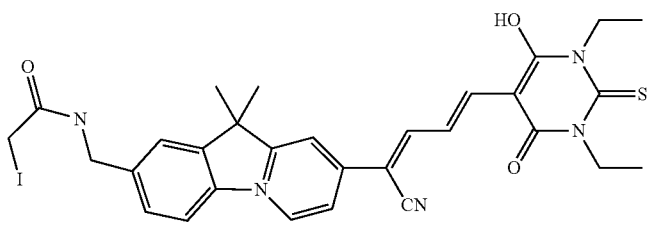
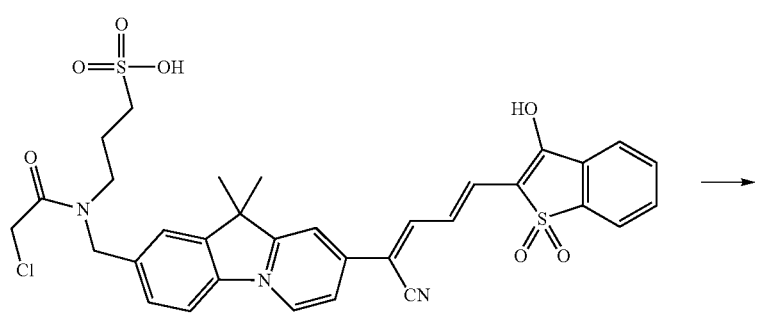
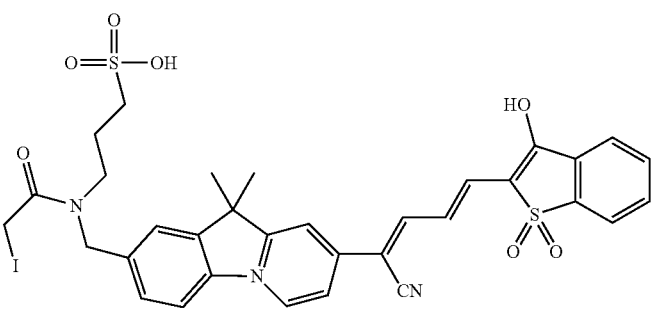
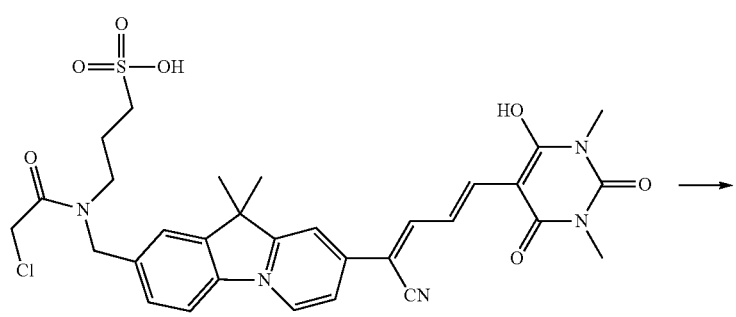
106

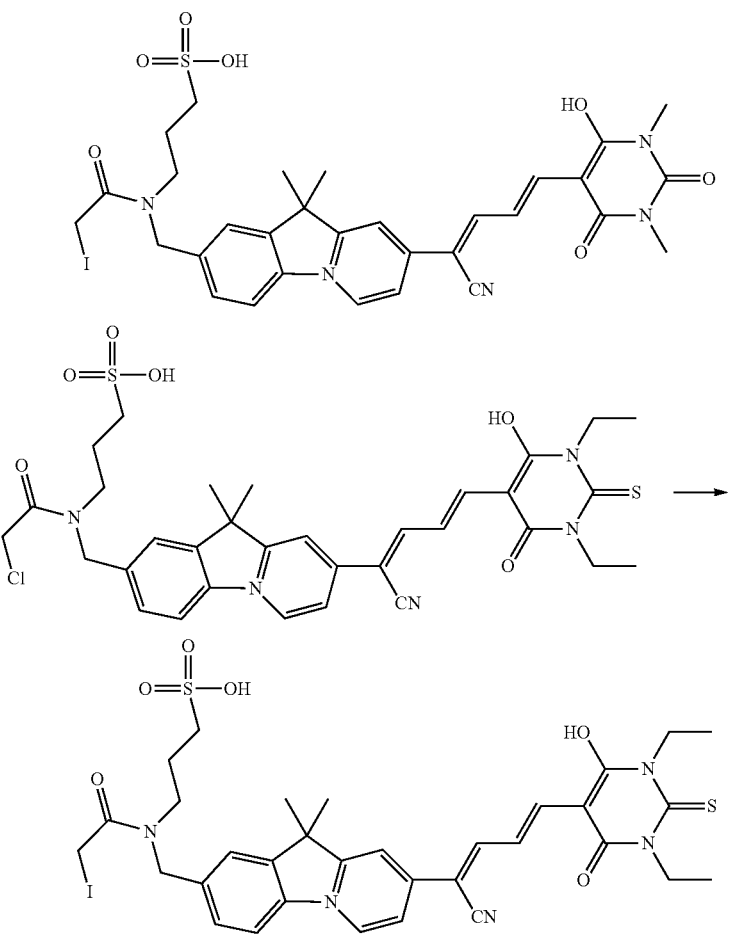
Scheme 16. Representative chloroacetamide esters and iodoacetamide esters of AI dyes.
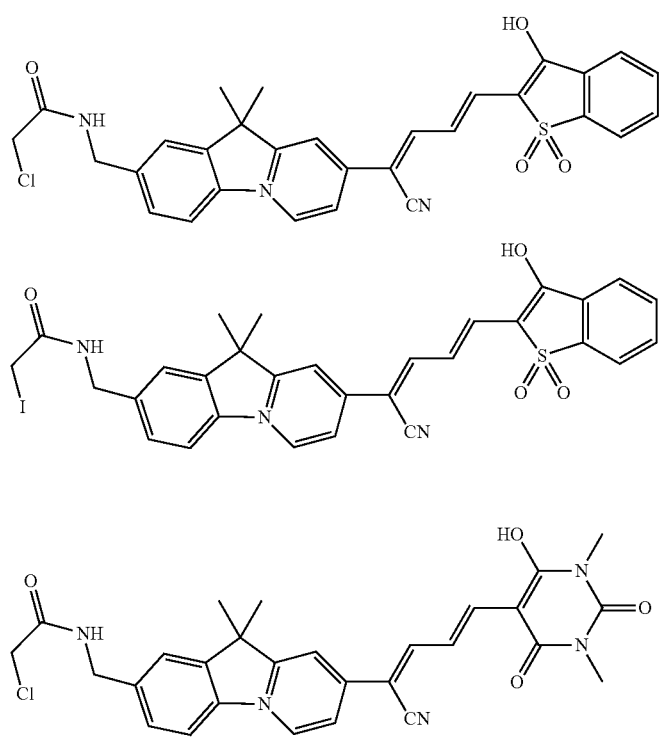

-continued
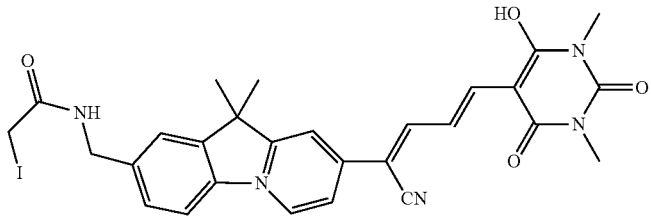
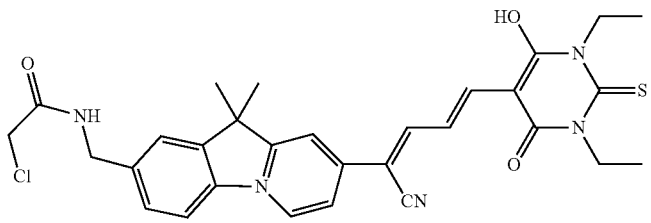
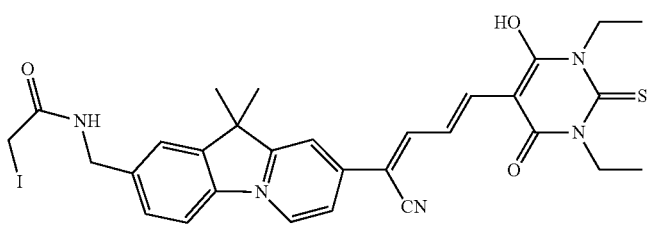
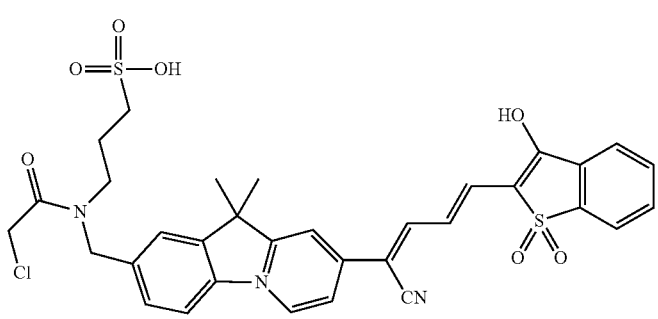
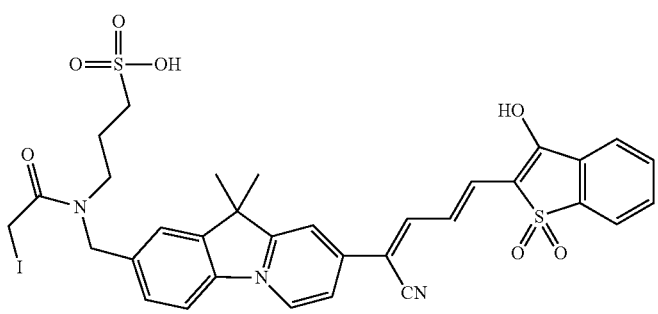
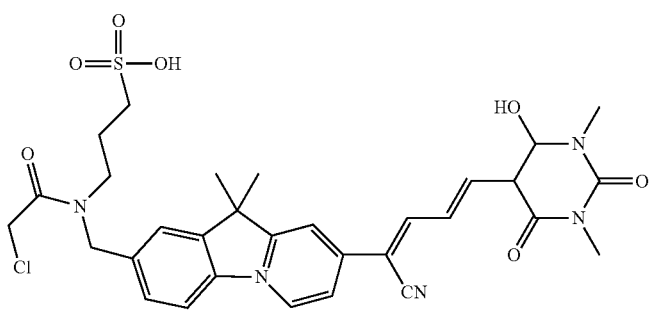

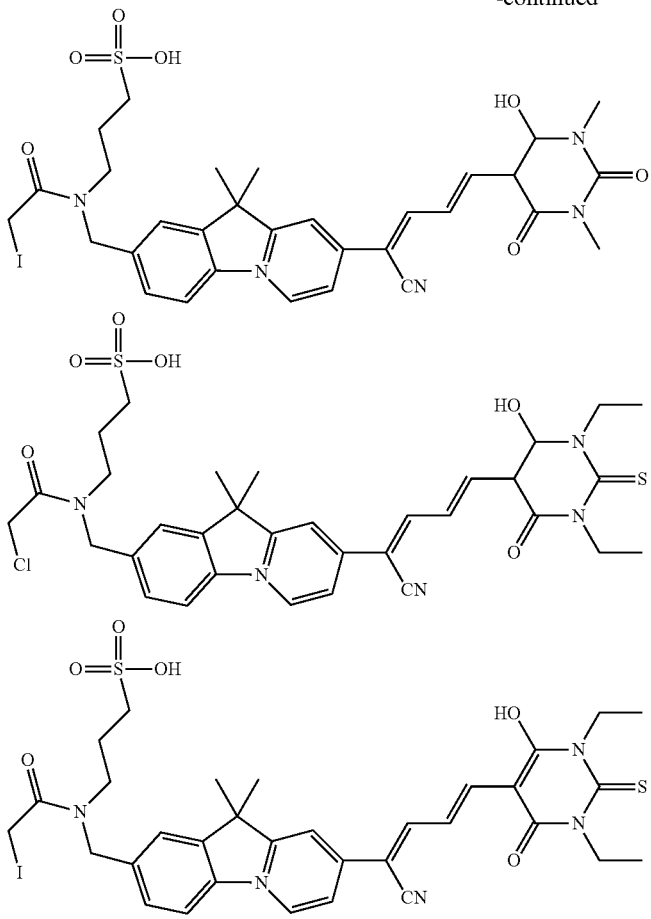

Example 9

Density Functional Theory (DFT) Studies

The presently disclosed subject matter provides merocyanine dyes exhibiting an enhanced solvent dependence of their absorbance and fluorescence emission maxima.

9.1. Overview

Density functional theory (DFT) calculations were performed to investigate the differences in optical properties between the presently disclosed dyes and merocyanine dyes known in the art. Absorption and emission energies were calculated for the presently disclosed dyes using DFT vertical self-consistent reaction field methods (VSCRF). Geometries of ground and excited states were optimized with a Conductor-like screening model (COSMO) and self-consistent-field (SCF) methods. The DFT-VSCRF calculations indicate that the presently disclosed dyes have enhanced zwitterionic character in the ground state and lower polarity in the excited state. As a result, the position of the absorption bands are strongly blue-shifted in more polar solvent (methanol compared to benzene) as predicted by the DFT spectral calculations. Inclusion of explicit H-bonding solvent molecules within the quantum model further enhances the predicted shifts and is consistent with the observed spectral broadening. Smaller spectral shifts in polar versus nonpolar solvent are predicted and observed for emission bands. The presently disclosed dyes exhibit large fluorescence quantum yields in polar hydrogen bonding solvents; qualitatively, the longest bonds along the conjugated chain at the excited $S_1$ state minimum are shorter in the more polar solvent, inhibiting photoisomerization.

The loss of photostability of the dyes is a consequence of the reaction with and electron transfer to singlet oxygen, starting oxidative dye cleavage. The calculated vertical ionization potentials of three dyes I-SO, AI-SO(4), and AI-BA(4) in benzene and methanol are consistent with their relative photobleaching rates; the charge distributions along the conjugated chains for the three dyes are similarly predictive of higher reaction rates for AI-SO(4) and AI-BA(4) than for I-SO.

9.2. Background

Fluorescent biosensors can provide for the visualization of signaling activity in individual, living cells, which can lead to insights into the spatio-temporal control of signaling pathways. See Hahn and Toutchkine, *Curr. Opin. Cell Biol.* 14:167-172 (2002); Kraynov et al., *Science* 290:333-337 (2000); Chamberlain and Hahn *Traffic* 1:755-762 (2000); and Hahn et al., *Nature* 359:736-738 (1992). Biosensors of protein conformational change have been produced by covalently labeling proteins with solvent-sensitive fluorescent dyes, such that protein conformational changes affect fluorescence intensity. See Giuliano and Taylor *Trends Biotech.* 16:135-140 (1998); Cerione, *Heterotrimeric G Proteins: Methods Enzymol.* 237:409-423 (1994); Nomanbhoy and Cerione, *J. Biol. Chem.* 271:10004-10009 (1996); Nomanbhoy and Cerione, *Biochem.* 38:15878-15884 (1999); Baburaj et al., *Biochim. Biophys. Acta Gen. Subj.* 1199:253-

265 (1994); Prendergast et al., *J. Biol. Chem.* 258:7541-7544 (1983); Rasmussen et al., *J. Biol. Chem.* 276:4717-4723 (2001); Morii et al., *J. Am. Chem. Soc.* 124:1138-1139 (2002); Daugherty and Gellman, *J. Am. Chem. Soc.* 121: 4325-4333 (1999).

Such dyes, for example, I-SO, I-TBA, S-SO, and S-TBA have been described for use in live cell biosensors and have long-wavelength absorbance and emission, high extinction coefficient and quantum yield, water solubility, photostability, and solvent sensitive fluorescence. See Toutchkine et al., *J. Am. Chem. Soc.* 125:4132-4145 (2003). A biosensor of Cdc42 activation made with one of these dyes showed a 3-fold increase in fluorescence intensity in response to GTP-binding by Cdc42. See id. Using dyes which respond to protein activity by changing fluorescence intensity presents difficulties during imaging, since the fluorescence intensity of dyes depends not only on protein conformational changes, but also on variations in cell thickness, uneven illumination, biosensor concentration, and the like. Such problems previously have been addressed by normalizing the biosensor signal against other, non-responsive fluorophores that distribute similarly to the biosensor in cells. See Nalbant et al., *Science* 305:1615-1619 (2004). This approach can present obstacles to quantitative studies of signaling networks. For example, the two fluorophores can bleach at different rates and site-specific attachment of two fluorophores to a biosensor can be challenging. The use of a second fluorophore for normalization is not necessary if the dye undergoes a solvent-dependent shift in its excitation or emission maxima, rather than simply an intensity change. Normalization can then be achieved by monitoring the fluorescence intensity of a single dye at two different wavelengths, rather than the relative intensities of two different dyes (see, e.g., FIG. 9). FIG. 9 shows an example of ratio imaging, illustrating that when covalently attached to a protein, the intensity of a particular dye molecule shifts between two spectra (e.g., spectrum A and spectrum B) as the dye environment is affected by protein conformational changes. Intensity A divided by intensity B reflects the protein environment, regardless of the overall intensity of the fluorescence;

Dyes known in the art possess moderate solvent-dependent shifts in excitation and/or emission wavelengths, but such shifts are not sufficient for ratio imaging in cells. The absorption and emission bands present red shifts for I-SO and blue shifts for S-TBA, with increasing solvent polarity. From $C_6H_6$ to MeOH, the absorption and emission wavelength shifts are 15 nm and 12 nm for I-SO, and are 17 nm and 11 nm for S-TBA, respectively. The shifts of the absorption and emission bands of S-SO and I-TBA in other solvents are smaller. See Toutchkine et al., *J. Am. Chem. Soc.* 125:4132-4145 (2003).

In contrast, the presently disclosed dyes have structural modifications that enhance the solvent-dependent shifts of excitation/emission wavelengths for merocyanine dyes. Depending on the relative electron donating and accepting strength of the "donor" (D) and "acceptor" (A) portions of the molecule, the dye can adopt different ground state structures, ranging from neutral through zwitterionic (see Scheme 17). As described by Marder and others, merocyanine dyes are insensitive to solvent polarity when their ground states are at the "cyanine limit" (C in Scheme 17), with equal contributions from the non-polar and the zwitterionic resonance structures. See Bourhill et al., *J. Am. Chem. Soc.* 116:2619-2620 (1994); Gorman and Marder, *Chem. Mater.* 7:215-220 (1995); and Bublitz et al., *J. Am. Chem. Soc.* 119:3365-3376 (1997). Dyes at the cyanine limit are characterized by equal dipole moments in the ground and excited states, so solvents affect both states similarly resulting in a minimal solvent-dependent change in absorption/emission maxima.

Scheme 17 shows resonance structures of merocyanine dyes.

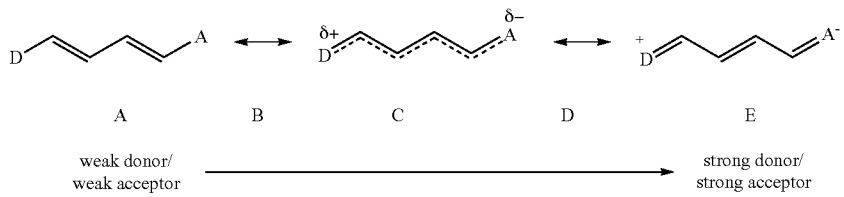

| A | B | C | D | E |
| weak donor/ weak acceptor | | → | | strong donor/ strong acceptor |

The presently disclosed subject matter demonstrates that by increasing the strength of an electron donor in the dye structure, the dye's ground state structure shifts to a more polar form (D in Scheme 17), and the dye has greater solvent-dependent absorption/emission wavelengths. This increase in donor strength can be accomplished by the introduction of a six-membered ring into the dye structure, which can lead to additional aromaticity when the dyes adopt the zwitterionic configuration.

The presently disclosed subject matter demonstrates that the absorption band positions of AI-SO(4), AI-TBA(4), and AI-BA(4) are highly solvent dependent. The shifts of the emission bands of AI-SO(4) and AI-BA(4), though not as significant as the absorption bands, are also largely increased. These two dyes are also highly fluorescent in polar solvents like methanol (MeOH).

The presently disclosed subject matter describes density functional theory (DFT) studies to examine how modifications of the donor structure affect dye solvent sensitivity. Several photophysical properties of these dyes were predicted and analyzed using the DFT vertical self-consistent reaction field (VSCRF), see Liu et al., *J. Phys. Chem. A* 108:3545-3555 (2004); Han et al., *ChemPhysChem* 4:1084-1094 (2003), method for calculating the spectra, plus a conductor like screening (COSMO) solvation model for optimizing geometries. See Klamt and Schüürmann, *J. Chem. Soc. Perkin Trans. II,* 799-805 (1993); Klamt, *J. Phys. Chem.* 99:2224-2235 (1995); Klamt and Jonas, *J. Chem. Phys.* 105: 9972-9981 (1996); and Pye and Ziegler *Theor. Chem. Acc.* 101:396-408 (1999).

The presently disclosed approach identifies structural features that can be incorporated into the dye molecule to enhance the solvent sensitivity of a broad range of merocyanine dyes.

Scheme 18. Structures of Representatives Dyes.
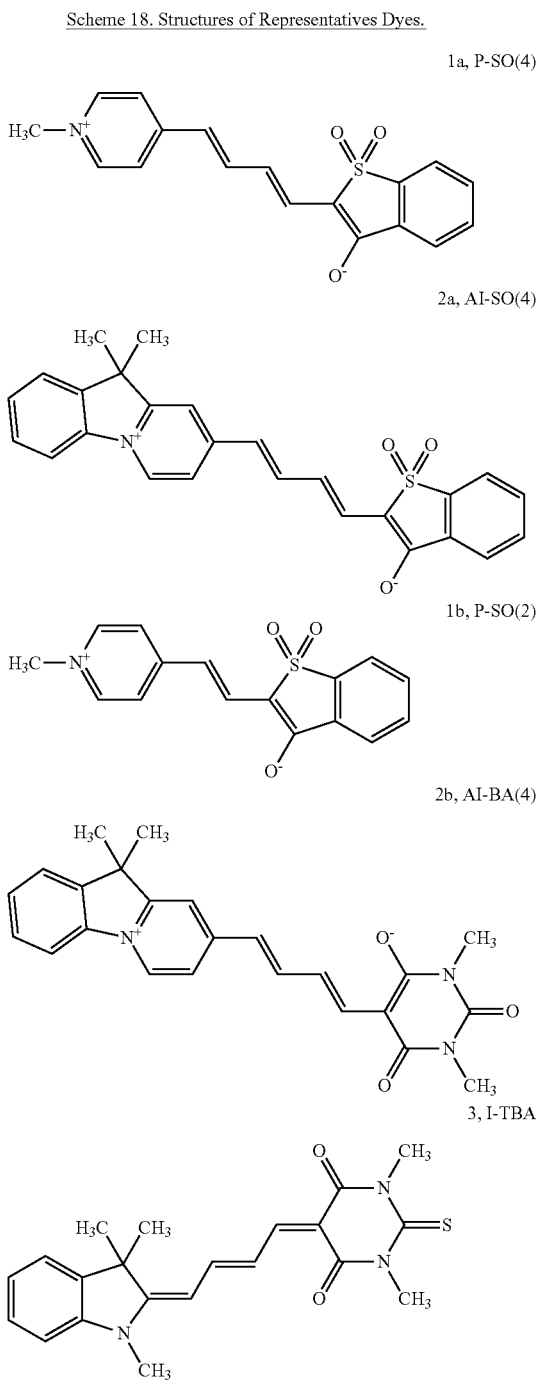
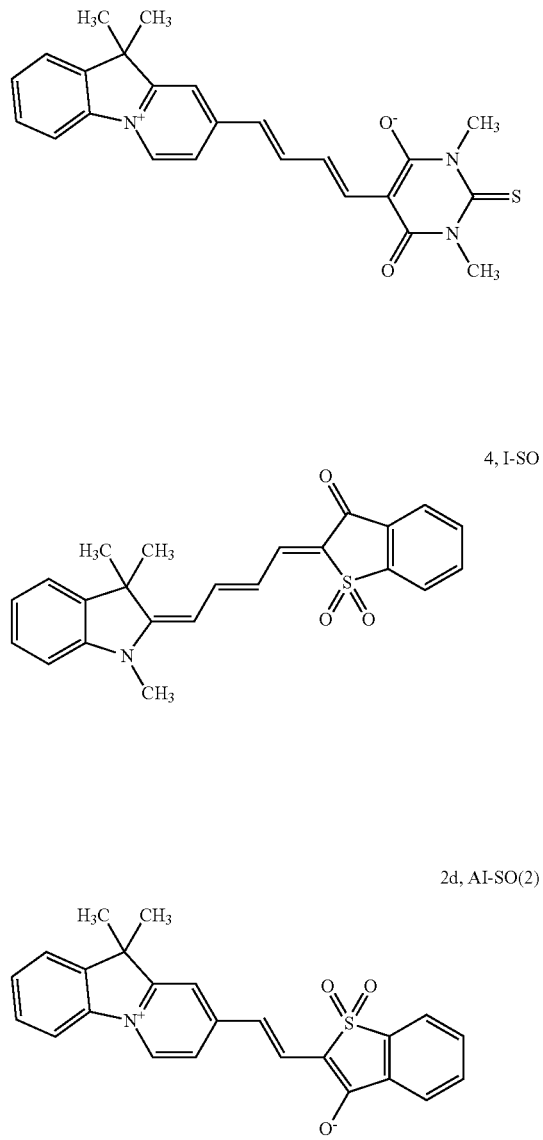
9.3. Methods
9.3.1. Synthesis
The synthesis of dyes 1a,b and 2a-d was accomplished according to Scheme 23. The synthesis of dyes 3 and 4 (I-TBA and I-SO) was described previously. See Toutchkine et al., *J. Am. Chem. Soc.* 125:4132-4145 (2003).
Scheme 19. Synthesis of dyes 1a, b, 2a-2d.
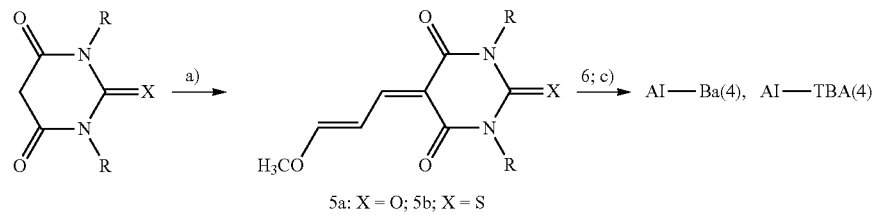

-continued

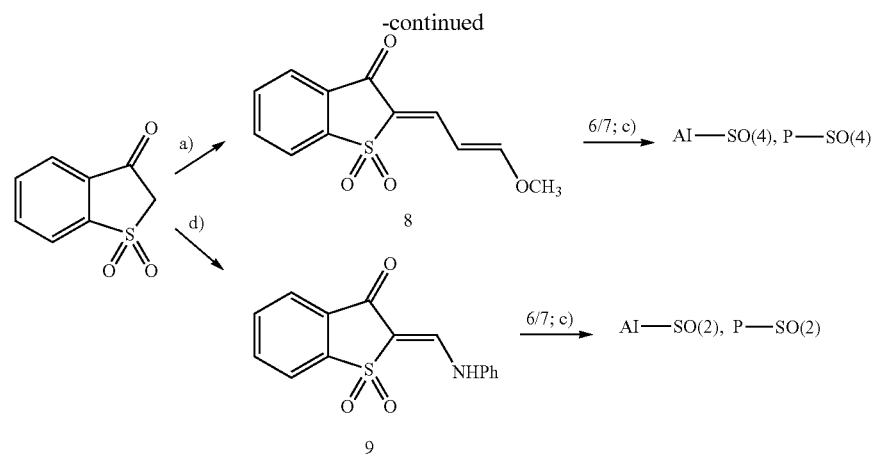

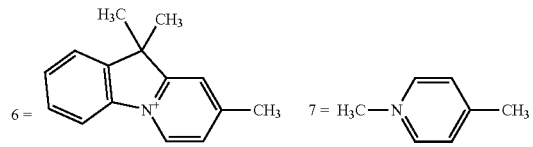

Conditions:
(a) malonoaldehyde bis(dimethyl acetal), CF₃COOH, 95° C., 2 hours.
(b) malonoaldehyde bis(dimethyl acetal), CF₃COOH, 130° C., 2 hours.
(c) N-Methylpiperidine, MeOH, reflux 30-60 min.
(d) diphenylformamidine, AcOH—Ac₂O, 120° C., 2 hours.

9.3.2. Computation

All quantum mechanical DFT calculations were performed using the Amsterdam Density Functional (ADF, Version 2000) package (ADF2000.02, SCM, Theoretical Chemistry, Vrije Universiteit, Amsterdam, The Netherlands). The parametrization of Vosko, Wilk and Nusair (VWN), Vosko et al., *Can. J. Phys.* 58:1200-1211 (1980), was used for the local density approximation term, and the corrections of Becke (B), see Becke, *Phys. Rev. A* 38:3098-3100 (1988), and Perdew (P), see Perdew, *Phys. Rev. B* 33:8822-8824 (1986); Perdew, *Phys. Rev. B* 34:7406-7406 (1986), were used for the non-local exchange and correlation terms. The molecular orbitals were expanded in an uncontracted triple-ζ Slater-type orbital basis set, along with a single set of polarization functions. The inner core shells of C(1s), N(1s), O(1s) and S(1s, 2p) were treated by the frozen core approximation. The accuracy parameter (accint) for the numerical integration grid was set to 4.0.

A density functional vertical self-consistent reaction field (VSCRF) solvation model for predicting vertical excitation energies and the solvatochromic shift of solvent sensitive dyes in different solutions has been reported. See Liu et al., *J. Phys. Chem. A* 108:3545-3555 (2004). This method has been applied to predict the UV absorption and emission blue shifts of Brooker's merocyanine from CHCl₃ to H₂O solutions with increasing solvent polarity, and the solvatochromic shifts of both the absorption and emission processes for S-TBA merocyanine, see Hahn et al., *J. Biol. Chem.* 265:20335-20345 (1990); Abdel-Halim's merocyanine, see Abdel-Halim, *J. Chem. Soc. Faraday Trans.* 89:55-57 (1993); the rigidified aminocoumarin C153, see Jones et al., *J. Phys. Chem.* 89:294-300 (1985); Gustavsson et al., *J. Phys. Chem. A* 102: 4229-4245 (1998); and McCarthy and Blanchard, *J. Phys. Chem.* 97:12205-12209 (1993); and Nile red, see Davis and Hetzer, *Anal. Chem.* 38:451-461 (1966); Sackett and Wolff, *Anal. Biochem.* 167:228-234 (1987), in different solutions, see Han et al., *ChemPhysChem* 4:1084-1094 (2003).

This VSCRF model was developed in the framework of density functional theory with ΔSCF methodology. Its implementation is based on a self-consistent reaction field (SCRF) development, where the solute molecule is computed by density functional theory in the presence of a solvent reaction field. See Chen et al., *J. Phys. Chem.* 98:11059-11068 (1994); Bashford, An Object-Oriented Programming Suite for Electrostatic Effects in Biological Molecules. In *Scientific Computing in Object-Oriented Parallel Environments (Lecture Notes in Computer Science)*, Ishikawa, Y.; Oldehoeft, R. R.; Reynders, J. V. W.; Tholburn, M., Eds. Springer: Berlin, 1997; Vol. 1343, pp 233-240; and Li et al., *J. Phys. Chem. A* 102: 6311-6324 (1998). The reaction field is evaluated from a finite-difference solution to the Poisson-Boltzmann equation and self-consistency between the reaction field and the electronic structure of the solute is achieved by iteration. The SCRF calculation applied to a solute geometry allows the electronic structure relaxation in both the solute and the solvent and, implicitly, the orientational (geometry) relaxation of the solvent. Once the SCRF calculation on the ground state ($S_0$) state (or the first excited singlet state ($S_1$) is achieved, the VSCRF procedure on the excited state (or the ground state) allows only the electronic structure reorganization for both the solute and solvent, and the vertical excitation (or emission) in solution is then obtained. The detailed principles and procedures for VSCRF calculations in both absorption and emission processes, including the ΔSCF spin-decontamination methodology for the first excited singlet state (S₁) energy, can be found in Liu et al., *J. Phys. Chem. A* 108:3545-3555 (2004); and Han et al., *ChemPhysChem* 4:1084-1094 (2003).

The solute geometries in $C_6H_6$ and MeOH were optimized using the COSMO (Conductor like Screening Model) model in ADF. See Klamt and Schüürmann, *J. Chem. Soc. Perkin Trans. II*, 799-805 (1993); Klamt, *J. Phys. Chem.* 99:2224-2235 (1995); Klamt and Jonas, *J. Chem. Phys.* 105:9972-9981 (1996); and Pye and Ziegler *Theor. Chem. Acc.* 101: 396-408 (1999). The COSMO model is a dielectric solvent continuum model in which the solute molecule is embedded in a molecular-shaped cavity surrounded by a dielectric medium with given dielectric constant ∈. For the absorption process, the $S_0$ state of the solute was relaxed in different solvent dielectrics. Correspondingly, for the emission process, the geometry optimizations were performed on the $S_1$ state. An electron was promoted from β-HOMO to β-LUMO during the $S_1$ state geometry optimizations. The SCRF/VSCRF calculations then can be performed on the COSMO-optimized geometries.

9.4. Results

Merocyanines with more zwitterionic ground states (dyes 1a, 1b and 2a-d in Scheme 18) were compared to merocyanines that should be closer to the cyanine limit (dyes 3 and 4 in Scheme 18). The more zwitterionic merocyanines were made by incorporating a strong donor ring, either 4-pyridine or 10H-pyrido[1,2-a]indolenine, into the structures. These rings stabilize the polar, zwitterionic form of the dyes in the ground state, because of the enhanced aromaticity of the zwitterionic resonance form (Scheme 20).

and AI-TBA(4). These properties also are compared in non-polar $C_6H_6$ and in polar MeOH solvents.

9.4.1. Conformations of the Dye Molecules

Using the COSMO model in ADF2000, all the possible conformations for the dyes 2a, 2b, 2c, 3, and 4 were geometry optimized in $C_6H_6$ (∈=2.3) and in MeOH (∈=32.6). NMR spectra of these dyes were consistent with an all-trans configuration of the central polymethine bridge. The relative energies of the different conformers are given in Table 9 and the lowest energy structures in MeOH, with numbering conventions, are shown in FIG. 10. Further calculations are then based on these conformations.

TABLE 9

Calculated Relative Energies (kcal mol⁻¹) of the Different Conformers of Each Dye Molecule in $C_6H_6$ and MeOH.[a]

| Dye | Solvent | Conformers | | | |
|---|---|---|---|---|---|
| | | 1 trans 4 9 trans 5 | 1 cis 4 9 trans 5 | 1 trans 4 9 cis 5 | 1 cis 4 9 cis 5 |
| I-TBA | $C_6H_6$ | 0.00 | 2.42 | | |
| | MeOH | 0.00 | 2.45 | | |
| AI-TBA(4) | $C_6H_6$ | 0.00 | 0.38 | | |
| | MeOH | 0.00 | 0.56 | | |
| AI-BA(4) | $C_6H_6$ | 0.00 | 1.72 | | |
| | MeOH | 0.00 | 0.63 | | |
| I-SO | $C_6H_6$ | 0.05 | 0.66 | 0.00 | 1.66 |
| | MeOH | 0.00 | 0.80 | 0.43 | 1.95 |
| AI-SO(4) | $C_6H_6$ | 0.56 | 0.00 | 1.72 | 1.08 |
| | MeOH | 0.75 | 0.00 | 2.04 | 2.03 |

[a]See structures in FIG. 10 for the atomic labeling. Here for instance, "1 trans 4, 9 trans 5" means that "atom 1 is trans to atom 4, and atom 9 is trans to atom 5".

Scheme 20. Ground state of merocyanine dyes with and without aromatic stabilization of a charged donor ring. The incorporation of an additional 6-membered ring strongly favors the charged zwitterionic resonance form.

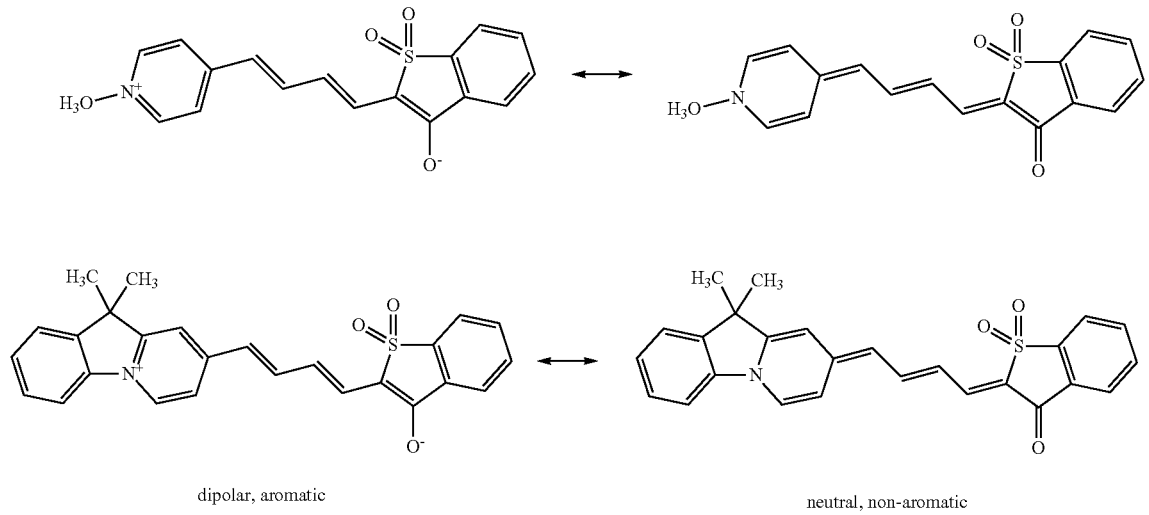

dipolar, aromatic    neutral, non-aromatic

The presently disclosed subject matter describes the use of DFT calculations, evaluating geometries, excitation and emission energies, H-bonding effects, molecular orbital and bonding characters, dipole moments, and the atomic charge distributions for dyes I-SO (4), I-TBA (3), AI-SO(4) (2a), AI-BA(4) (2b), and AI-TBA(4) (2c), to examine why the solvent dependencies in absorption and emission, the fluorescence quantum yield, and photobleaching properties change from I-SO to AI-SO(4), and from I-TBA to AI-BA(4)

9.4.2. Absorption Spectra

The experimental absorption data for the dyes are summarized in Table 10, and FIG. 11. With decreasing solvent polarity, the absorption maximum of dyes 1a-b, 2a-d shifted to longer wavelengths, and the intensity of the transition increased (Table 10, FIG. 11).

TABLE 10

Observed Absorption Properties of Dyes 1a-b, 2a-d, 3, and 4.

| Solvent | 3<br>I-TBA<br>$\lambda_{max}$/nm<br>($\epsilon$) | 4<br>I-SO<br>$\lambda_{max}$/nm<br>($\epsilon^a$) | 2a,<br>AI-SO(4)<br>$\lambda_{max}$/nm<br>($\epsilon$) | 2b,<br>AI-BA(4)<br>$\lambda_{max}$/nm<br>($\epsilon$) | 2c,<br>AI-TBA(4)<br>$\lambda_{max}$/nm<br>($\epsilon$) | 2d,<br>P-SO(4)<br>$\lambda_{max}$/nm<br>($\epsilon$) | 1a,<br>P-SO(2)<br>$\lambda_{max}$/nm<br>($\epsilon$) | 1b,<br>AI-SO(2)<br>$\lambda_{max}$/nm<br>($\epsilon$) |
|---|---|---|---|---|---|---|---|---|
| MeOH | 583<br>(173000) | 586<br>(143000) | 610<br>(65000) | 585<br>(83000) | 576<br>(38000) | 580<br>(54000) | 505<br>(57000) | 542<br>(92000) |
| EtOH | — | —$^b$ | 636<br>(83000) | 604<br>(104000) | 603<br>(46000) | 557<br>(61000) | 514<br>(65000) | 549<br>(111000) |
| i-PrOH | — | — | 648<br>(122000) | 614<br>(132000) | 618<br>(50000) | 597<br>(68000) | 518<br>(72000) | 553<br>(132000) |
| BuOH | 589<br>(190000) | 587<br>(134000) | 650<br>(118000) | 615<br>(154000) | 619<br>(53000) | 593<br>(64000) | 519<br>(67000) | 554<br>(120000) |
| OcOH | 590<br>(180000) | 587<br>(125000) | 660<br>(150000) | 628<br>(143000) | 633<br>(97000) | 612<br>(80000) | 524<br>(72000) | 559<br>(150000) |
| DMF | 589<br>(183000) | 586<br>(143000) | 651<br>(154000) | 625<br>(146000) | 616<br>(52000) | 604<br>(99000) | 522<br>(92000) | 556<br>(157000) |
| DMSO | — | — | 644<br>(118000) | 617<br>(122000) | 607<br>(56000) | 599<br>(77000) | 520<br>(75000) | 555<br>(126000) |
| $CH_3CN$ | — | — | 642<br>(142000) | 621<br>(141000) | 615<br>(54000) | 596<br>(93000) | 546<br>(89000) | 549<br>(149000) |
| $CH_2Cl_2$ | — | — | 667<br>(278000) | 647<br>(224000) | 655<br>(104000) | 629<br>(187000) | 529<br>(128000) | 561<br>(218000) |
| $C_6H_6$ | 584<br>(127000) | 571<br>(109000) | 679<br>(240000) | 662<br>(±201000) | 683<br>(135000) | 644<br>(178000) | 538<br>(169000) | 570<br>(235000) |

Such a hypsochromic (blue) shift, e.g., to shorter wavelength, higher frequency, is similar to that of Brooker's merocyanine (Scheme 21), a known dye with a ground state predominantly in the zwitterionic form. See Liu et al., *J. Phys. Chem. A*, 108, 3545-3555 (2004).

Scheme 21. Brooker's merocyanine.

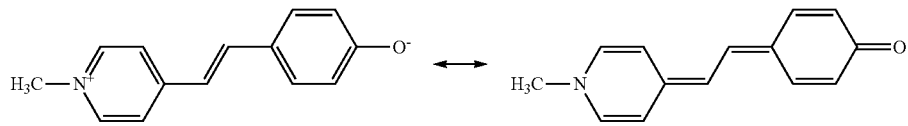

For the presently disclosed dyes with stronger donor rings, a decrease in solvent polarity resulted in destabilization of the zwitterionic form and moved the dye ground state toward the "cyanine limit," thereby increasing the contribution from the non-polar form. The calculated central C—C bond lengths of the ground state geometries are presented in Table 11. The solute structures vary with solvent polarity. Strong bond length alternations (BLA) were found for merocyanines 2a-c in MeOH, where dyes predominantly exist as zwitterions. The alternations were diminished in benzene indicating a ground state more like the "cyanine-limit." For I-TBA and I-SO, the average BLA was small, suggesting that in both solvents the ground states of the dyes are close to the cyanine limit.

TABLE 11

DFT Calculated Central C—C Bond Lengths (Å) of the
Ground State Dye Molecules in $C_6H_6$ and in MeOH.

| Solvent | Bond | I-TBA | AI-<br>TBA(4) | AI-<br>BA(4) | I-SO | AI-<br>SO(4) |
|---|---|---|---|---|---|---|
| $C_6H_6$ | $C_2$—$C_3$ | 1.394 | 1.413 | 1.411 | 1.386 | 1.412 |
| | $C_3$—$C_4$ | 1.404 | 1.403 | 1.404 | 1.409 | 1.395 |

TABLE 11-continued

DFT Calculated Central C—C Bond Lengths (Å) of the
Ground State Dye Molecules in $C_6H_6$ and in MeOH.

| Solvent | Bond | I-TBA | AI-<br>TBA(4) | AI-<br>BA(4) | I-SO | AI-<br>SO(4) |
|---|---|---|---|---|---|---|
| | $C_4$—$C_5$ | 1.393 | 1.403 | 1.401 | 1.383 | 1.394 |
| | $C_5$—$C_6$ | 1.397 | 1.396 | 1.399 | 1.404 | 1.401 |
| | $C_6$—$C_7$ | 1.402 | 1.408 | 1.404 | 1.382 | 1.386 |
| BLA($C_6H_6$) | | 0.007 | 0.009 | 0.010 | 0.022 | 0.005 |
| MeOH | $C_2$—$C_3$ | 1.401 | 1.430 | 1.427 | 1.398 | 1.429 |
| | $C_3$—$C_4$ | 1.395 | 1.389 | 1.393 | 1.399 | 1.382 |
| | $C_4$—$C_5$ | 1.402 | 1.419 | 1.416 | 1.396 | 1.410 |
| | $C_5$—$C_6$ | 1.390 | 1.384 | 1.387 | 1.396 | 1.388 |
| | $C_6$—$C_7$ | 1.415 | 1.426 | 1.421 | 1.395 | 1.404 |
| BLA(MeOH) | | 0.009 | 0.038 | 0.032 | 0.0005 | 0.035 |

BLA = absolute value of $\{|(C_2—C_3) - (C_3—C_4)| + |(C_4—C_5) - (C_5—C_6)|\}/2$ The structure changes of the solutes with increasing solvent polarity from $C_6H_6$ are consistent with the changes of the solute dipole moment (see Table 12). The $S_0$ state dipole moments ($\mu_{S0}$) are increased moderately by 6.15 and 4.57 D for I-TBA and I-SO, and significantly by 9.70, 8.82, and 8.45 D for AI-TBA(4), AI-BA(4), and AI-SO(4), respectively, from $C_6H_6$ to MeOH solutions.

TABLE 12

SCRF/VSCRF Calculated (Cal) and Experimentally (Exp) Observed
Absorption ($E_{abs}$) Energies (eV), and the Relaxed $S_0$ State ($\mu_{S0}$)
and Vertical $S_1$ ($\mu^v_{S1}$) State Dipole Moments (D)
for the Dyes in $C_6H_6$ and in MeOH.

Absorption

| Solute | Solvent | $\mu_{S0}$ | $\mu^v_{S1}$ | Cal | $E_{abs}$ Exp |
|---|---|---|---|---|---|
| I-TBA | $C_6H_6$ | 16.53 | 17.86 | 1.611 | 2.123 (585 nm) |
|  | MeOH | 22.68 | 22.60 | 1.599 | 2.127 (583 nm) |
| AI-TBA(4) | $C_6H_6$ | 22.84 | 19.77 | 1.349 | 1.816 (683 nm) |
|  | MeOH | 32.54 | 25.19 | 1.581 | 2.153 (576 nm) |
| AI-BA(4) | $C_6H_6$ | 19.78 | 18.46 | 1.411 | 1.873 (662 nm) |
|  | MeOH | 28.60 | 21.60 | 1.583 | 2.120 (585 nm) |
| I-SO | $C_6H_6$ | 10.07 | 16.91 | 1.637 | 2.172 (571 nm) |
|  | MeOH | 14.64 | 17.63 | 1.556 | 2.116 (586 nm) |
| AI-SO(4) | $C_6H_6$ | 17.71 | 18.56 | 1.401 | 1.826 (679 nm) |
|  | MeOH | 26.16 | 23.83 | 1.536 | 2.120 (585 nm) |

The change of the solute dipole moment in different solutions, or upon $S_0 \rightarrow S_1$ transitions, is caused by charge rearrangement or intramolecular charge transfer. Referring now to FIG. 12, the molecular orbital plots for the electron in the HOMO of the $S_0$ state and the $\pi \rightarrow \pi^*$ promoted electron in the $S_1$ state of dye 2b, AI-BA(4) in $C_6H_6$ and in MeOH.

The contributions of the atomic $\pi$ orbitals to the HOMO vary with solvent type. In $C_6H_6$ solution, the electron in the HOMO is mainly localized at $C_7(17.2\%)$, $C_3(17.0\%)$, $C_5(16.3\%)$, $N_{18}(6.6\%)$, $C_{16}(5.2\%)$, $O_{11}(4.6\%)$, $C_1(4.2\%)$, $O_{10}(3.8\%)$, and $C_2(2.5\%)$. In MeOH solution, the localization of the electron in the HOMO is shifted rightward and localized at the atoms of $C_3(17.7\%)$, $C_7(17.3\%)$, $C_5(16.6\%)$, $N_{18}(5.3\%)$, $O_{11}(5.0\%)$, $C_{16}(4.7\%)$, $O_{10}(4.2\%)$, $C_1(4.2\%)$, $C_6(3.4\%)$, and $O_{15}(2.4\%)$. Not only the electron in the HOMO, but also the distribution of other electrons vary with solvent polarity; therefore the dipole moment of $S_0$ state AI-BA(4) is substantially increased with increasing solvent polarity from $C_6H_6$ to MeOH. During the $\pi \rightarrow \pi^*$ transition, the solute dipole moment decreases. The promoted electron in the $\pi^*$ orbital moved leftward. In $C_6H_6$ solution, it is mainly localized at the atoms of $C_4(14.1\%)$, $C_2(14.0\%)$, $C_6(13.6\%)$, $C_{19}(9.7\%)$, $N_{18}(7.2\%)$, $C_{17}(5.4\%)$, $C_5(5.1\%)$, $C_{23}(3.2\%)$, $O_{10}(3.1\%)$, $C_{25}(3.1\%)$, $C_8(3.1\%)$, and $O_{11}(2.9\%)$ for the vertical $S_1$ state. In MeOH, the contributions change to $C_4(14.4\%)$, $C_6(13.9\%)$, $C_2(13.0\%)$, $N_{18}(8.9\%)$, $C_{19}(8.7\%)$, $C_{17}(5.5\%)$, $C_{16}(4.9\%)$, $C_3(3.6\%)$, $C_{23}(3.1\%)$, $C_8(3.0\%)$, $C_{25}$ (2.9%), and $C_9(2.7\%)$.

When the solute dipole moment in the excited state is larger than that in the ground state, the excited state is better stabilized in polar solvents relative to the ground state. With increasing solvent polarity, a red shift for the absorption bands can occur. On the other hand, a blue shift with increasing solvent polarity can occur if the solute dipole moment in the ground state is larger than that in the excited state. During the $\pi \rightarrow \pi^*$ excitation process, the solute dipole moments of AI-TBA(4), AI-BA(4) and AI-SO(4) all decrease in MeOH solution (Table 12). Their absorption bands shift to the blue with increasing solvent polarity from $C_6H_6$ to MeOH. By contrast, the dipole moment of I-SO increases during the $\pi \rightarrow \pi^*$ transition, and a red shift of its absorption band from $C_6H_6$ to MeOH solution is observed.

The SCRF/VSCRF calculated vertical excitation energies of these molecules also are presented in Table 12. The $\Delta$SCF procedure of DFT method normally underestimates the absolute value of the $S_1$ state energy, and therefore also underestimates the vertical excitation energy. See Liu et al., *J. Phys. Chem. A* 108:3545-3555 (2004); Han et al., *ChemPhysChem* 4:1084-1094 (2003). The directions and approximate magnitudes of the solvatochromic shift, however, are correctly predicted. A small red shift for I-TBA was observed with increasing solvent polarity from $C_6H_6$ to OcOH (with $\Delta E_{abs}$=0.02 1 eV, or $\Delta\lambda_{max}$=6 nm). A slight red shift was predicted for this molecule from $C_6H_6$ to MeOH (with $\Delta E_{abs}$=0.0 12 eV). Without wishing to be bound to any one particular theory, the observed blue shift from OcOH to MeOH solutions ($\Delta\lambda_{max}$=7 nm) is possibly caused by the explicit interactions (for instance H-bonding interactions) between the solute and solvent molecules.

9.4.3. Broadening of Dye Absorption Bands in Alcohols: Role of H-Bonding

The predyes disclosed herein have very broad absorption bands in polar, hydrogen bonding solvents, such as methanol or ethanol (see FIG. 11). The width of a band in the absorption spectrum of a chromophore in solution is a result of two effects: homogeneous broadening and inhomogeneous broadening.

Homogeneous broadening is due to the existence of a continuous set of vibrational sublevels in each electronic state. The homogenous broadening can be important for dyes with a ground state lying far from the cyanine limit. This characteristic can be understood by considering that a large amount of charge transfer can result in a large displacement of the excited state potential surface along the solvent reorganization coordinate, leading to a larger degree of direct absorption into higher vibronic levels in the excited state. See Bublitz et al., *J. Am. Chem. Soc.* 119:3365-3376 (1997). Inhomogeneous broadening results from the fluctuation of the structure of the solvation shell surrounding the solute. In MeOH solution, there will be more explicit interactions between the solute and the surrounding solvent molecules through H-bonding. Different patterns and numbers of H-bonding interactions can result in a distribution of solute-solvent configurations. The consequent variation in the local electric field leads to a statistical distribution of energies of the electronic transitions. Also, upon excitation, different solute structures and energies can result from the v=0 vibrational level to v=n transitions in the $S_1$ state. Therefore, the broad absorption bands in MeOH solution result from homogeneous and inhomogeneous effects.

To investigate how explicit H-bonding and how different numbers of H-bonding interactions influence the solute structure and properties, AI-BA(4) was selected as an example and put one, two and three explicit $CH_3OH$ molecules H-bonding to the solute in different positions (FIG. 13). The +1$CH_3OH$ (I) model contains one $CH_3OH$ molecule at position I, the +2$CH_3OH$(I,II) model has two $CH_3OH$ molecules in total at positions I and II, and the +3$CH_3OH$(I,II,III) model contains all three H-bonding $CH_3OH$ molecules at I, II and III, respectively. The geometries were then optimized using the COSMO model in ADF.

The main bond lengths of these structures are given in Table 13. For comparison, the values for the structure without explicit H-bonding partners also are included. The geometry of AI-BA(4) changes upon interaction with the solvent molecule and also changes with increasing numbers of the H-bonding solvent molecules. First, the central C—C bonds can be considered. Without including explicit H-bonding interactions, the $C_2$-$C_3$, $C_3$-$C_4$, $C_4$-$C_5$, $C_5$-$C_6$, and $C_6$-$C_7$ bond lengths are 1.427, 1.393, 1.416, 1.387, and 1.421 Å, respectively, with single, double, single, double, and single bond characters, consistent with Chart 1. By including one and two H-bonding $CH_3OH$ molecules, these bonding characters are strengthened, with $C_2$-$C_3$, $C_4$-$C_5$, and $C_6$-$C_7$ lengthened, and $C_3$-$C_4$, and $C_5$-$C_6$ shortened. In the +3$CH_3OH$(I,II,III) model, the bond lengths of $C_2$-$C_3$, $C_4$-$C_5$, and $C_6$-$C_7$ reach the largest values of 1.444, 1.418, and 1.425 Å, and $C_3$-$C_4$, and $C_5$-$C_6$ are the shortest bonds 1.380 and 1.383 Å, respectively, among the calculated models. By including explicit H-bonding interactions, the bonding characters of $C_1$-$C_{19}$ and $C_{16}$-$C_{17}$ are weekend, and those of $C_7$-$C_8$ and $C_7$-$C_9$ are strengthened.

Note that the presently disclosed calculations correspond to $S_0(v=0) \rightarrow S_1$ vertical transitions. Specifically for absorption, these calculations are performed in the optimal ground state geometry, and the excited state is calculated in the same geometry, assuming the Frank-Condon principle. The $S_0(v=0) \rightarrow S_1(v=n)$ (n is largely unidentified) transitions from a distribution of solute-solvent configurations can result in a large span of excitation energies, which are further broadened by the distribution of H-bonding solvent molecules.

In Table 14, the calculated and observed energy difference of $E_{abs}(MeOH)$–$Eabs(C_6H_6)$ were compared, which represents the blue shift of the absorption band of AI-BA(4) with increasing solvent polarity from $C_6H_6$ to MeOH. The predicted energy shift gets closer to the experimental value each time one, two, and three explicit H-bonding $CH_3OH$ mol-

TABLE 13

Main Bond Lengths (Å) of the $S_0$ State AI-BA(4) Structure in MeOH with 0, 1, 2 and 3 Explicit H-Bonding $CH_3OH$ Molecules.[a]

| Bond | +0$CH_3OH$ | +1$CH_3OH$(I) | +2$CH_3OH$(I, II) | +3$CH_3OH$(I, II, III) |
|---|---|---|---|---|
| $C_2$—$C_3$ | 1.427 | 1.435 | 1.443 | 1.444 |
| $C_3$—$C_4$ | 1.393 | 1.382 | 1.381 | 1.380 |
| $C_4$—$C_5$ | 1.416 | 1.414 | 1.418 | 1.418 |
| $C_5$—$C_6$ | 1.387 | 1.385 | 1.384 | 1.383 |
| $C_6$—$C_7$ | 1.421 | 1.420 | 1.424 | 1.425 |
| $C_7$—$C_8$ | 1.451 | 1.445 | 1.442 | 1.441 |
| $C_7$—$C_9$ | 1.450 | 1.445 | 1.447 | 1.444 |
| $C_1$—$C_{19}$ | 1.369 | 1.373 | 1.373 | 1.373 |
| $C_{16}$—$C_{17}$ | 1.371 | 1.385 | 1.390 | 1.390 |

[a]See atomic labels of AI-BA(4) in FIG. 12, and the $CH_3OH$ molecular positions of I, II, and III in FIG. 13. Geometries were optimized using the COSMO model in ADF.

The SCRF/VSCRF calculated dipole moment values and vertical excitation energies for these models are given in Table 14. As provided in Table 14, the dipole moment of the solute increases with increasing number of H-bonding solvent molecules. Different models in MeOH produce different absorption energies ($E_{abs}$), and the $E_{abs}$ value increases with increasing numbers of the H-bonding solvent molecules. The orientation and the number of the H-bonding interactions between the solute and the solvent molecules, however, can vary and can be different from the presently disclosed models. The calculations here, however, show that the absorption energy of the solute is influenced by the number and patterns of H-bonding interactions. The excitation energy differences predicted among the different MeOH H-bonding models are not as large as the broadening observed experimentally. The inhomogeneous broadening includes molecular dynamics effects, which has not been taken into account, and homogeneous broadening, as well.

TABLE 14

SCRF/VSCRF Calculated Absorption (or Excitation) ($E_{abs}$) Energies (eV), and the Relaxed $S_0$ State ($\mu_{S0}$) and Vertical $S_1$ ($\mu^v_{S1}$) State Dipole Moments (D) for AI-BA(4) in different H-bonding Models in MeOH.

| | | | Absorption | | |
|---|---|---|---|---|---|
| | | | $E_{abs}$ | $E_{abs}(MeOH)$-$E_{abs}(C_6H_6)$[a] | |
| Model | $\mu_{S0}$ | $\mu^v_{S1}$ | Cal | Cal | Exp |
| +0$CH_3OH$ | 28.60 | 21.60 | 1.583 | 0.172 | |
| +1 $CH_3OH$ | 31.44 | 24.03 | 1.611 | 0.200 | |
| +2$CH_3OH$ | 33.31 | 25.64 | 1.631 | 0.220 | 0.247 |
| +3$CH_3OH$ | 34.63 | 26.89 | 1.648 | 0.237 | |

[a]The values of $E_{abs}$ (MeOH) are the $E_{abs}$ values given in the table for different models. $E_{abs}(C_6H_6)$ = 1.411 eV, which was given in Table 12.

ecules are added into the quantum region. Especially when considering three H-bonding $CH_3OH$ molecules, the predicted energy shift 0.237 eV is in good agreement with the experimental value of 0.247 eV. The possible explicit H-bonding effects can be taken into account to predict the correct order and reasonable relative excitation energies of the solute molecule in different solvents.

9.4.4. Fluorescence Spectra of the Presently Disclosed Dyes

The experimental emission data for the presently disclosed dyes are summarized in Table 15. The SCRF/VSCRF predicted emission energies and the solute dipole moments before and after the vertical emission process are given in Table 16. The dipole moments of AI-BA(4) and AI-SO(4) are further decreased on the $S_1$ surface after geometry relaxation (in MeOH solution), and then increased during the $S_1 \rightarrow S_0$ transition. This observation is consistent with the blue shifts of the emission bands of AI-BA(4) and AI-SO(4) with increasing solvent polarity from $C_6H_6$ to MeOH. By contrast, the dipole moment of I-SO further decreases after $S_1$ state geometry relaxation, and then decreases during the vertical emission process. This observation also is in agreement with the red shift of the I-SO emission band with increasing solvent polarity from $C_6H_6$ to MeOH. Similarly to the absorption case, a negligible red shift ($\Delta E_{em}$=0.017 eV) was predicted for the emission band of I-TBA with increasing solvent polarity. A small red shift from $C_6H_6$ to DMF (with $\Delta E_{em}$=0.020 eV, or $\Delta \lambda_{max}$=6 nm) is observed. The nearly equal emission energy observed in $C_6H_6$ and MeOH can again result in the explicit interactions between the solute and solvent molecules.

TABLE 15

Observed Emission Properties of Dyes 1a, b, 2a-d, 3 and 4.

| Solvent | 3<br>I-TBA<br>$\lambda_{max}$/nm<br>($\Phi^a$) | 4<br>I-SO<br>$\lambda_{max}$/nm<br>($\Phi$) | 2a,<br>AI-SO(4)<br>$\lambda_{max}$/nm<br>($\Phi$) | 2b,<br>AI-BA(4)<br>$\lambda_{max}$/nm<br>($\Phi$) | 2d,<br>P-SO(4)<br>$\lambda_{max}$/nm<br>($\Phi$) | 1a,<br>P-SO(2)<br>$\lambda_{max}$/nm<br>($\Phi$) | 1b,<br>AI-SO(2)<br>$\lambda_{max}$/nm<br>($\Phi$) |
|---|---|---|---|---|---|---|---|
| MeOH | 603 (0.26) | 615 (0.08) | 665 (0.54) | 618 (0.52) | 630 (0.018) | 529 (0.005) | 561 (0.05) |
| EtOH | —[b] | — | 671 (0.82) | 651 (0.19) | 634 (0.029) | 533 (0.008) | 563 (0.09) |
| i-PrOH | — | — | 673 (0.96) | 652 (0.22) | 636 (0.049) | 532 (0.014) | 565 (0.13) |
| BuOH | 609 (0.61) | 618 (0.54) | 675 (0.92) | 654 (0.29) | 640 (0.048) | 535 (0.015) | 567 (0.16) |
| OcOH | 609 (0.99) | 617 (0.98) | 679 (0.88) | 656 (0.64) | 644 (0.082) | 536 (0.024) | 569 (0.21) |
| DMF | 611 (0.94) | 615 (0.97) | 673 (−1.0) | 658 (0.26) | 635 (0.10) | 534 (0.025) | 567 (0.16) |
| DMSO | — | — | 673 (−1.0) | 657 (0.23) | 636 (0.067) | 535 (0.024) | 567 (0.24) |
| $CH_3CN$ | — | — | 667 (0.75) | 652 (0.05) | 632 (0.067) | 531 (0.011) | 561 (0.06) |
| $CH_2Cl_2$ | — | — | 681 (0.54) | 664 (0.03) | 650 (0.082) | 541 (0.01) | 571 (0.06) |
| $C_6H_6$ | 605 (0.20) | 603 (0.42) | 691 (0.19) | 670 (0.01) | 656 (0.002) | 546 (0.004) | 577 (0.02) |

TABLE 16

SCRF/VSCRF Calculated and Experimentally Observed Emission
($E_{em}$) Energies (eV), and the Relaxed $S_1$ State ($\mu_{S1}$)
and Vertical $S_0$ ($\mu^v{}_{S0}$) State Dipole Moments (D)
for the Dye Molecules in $C_6H_6$ and in MeOH.
Emission

| Solute | Solvent | X | $\mu^v{}_{S1}$ | $\mu^v{}_{S0}$ | $E_{em}$ Cal | Exp |
|---|---|---|---|---|---|---|
| I-TBA | $C_6H_6$ | | 18.21 | 17.00 | 1.506 | 2.050 (605 nm) |
|  | MeOH | | 23.06 | 21.61 | 1.489 | 2.056 (603 nm) |
|  | $C_6H_6$ | | 17.27 | 20.07 | 1.341 | 1.851 (670 nm) |
|  |  | +0 | 19.23 | 23.91 | 1.416 | 2.006 (618 nm) |
|  |  | +1 | 21.37 | 26.57 | 1.426 |  |
| AI-BA(4) | MeOH | +2 | 23.17 | 28.26 | 1.428 |  |
|  |  | +3 | 24.16 | 29.41 | 1.432 |  |
| I-SO | $C_6H_6$ | | 16.85 | 10.55 | 1.629 | 2.056 (603 nm) |
|  | MeOH | | 17.33 | 15.55 | 1.537 | 2.016 (615 nm) |
| AI-SO(4) | $C_6H_6$ | | 18.57 | 18.15 | 1.332 | 1.794 (691 nm) |
|  | MeOH | | 23.00 | 23.31 | 1.381 | 1.865 (665 nm) |

For the emission energy of AI-BA(4) in MeOH, the $E'_{em}$ values also increase with increasing number of the H-bonding solvent molecules. The increment, however, is much less than the corresponding ones in the absorption process. This observation also can be explained by the smaller change of the dipole moment $\mu_{S1}$ from one model to another, compared with the corresponding change of $\mu_{S0}$ and also might be the reason that the width of the emission band in MeOH is not as broad as the absorption band.

9.4.5. Fluorescence Quantum Yield of the Presently Disclosed Dyes

The fluorescence quantum yield ($\Phi$) is determined by the competition between fluorescence and non-radiative pathways. Many factors can affect the fluorescence quantum yield, such as temperature (which influences the intramolecular vibrations, rotations or isomerizations, and the collisions of the solute and solvent, and the like), pH, polarity, viscosity, hydrogen bonding, presence of quenchers, and formation of new complex. See Valeur, *Molecular Fluorescence: Principles and Applications*. WILEY-VCH Verlag GmbH: Weinheim (2002).

The main nonfluorescent deactivation path for the excited state of Merocyanine 540 (MC 540) is photoisomerization around a central double bond. See Benniston, et al., *J. Chem. Soc., Faraday Trans.* 93:3653-3662 (1997); Benniston and Harriman, *J. Chem. Soc., Faraday Trans.* 90:2627-2634 (1994); and Benniston and Harriman, *J. Chem. Soc., Faraday Trans.* 94:1841-1847 (1998). It is thought that partial rotation around the double bound in the excited state of MC 540 can result in formation of a perpendicular transition state that collapses to a highly excited vibronic level of the ground state, with consequent thermal dissipation of energy. See Benniston, et al., *J. Chem. Soc., Faraday Trans.* 93:3653-3662 (1997).

The quantum yield of fluorescence of MC 540 increases with increase in solvent shear viscosity, a trend which also is observed for dyes 1a-b, 2a-d, 3 and 4 (Table 14), suggesting the importance of photoisomerization for the presently disclosed dyes. It has been previously shown that the rate of photoisomerization of MC 540 can be correlated to solvent polarity. For example, in alcohols the photoisomerization rate is higher than in nitriles with similar viscosities. See Onganer et al., *J. Phys. Chem.* 97:2344-2354 (1993). This observation arises partly because the hydrogen bonding alcohols better stabilize the twisted excited state of MC 540, which has a substantial zwitterionic character leading to faster photoisomerization.

Because the explicit solute-solvent interactions vary with the solvents, and many factors can influence the fluorescence and life times, it can be difficult to predict or analyze the $\Phi$ values in each solvent. The presently disclosed subject matter analyzes the geometric and electronic structures of the dye molecules in $C_6H_6$ and in MeOH to investigate how the fluorescence quantum yield changes in general from non-polar to polar solvents without considering the explicit solute-solvent interactions. There is a measurable difference between fluorescence quantum yields in benzene and methanol for dyes AI-SO(4), AI-BA(4) and I-SO, even though these solvents have similar viscosities (Table 14). For I-SO, $\Phi(C_6H_6)$=0.42>$\Phi$(MeOH)=0.08. In contrast, for AI-SO(4), $\Phi(C_6H_6)$=0.19<$\Phi$(MeOH)=0.54. In Table 16, the calculated central C—C bond lengths of the relaxed $S_1$ state for I-SO and AI-SO(4) are presented. The molecular orbital plots of the ground state ($S_0$) HOMO and the $S_1$ state promoted electron are shown in FIG. 14 (for I-SO) and FIG. 15 (for AI-SO(4)). For I-SO, after excitation in $C_6H_6$, the bond lengths of $C_2$-$C_3$, $C_4$-$C_5$ and $C_6$-$C_7$ are lengthened (see Tables 11 and 17), and these three bonds change from bonding to non-bonding, bonding to anti-bonding, and non-bonding to anti-bonding characters, respectively (see FIG. 14). Now r($C_4$-$C_5$)=1.408 Å becomes the longest in the $S_1$ state. It is therefore likely that the main photo-isomerization coordinate is the internal rotation of $C_4$-$C_5$ for I-SO in $C_6H_6$ because this bond is the weakest bond with the greatest single bond character. In MeOH, after excitation, the bond lengths of $C_3$-$C_4$ and $C_5$-$C_6$ are lengthened, and their bonding characters are changed from non-bonding to anti-bonding (for $C_3$-$C_4$) and bonding to non-bonding (for $C_5$-$C_6$). Now r($C_3$-$C_4$)=1.414 Å, and r($C_5$-$C_6$)=1.410 Å. Both are longer than r($C_4$-$C_5$) in $C_6H_6$. Also, the central C—C bonds of the $S_1$ state of I-SO in MeOH have distinct single or double bond character. By contrast, these bonds show very similar distances in $C_6H_6$ solution. Therefore, the internal rotations around $C_3$-$C_4$ and $C_5$-$C_6$ for the $S_1$ state of I-SO in MeOH can be more facile than any bond rotations of the $S_1$ state of I-SO in $C_6H_6$, which could explain why the fluorescence quantum yield of I-SO in MeOH is smaller than in $C_6H_6$.

TABLE 17

Calculated Central C—C Bond Lengths (Å) of the $S_1$ State Adiabetic Minimum Dye Molecules in $C_6H_6$ and in MeOH.

| Solvent | Bond | I-SO | AI-SO(4) | AI-BA(4) |
|---|---|---|---|---|
| $C_6H_6$ | $C_2$—$C_3$ | 1.400 | 1.430 | 1.431 |
| | $C_3$—$C_4$ | 1.402 | 1.403 | 1.400 |
| | $C_4$—$C_5$ | 1.408 | 1.412 | 1.419 |
| | $C_5$—$C_6$ | 1.396 | 1.401 | 1.397 |
| | $C_6$—$C_7$ | 1.405 | 1.398 | 1.415 |
| MeOH | $C_2$—$C_3$ | 1.393 | 1.420 | 1.422 |
| | $C_3$—$C_4$ | 1.414 | 1.416 | 1.413 |
| | $C_4$—$C_5$ | 1.395 | 1.399 | 1.410 |
| | $C_5$—$C_6$ | 1.410 | 1.414 | 1.405 |
| | $C_6$—$C_7$ | 1.397 | 1.392 | 1.414 |

For the $S_1$ state AI-SO(4) in $C_6H_6$, $r(C_2$-$C_3)$=1.430 Å is longer than other central C—C bonds (Table 17), and its bond character changes from bonding to non-bonding upon excitation (FIG. 15). For the $S_1$ state AI-SO(4) in MeOH, though this bond is still the longest (1.420 Å), it has bonding character (FIG. 15) and it is shortened upon excitation (Tables 11 and 17). The other possible rotating bonds are $C_3$-$C_4$ and $C_5$-$C_6$, which are lengthened after excitation, and their bonding characters change from non-bonding to anti-bonding (for $C_3$-$C_4$) and bonding to non-bonding (for $C_5$-$C_6$). These two bond lengths $r(C_3$-$C_4)$=1.416 Å and $r(C_5$-$C_6)$=1.414 Å in MeOH are much shorter than $r(C_2$-$C_3)$=1.430 Å in $C_6H_6$. Therefore, the internal rotation or photo-isomerization for the $S_1$ state AI-SO(4) around $C_2$-$C_3$ in $C_6H_6$ can be more facile than the rotation around $C_2$-$C_3$, $C_3$-$C_4$ or $C_5$-$C_6$ in MeOH, and the fluorescence quantum yield of AI-SO(6) in $C_6H_6$ is thus lower than that in MeOH. The same reason applies for the lower fluorescence quantum yield of AI-BA(4) in $C_6H_6$ relative to MeOH.

9.4.6. Photostability of the Presently Disclosed Dyes

The photostability of dyes can be important for applications in living cells. The mechanism of photobleaching for merocyanines of varying structure has been examined See Toutchkine et al., *J. Am. Chem. Soc.* 125:4132-4145 (2003). The photostability of the presently disclosed dyes was characterized by exposing them to constant illumination from a halogen tungsten lamp filtered through glass. This broad spectrum light source provided essentially equal intensity throughout the spectral range where the dyes absorb and where they would be irradiated in vivo (about 600 nm to about 650 nm). Bleaching occurred through intermediate formation of singlet oxygen. Photobleaching rates of the presently disclosed dyes are compared in Table 18.

The bleaching rates for the dyes differed by two orders of magnitude. The relative rate constants $k_r$ (rel) for product formation during reaction with singlet oxygen were measured by comparing the percent conversions for dyes dissolved in DMSO containing a fixed amount of $^1O_2$ (2.5 mM solutions; $^1O_2$ generated by decomposition of 1,4-dimethylnaphtalene-1,4-endoperoxide). The rates were generally higher for dyes with a polar ground state (1a, 2a, 2b, 2d) than for the dyes with their ground state at the "cyanine limit" (3, 4). Careful analysis of reaction mixtures revealed that the major product of dye 3 photooxidation was indol-2-one 10, while the major product of photooxidation of dye 2a is acetal 11 (FIG. 16, Scheme 22). Olefins without allylic hydrogens react with singlet oxygen to form dioxetanes. Dioxetanes are unstable and decompose, to form two carbonyl compounds.

TABLE 18

Dyes Photobleaching Rates and Reactivity Toward Singlet Oxygen.

| | $k_{ph}$ * 10$^6$, s$^{-1}$ ($k_{ph}$(rel))$^a$ | | |
|---|---|---|---|
| Dye | MeOH | $C_6H_6$ | $k_r$(rel)$^b$ |
| 2a, AI-SO(4) | 89 (261) | 128 (115) | 59.2 |
| 2b, AI-BA(4) | 68 (200) | | 25.6 |
| 1a, P-SO(4) | 28 (82) | | 60.3 |
| 2d, AI-SO(2) | 0.7 (2.1) | | 20.3 |
| 3, I-SO | 0.53 (1.56) | 1.11 (1.00) | 5.24 |
| 4, I-TBA | 0.34 (1.00) | | 1.00 |
| Cy5 | 1.89 (5.56) | | |

$^a k_{ph}$ = absolute rate of photobleaching, $k_{ph}$(rel) = relative rate of photobleaching with respect to standards I-TBA in MeOH and I-SO in $C_6H_6$.
$^b k_r$(rel) = relative rates constants for product formation during reaction of the dyes with singlet oxygen produced chemically.

Scheme 22. Photooxidation of I-SO and AI-SO(4) dyes.

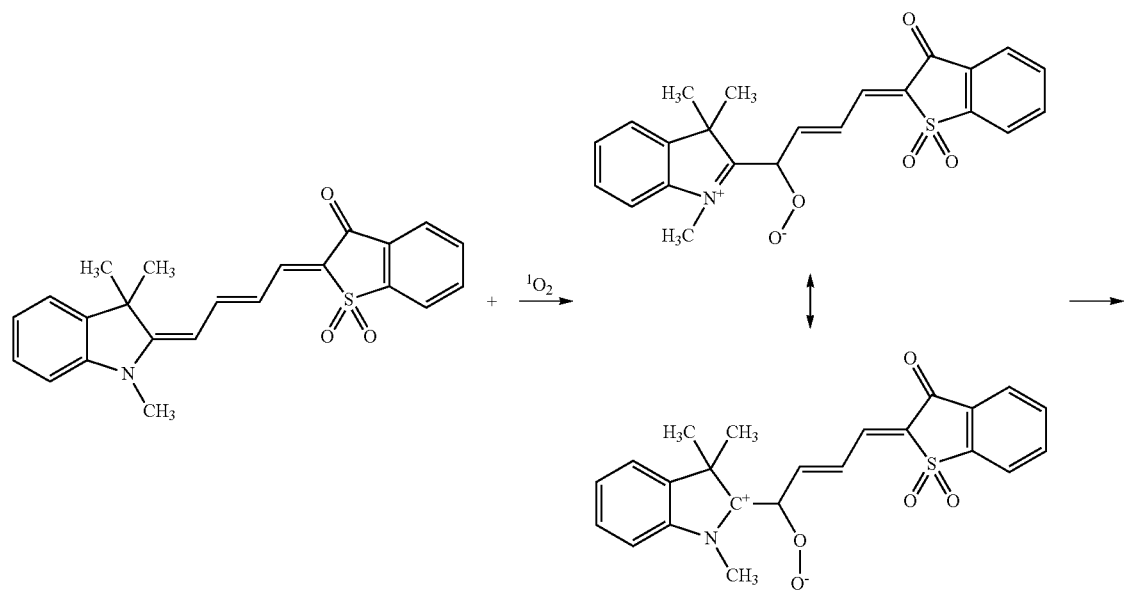

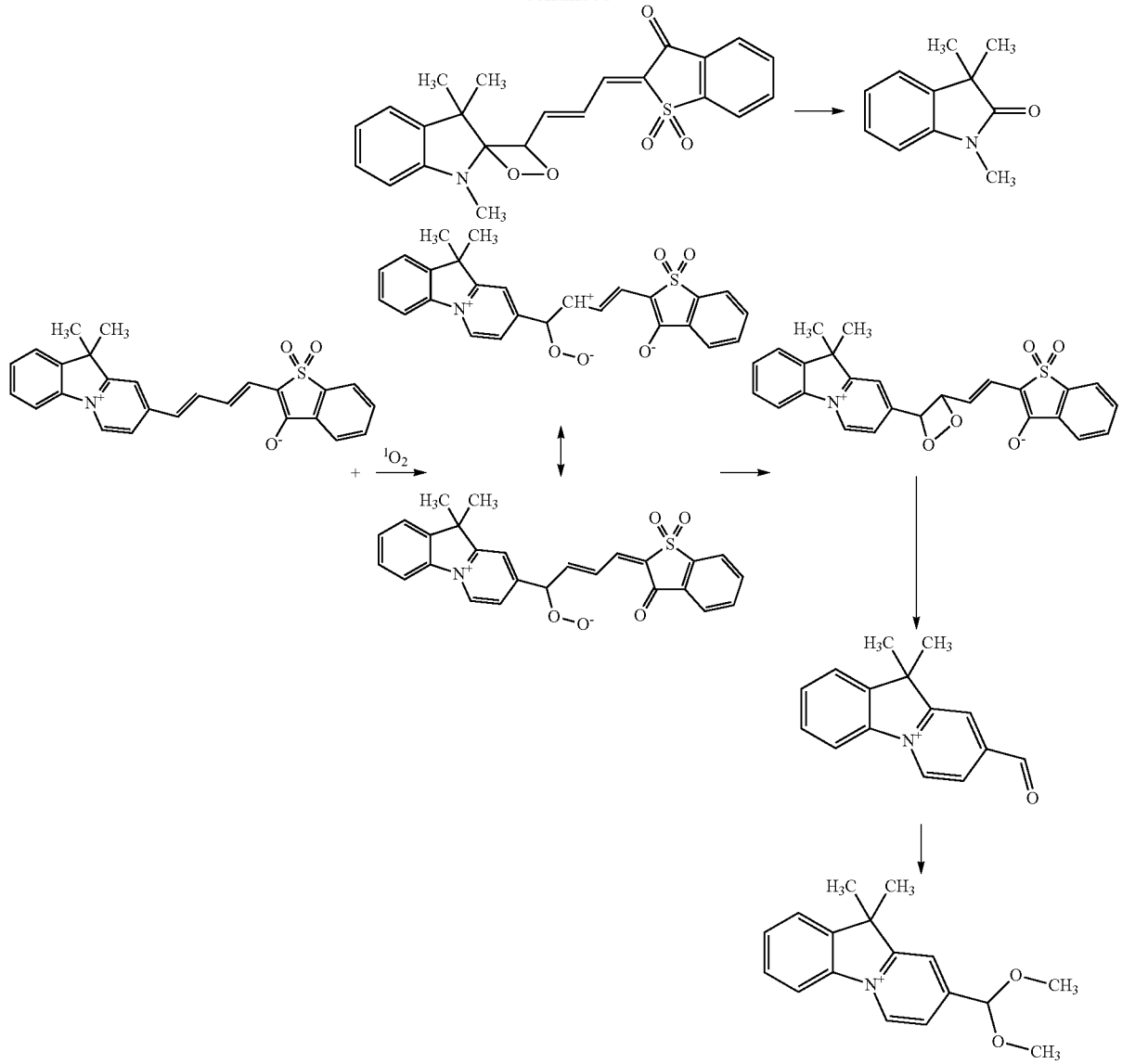

The mechanism of the reaction can be a concerted [2+2] addition of singlet oxygen or it can be a polar reaction, depending on the olefin structure. Olefins with donor substituents react with singlet oxygen to form dioxetanes via zwitterionic 1,4-dipolar species. Because the presently disclosed dyes have donor substituents (nitrogens) it is likely that the reaction proceeds through a zwitterionic mechanism. (Scheme 26). The incipient reactivity of the dyes can be determined by the extent of negative charge at carbon atom $C_3$, which is the most negatively charged atom in the dye molecules (FIG. 17). This can be thought of as a charge-induced dipole interaction between $C_3$ and $^1O_2$. The presently disclosed calculation showed that this charge is higher for AI-SO(4) and AI-BA(4), which react faster with singlet oxygen.

It has been suggested that the initial interaction of $^1O_2$ with C=C bonds is a single-atom, end-on interaction. See Turro, *Modern Molecular Photochemistry*. University Science Books: Mill Valley (1991). Previous studies show that the initial stage of the reaction generally proceeds through charge transfer (substrate electron donor→$^1O_2$ electron acceptor). See id. Therefore, the rates of reaction with $^1O_2$ normally increase as the ionization potential of the substrate decreases. The vertical ionization potentials ($\Delta E_I$) of I-SO, AI-SO(4) and AI-BA(4) were calculated and compared them in Table 19. $\Delta E_I$ is defined as:

$$\Delta E_I = E^+ - E_0 \tag{1}$$

where $E_0$ is the full SCRF energy calculated at the COSMO-optimized geometry of the neutral ground state dye molecule in a certain solvent, and $E^+$ is the VSCRF energy for the dye with a positive charge at the same geometry in the same solvent. The calculated ionization potentials of AI-SO(4) and AI-BA(4) are lower than the corresponding value of I-SO in both $C_6H_6$ and MeOH solutions. It is therefore more facile for AI-SO(4) and AI-BA(4) to transfer an electron to $^1O_2$; AI-SO(4) and AI-BA(4) show much higher photobleaching rates (Table 19) than I-SO, as expected based on the calculated ionization potentials. It also is observed that $\Delta E_I$(MeOH)>$\Delta E_I(C_6H_6)$ for each of the dye molecules, which is consistent with the experimentally observed photobleaching rates of AI-SO(4) and I-SO being higher in $C_6H_6$ than in MeOH.

TABLE 19

Vertical Ionization Potential $\Delta E_I$ (eV) of I-SO, AI-SO(6) and AI-BA(6).

| Solvent | Solute | | |
|---|---|---|---|
| | I-SO | AI-SO(4) | AI-BA(4) |
| $C_6H_6$ | 6.083 | 5.953 | 5.908 |
| MeOH | 6.296 | 6.130 | 6.234 |

9.5. Summary

Novel merocyanine dyes having an enhanced contribution of the zwitterionic ground state resonance form have been prepared through incorporation of a six-membered ring in the electron donor portion of the molecule. Positions of the absorption and emission bands for the presently disclosed dyes strongly depend on solvent polarity. Their photophysical properties can be correctly predicted using the SCRF/VSCRF method plus the COSMO solvation model. The inclusion of explicit H-bonding solvent interactions can be in calculations to predict the correct order of the excitation and emission energies. In contrast to MC540, the presently disclosed dyes exhibit large fluorescence quantum yields in polar hydrogen-bonding solvents. This observation can be explained by the DFT results that charge transfer upon excitation produces an excited state with a low contribution from the zwitterionic form. The non-polar excited state is less susceptible to hydrogen bond formation with solvent and consequent non-radiative activation through photoisomerization.

Photobleaching of the presently disclosed dyes, however, can be useful in making powerful phototoxins. Certain cyanine dyes, such as MC540, can be selectively assimilated into leukemia cells, even in the presence of a large excess of healthy cells. See Benniston, et al., *J. Chem. Soc., Faraday Trans.* 93:3653-3662 (1997); Benniston and Harriman, *J. Chem. Soc., Faraday Trans.* 94:1841-1847 (1998); Singh et al., *Photochem. Photobiol.* 55:483-489 (1992); Franck and Schneider, *Photochem. Photobiol.* 56:271-276 (1992); and Sieber, *Photochem. Photobiol.* 46:1035-1042 (1987).

Such dyes can be used to detect labeled cells and then function as potent phototoxins toward the host cells after photobleaching. MC540, however, suffers from very modest quantum yields of both triplet formation and singlet molecular oxygen generation. There is a potential for an increase in cytotoxicity by improving the photophysical properties without significantly changing molecular properties such as selectivity and cellular/tissue localization. See Redmond et al., *Photochem. Photobiol.* 60:348-355 (1994).

Although the foregoing subject matter has been described in some detail by way of illustration and example for purposes of clarity of understanding, it will be understood by those skilled in the art that certain changes and modifications can be practiced within the scope of the appended claims.

All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

That which is claimed:
1. A dye of Formula (II);

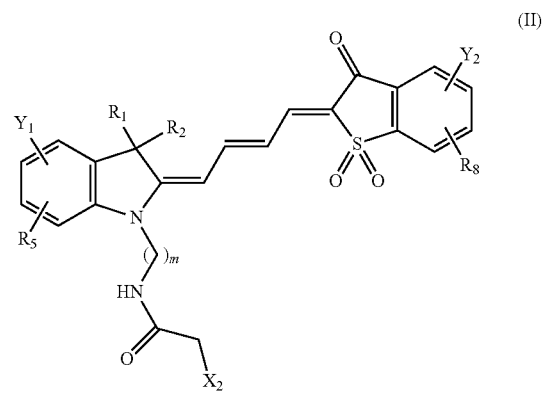

wherein:
m is an integer from 1 to 4;
$X_2$ is halogen;
$R_1$, $R_2$, $R_3$, $R_6$, and $R_7$ are each independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, alkoxycarbonyl, alkyleneaminoalkyl, alkylenesulfate, —$(CH_2)_p$—$SO_3$, —$(CH_2)_p$—$N^+(CH_3)_2$—$(CH_2)_p$NCS, and —$(CH_2)_p$—NH—CO—$CH_2$—$X_2$; wherein $X_2$ is halogen;
$R_5$ is selected from the group consisting of alkyl, substituted alkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, alkoxycarbonyl, alkyleneaminoalkyl, alkylenesulfate, —$(CH_2)_p$—$SO_3$, —$(CH_2)_p$—$N^+CH_3)_2$—$(CH_2)_p$—NCS, and —$(CH_2)_p$—NH—CO—$CH_2$—$X_2$; wherein $X_2$ is halogen;
$R_8$ is selected from the group consisting of H, alkyl, substituted alkyl, hydroxyl, amino, nitro, alkoxyl, and hydroxyalkyl;
$Y_1$ is H;
$Y_2$ is selected from the group consisting of H, —$NH_2$, —$SO_3^-$, —$(CH_2)_rOH$, —$(CH_2)_rNH_3^+X_2^-$; $CH_3CONH$—, $X_2CH_2CONH$—, $HO(CH_2)_2$—S—$CH_2CONH$—, $SuOCOCH_2OCH_2CON(CH_3)$—, —$CH_2$—NH—C(=O)—O—$(CH_3)_3$, —$(CH_2)_r$—$NH_2^+$—$(CH_2)_s$—$SO_3^-$, —$(CH_2)_r$—NH—C(=O)—$(CH_2)_s$—$X_2$, a succinimidyl ester, a hydroxysuccinimide, a maleimide, a haloacetyl, a pyridyl disulfide, a hydrazine, an ethyldiethylamino propylcarbodiimide,

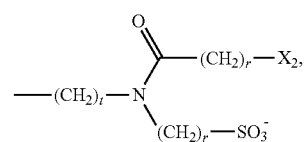

or a protecting group, including t-butoxycarbonyl and carbobenzoxy;

and wherein each p, r, s and t is independently an integer from 1 to 8; and Su is succinimidyl ester;

and salts thereof.

2. The dye of claim 1, wherein $Y_1$ is selected from the group consisting of: —$(CH_2)_2OH$, —$CH_2$—$NH_3^+X_2^-$; —$CH_2$—$NH_2^+$—$(CH_2)_3$—$SO_3^-$; —$CH_2$—NH—C(=O)—$CH_2$—$X_2$; —$CH_2$—NH—C(=O)—O—$(CH_3)_3$;

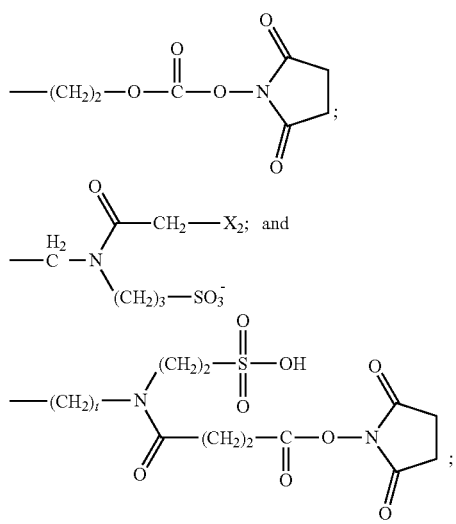

wherein $X_2$ is halogen selected from the group consisting of Cl and I.

3. A dye selected from

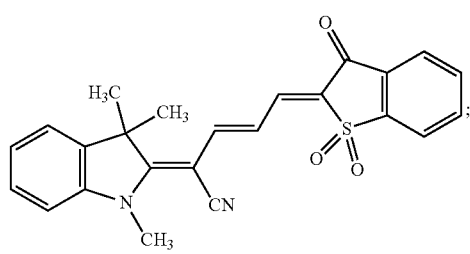

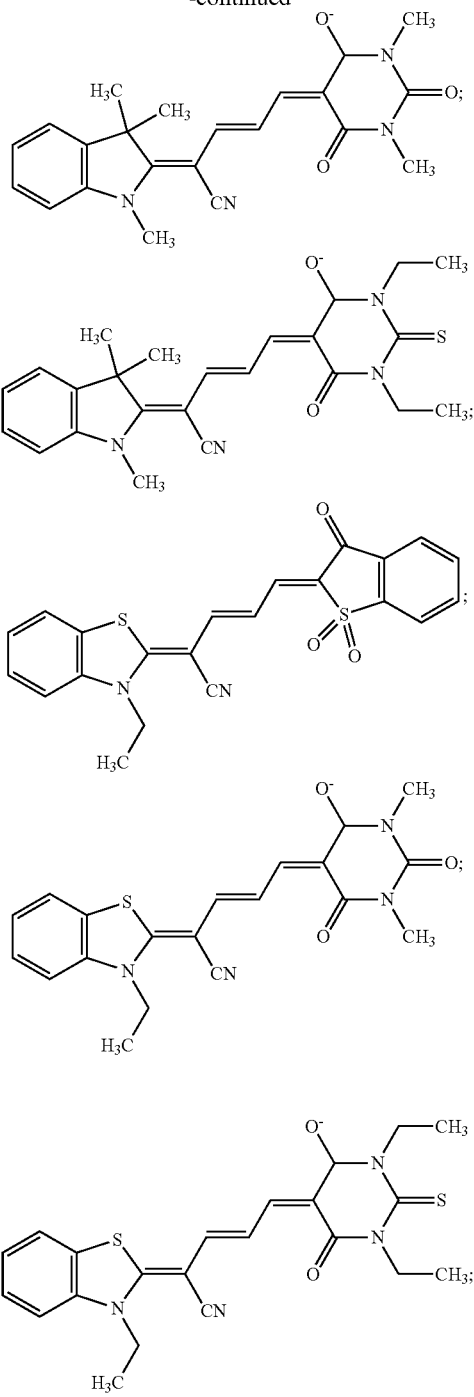

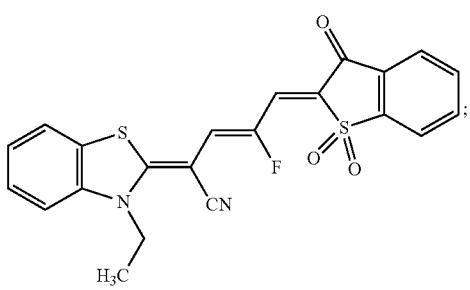

137
-continued
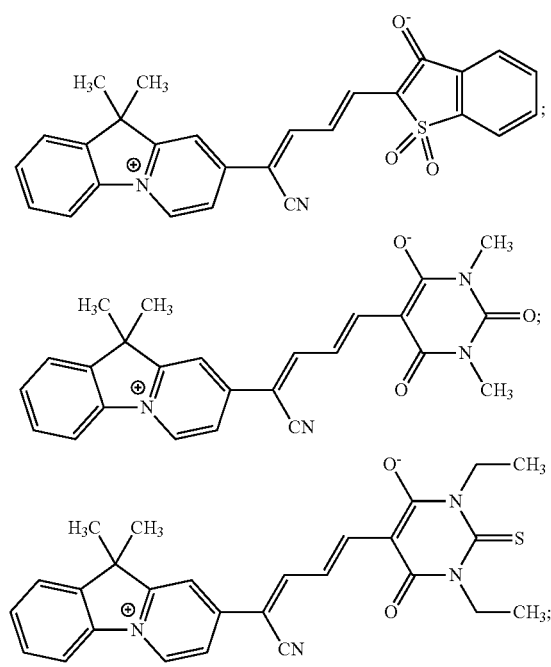
138
-continued
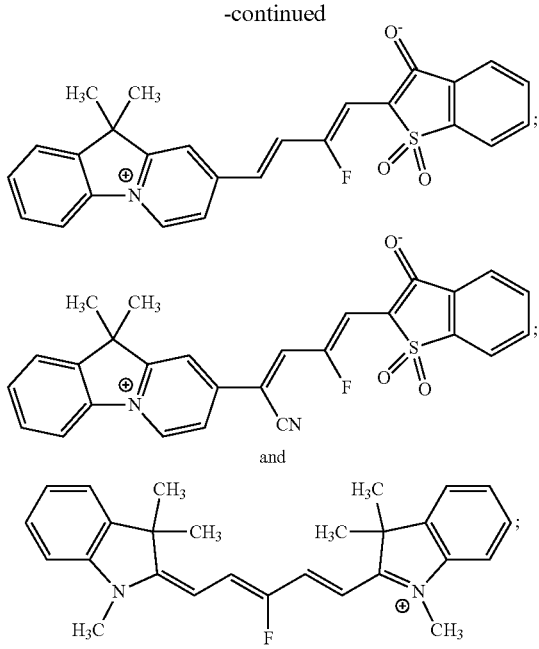
and salts thereof.
* * * * *

UNITED STATES PATENT AND TRADEMARK OFFICE
CERTIFICATE OF CORRECTION

PATENT NO. : 8,835,632 B2  
APPLICATION NO. : 12/743128  
DATED : September 16, 2014  
INVENTOR(S) : Hahn et al.

Page 1 of 4

It is certified that error appears in the above-identified patent and that said Letters Patent is hereby corrected as shown below:

In the Specification:

Column 13, Lines 40 and 41: Please correct "—$(C_2)_t$—$NH_2^+$—$(CH_2)_s$—$SO_3^-$," to read -- -$(CH_2)_t$—$NH_2^+$—$(CH_2)_s$—$SO_3^-$, --

Column 25, Lines 3 and 4: Please correct "—$(CH_2)_t$—NH—(=O)—$(CH_2)_s$—B," to read -- —$(CH_2)_t$—NH—C(=O)—$(CH_2)_s$—B, --

Columns 93 and 94, Example 7, Scheme 11: Please correct

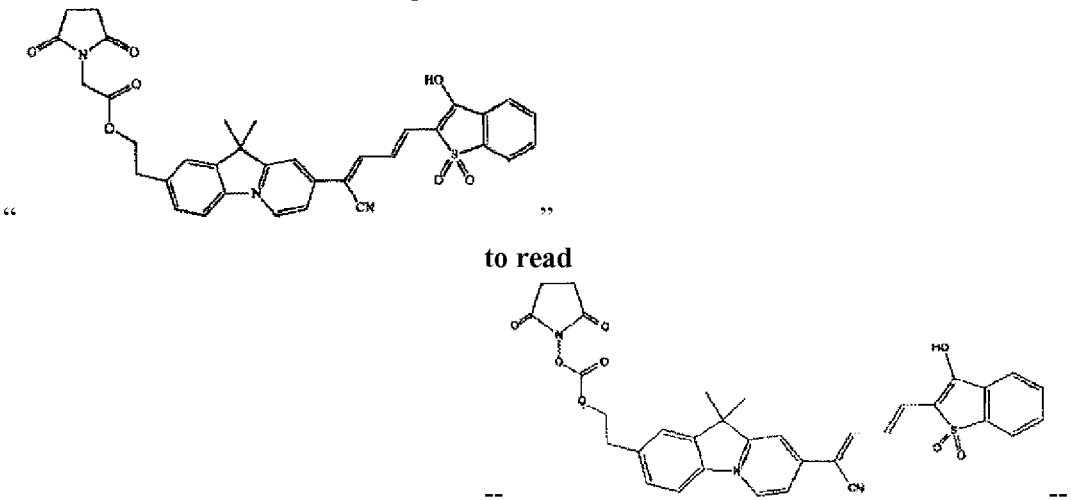

" to read

--

--

Signed and Sealed this
Twenty-fourth Day of November, 2015

Michelle K. Lee  
*Director of the United States Patent and Trademark Office*

Columns 93 and 94, Example 7, Scheme 11: Please correct
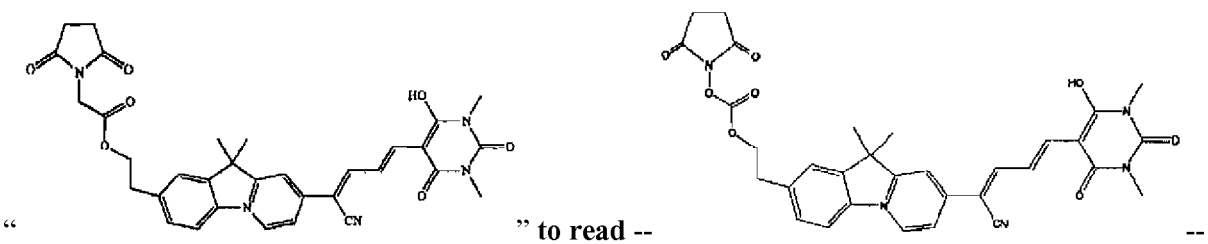
" to read --
Columns 95 and 96, Scheme 11: Please correct
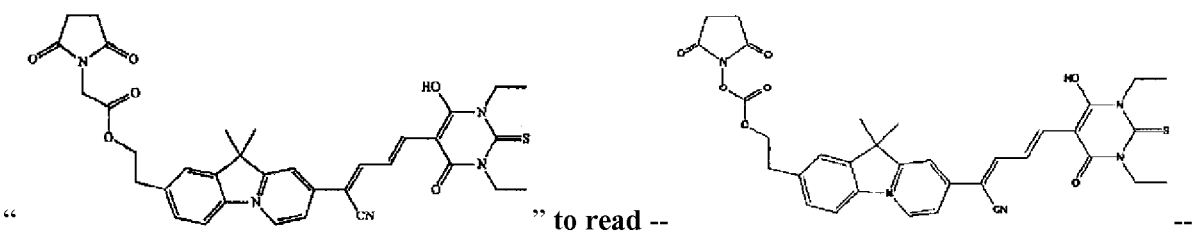
" to read --
Columns 103 and 104, Scheme 15: Please correct
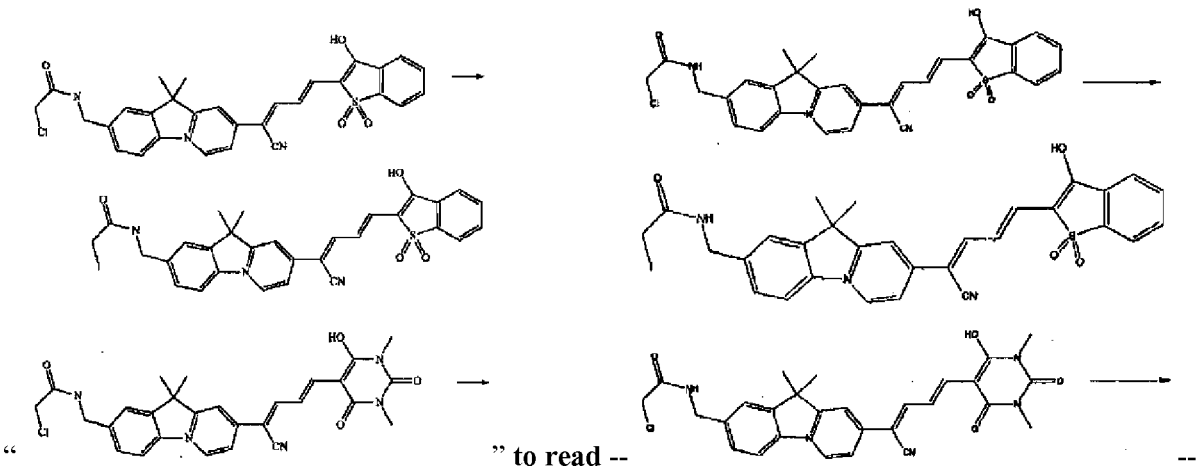
" to read --
Columns 105 and 106, Scheme 15 (continued): Please correct
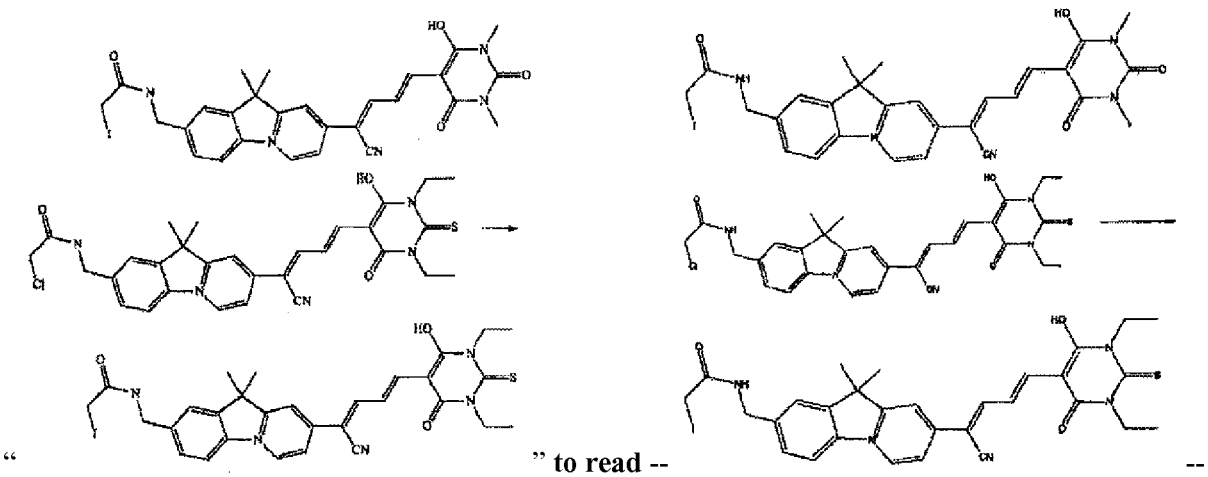
" to read --

CERTIFICATE OF CORRECTION (continued)
U.S. Pat. No. 8,835,632 B2

Page 3 of 4

Columns 109 and 110, Scheme 16: Please correct

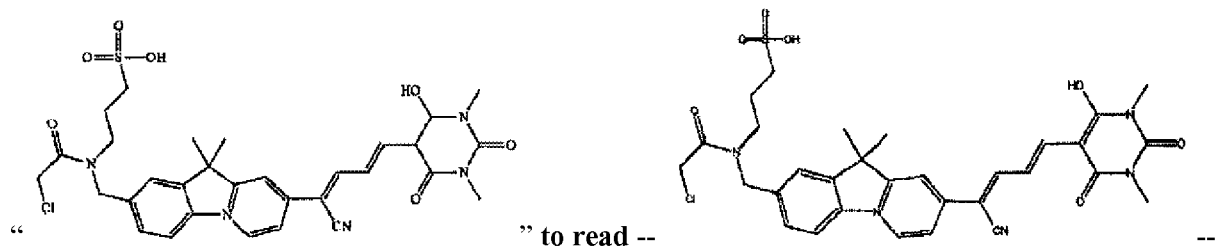

Columns 111 and 112, Scheme 16: Please correct

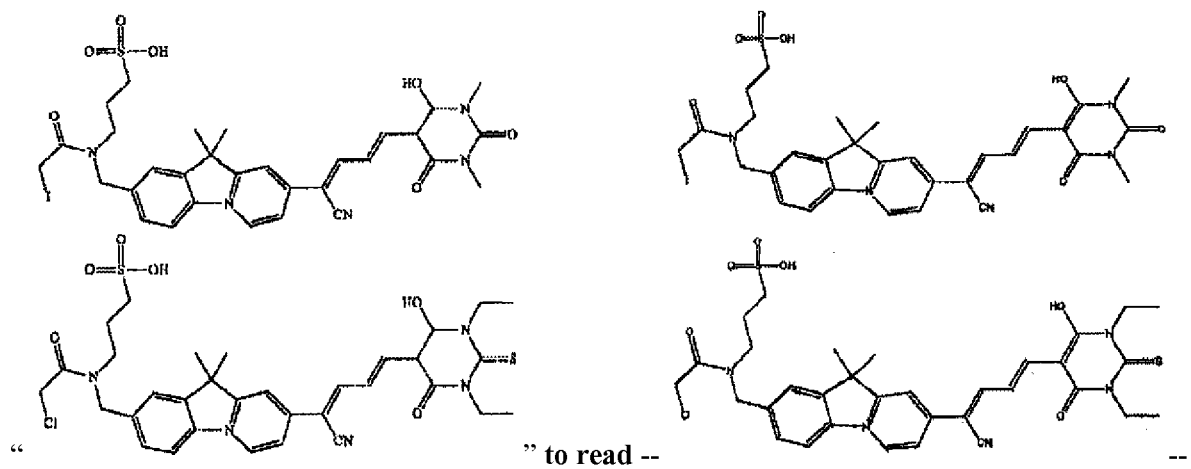

Columns 119 and 120: Please correct

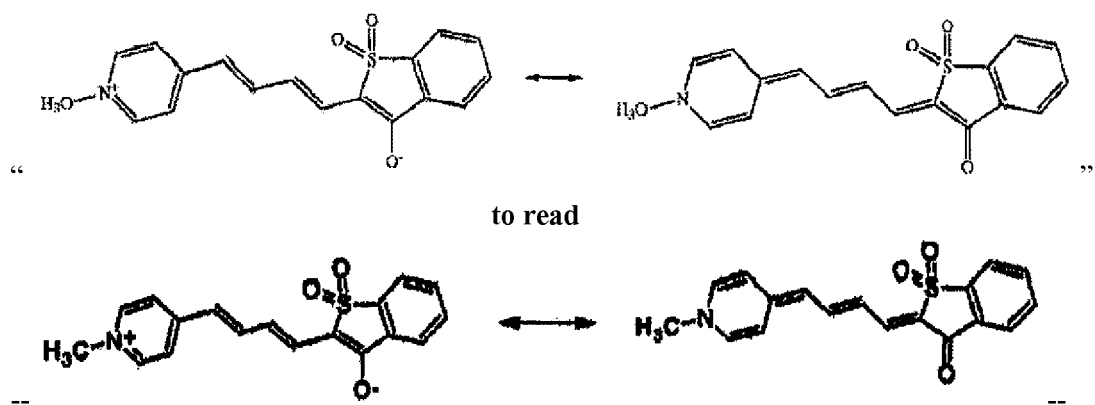

In the Claims:
Column 134, Claim 1, Line 33: Please correct "—(CH$_2$)$_p$—N$^+$(CH$_3$)$_2$—(CH$_2$)$_p$NCS,"
to read -- —(CH$_2$)$_p$—N$^+$(CH$_3$)$_2$—(CH$_2$)$_p$—NCS, --

Column 135, Claim 1, Lines 10-15: Please correct the formula below

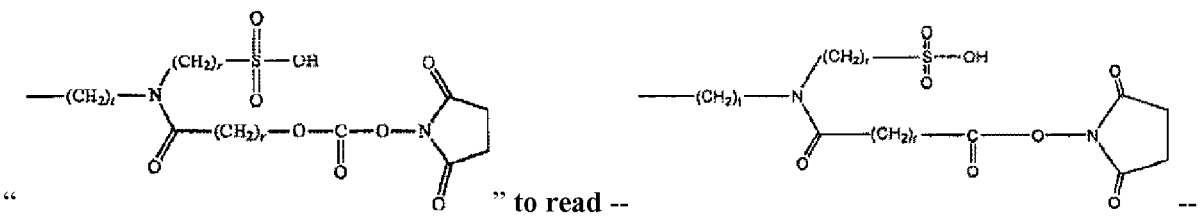
" to read --
Column 135, Claim 3, Line 55: Please correct "A dye selected from"
to read -- A dye selected from: --
Column 137, Claim 3, Lines 1-5: Please delete double bond for O⁻:
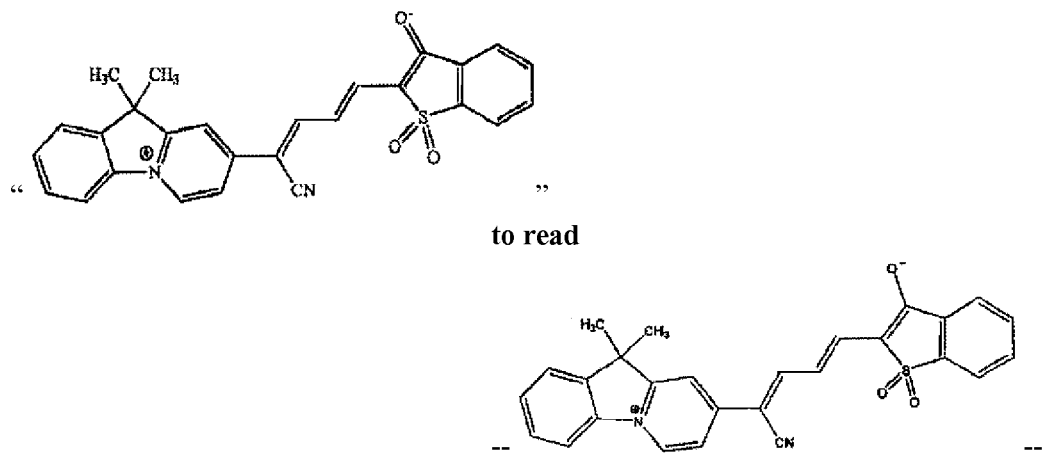
to read
Column 138, Claim 3, Lines 1-18: Please delete double bond for O⁻:
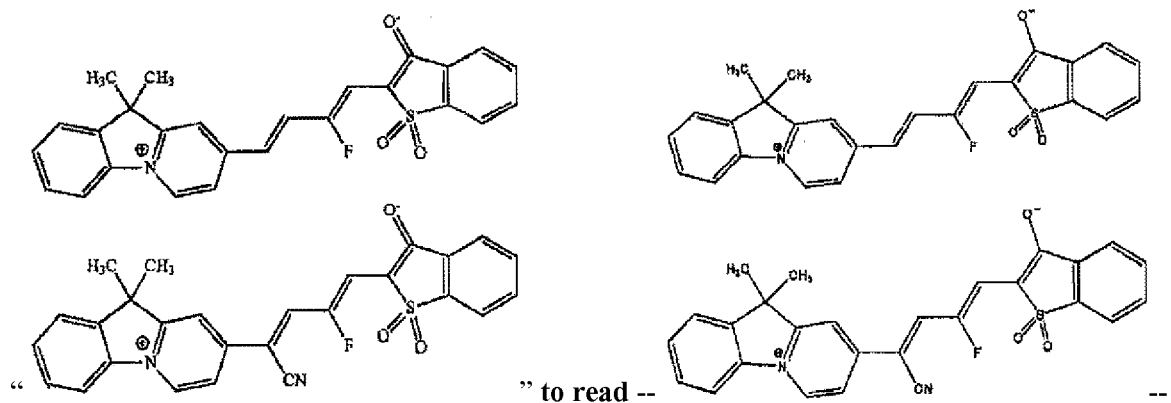
" to read --